United States Patent
Liu et al.

(10) Patent No.: US 10,357,542 B2
(45) Date of Patent: Jul. 23, 2019

(54) PROGRANULIN (PGRN) AND ITS DERIVATIVES FOR DIAGNOSIS AND TREATMENT OF LYSOSOMAL STORAGE DISEASES

(71) Applicants: Chuanju Liu, Orange, CT (US); Jinlong Jian, River Edge, NJ (US)

(72) Inventors: Chuanju Liu, Orange, CT (US); Jinlong Jian, River Edge, NJ (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/116,122

(22) PCT Filed: Feb. 4, 2015

(86) PCT No.: PCT/US2015/014364
§ 371 (c)(1),
(2) Date: Aug. 2, 2016

(87) PCT Pub. No.: WO2015/119989
PCT Pub. Date: Aug. 13, 2015

(65) Prior Publication Data
US 2017/0049855 A1    Feb. 23, 2017

Related U.S. Application Data

(60) Provisional application No. 61/935,541, filed on Feb. 4, 2014.

(51) Int. Cl.
| | |
|---|---|
| *A61K 38/18* | (2006.01) |
| *A61K 38/47* | (2006.01) |
| *A61K 49/00* | (2006.01) |
| *A61K 45/06* | (2006.01) |
| *G01N 33/68* | (2006.01) |
| *C07K 14/47* | (2006.01) |
| *A01K 67/027* | (2006.01) |
| *C12Q 1/6883* | (2018.01) |

(52) U.S. Cl.
CPC .......... *A61K 38/18* (2013.01); *A01K 67/0276* (2013.01); *A61K 38/47* (2013.01); *A61K 45/06* (2013.01); *A61K 49/0008* (2013.01); *C07K 14/47* (2013.01); *C12Q 1/6883* (2013.01); *C12Y 302/01045* (2013.01); *C12Y 302/01052* (2013.01); *G01N 33/6893* (2013.01); *A01K 2217/075* (2013.01); *A01K 2227/105* (2013.01); *A01K 2267/0306* (2013.01); *A01K 2267/0356* (2013.01); *C12Q 2600/156* (2013.01); *C12Q 2600/158* (2013.01); *G01N 2333/47* (2013.01); *G01N 2800/044* (2013.01)

(58) Field of Classification Search
None
See application file for complete search history.

(56) References Cited

U.S. PATENT DOCUMENTS

| | | |
|---|---|---|
| 8,362,218 B2 | 1/2013 | Liu |
| 2002/0127219 A1* | 9/2002 | Okkels .................. A61K 38/24 424/94.61 |
| 2005/0175616 A1 | 8/2005 | Kiener et al. |
| 2009/0239807 A1 | 9/2009 | Horowitz et al. |
| 2010/0105034 A1 | 4/2010 | Hutton et al. |
| 2013/0157945 A1 | 6/2013 | Liu |
| 2013/0230506 A1 | 9/2013 | Jensen et al. |

FOREIGN PATENT DOCUMENTS

| | | |
|---|---|---|
| EP | 2666476 | 11/2013 |
| WO | 2010120374 | 10/2010 |

OTHER PUBLICATIONS

Greiner-Tollersrud et al. (Lysosomal Storage Disorders, In: Madame Curie Bioscience Database [Internet]: Landes Bioscience; 2000, pp. 1-11).*
Lysosomal Storage Disorders (accessed Mar. 12, 2018 at https://rarediseases.org/rare-diseases/lysosomal-storage-disorders/).*
Gieselmann (1995, Biochimica et Biophysica Acta 12.*
Tokuriki et al., 2009, Curr. Opin. Struc. Biol. 19:596-604).*
Bhattacharya et al. (2017, PLoS One 12(3): e0171355, https://doi.org/10.1371/journal.pone.0171355).*
Osher E et al (2011) Pyrimethamine increases β-hexosaminidase A activity in patients with Late Onset Tay Sachs Mol Genet Metab 102(3):356-363.
Petkau TL et al (2014) Progranulin in neurodegenerative disease Trends Neurosci 37(7):388-398.
Platt FM et al (2012) The cell biology of disease: lysosomal storage disorders: the cellular impact of lysosomal dysfunction J Cell Biol 199(5):723-734.
Platt FM (2014) Sphingolipid lysosomal storage disorders Nature 510(7503):68-75.
Porter BF et al (2011) Pathology of GM2 gangliosidosis in Jacob sheep Vet Pathol 48(3):807-813.
Prabakaran T et al (2012) Mannose 6-phosphate receptor and sortilin mediated endocytosis of alpha-galactosidase A in kidney endothelial cells PLoS One 7(6):e39975.
Reczek D et al (2007) LIMP-2 is a receptor for lysosomal mannose-6-phosphate-independent targeting of beta-glucocerebrosidase Cell 131(4):770-783.

(Continued)

*Primary Examiner* — Elizabeth C. Kemmerer
(74) *Attorney, Agent, or Firm* — Hoffmann & Baron, LLP

(57) ABSTRACT

The present invention provides composition and methods for diagnosis and treatment of lysosomal storage diseases and their diagnosis and treatment, including Gaucher's Disease and Tay-Sachs disease, and particularly which utilize progranulin (PGRN), or active PGRN peptides, including atsttrin. The invention also provides animal models of lysosomal storage diseases, including Gaucher's Disease and Tay-Sachs disease, based on or including PGRN mutations including PGRN null mutants and PGRN gene knock outs.

16 Claims, 53 Drawing Sheets
Specification includes a Sequence Listing.

(56) References Cited

OTHER PUBLICATIONS

Rothman JE et al (2011) Molecular mechanism of protein folding in the cell Cell 146(6):851-854.
Saftig P et al (2009) Lysosome biogenesis and lysosomal membrane proteins: trafficking meets function Nat Rev Mol Cell Biol 10(9):623-635.
Smith kr et al (2012) Strikingly different clinicopathological phenotypes determined by progranulin-mutation dosage Am J Hum Genet 90(6):1102-1107.
Sun Y et al (2005) Gaucher disease mouse models: point mutations at the acid beta-glucosidase locus combined with low-level prosaposin expression lead to disease variants J Lipid Res 46(10):2102-2113.
Tanaka Y et al (2013) Increased lysosomal biogenesis in activated microglia and exacerbated neuronal damage after traumatic brain injury in progranulin-deficient mice Neuroscience 250:8-19.
Tanaka Y et al (2014) Possible involvement of lysosomal dysfunction in pathological changes of the brain in aged progranulin-deficient mice Acta Neuropathol Commun 2:78.
Tang W et al (2011) The growth factor progranulin binds to TNF receptors and is therapeutic against inflammatory arthritis in mice Science 332(6028):478-484.
Torres PA et al (2010) Tay-Sachs disease in Jacob sheep Mol Genet Metab 101(4):357-363.
van Swieten JC et al (2008) Mutations in progranulin (GRN) within the spectrum of clinical and pathological phenotypes of frontotemporal dementia Lancet Neurol 7(10):965-974.
Van Weely S et al (1990) Function of oligosaccharide modification in glucocerebrosidase, a membrane-associated lysosomal hydrolase Eur J Biochem 191(3):669-677.
Vitner EB et al (2014) RIPK3 as a potential therapeutic target for Gaucher's disease Nat Med 20(2):204-208.
Wang W et al (2003) PC cell-derived growth factor (granulin precursor) expression and action in human multiple myeloma Clin Cancer Res 9(6):2221-2228.
Wei H et al (2008) ER and oxidative stresses are common mediators of apoptosis in both neurodegenerative and non-neurodegenerative lysosomal storage disorders and are alleviated by chemical chaperones Hum Mol Genet 17(4):469-477.
Witte MD et al (2010) Ultrasensitive in situ visualization of active glucocerebrosidase molecules Nat Chem Biol 6(12):907-913.
Wright WE et al (1989) Myogenin, a factor regulating myogenesis, has a domain homologous to MyoD Cell 56(4):607-617.
Xu YH et al (2010) Comparative therapeutic effects of velaglucerase alfa and imiglucerase in a Gaucher disease mouse model PLoS One 5(5):e10750.
Yang C et al (2014) Celastrol increases glucocerebrosidase activity in Gaucher disease by modulating molecular chaperones Proc Natl Acad Sci USA 111(1):249-254.
Yin F et al (2009) Exaggerated inflammation, impaired host defense, and neuropathology in progranulin-deficient mice J Exp Med 207(1):117-128.
Yin F et al (2010) Behavioral deficits and progressive neuropathology in progranulin-deficient mice: a mouse model of frontotemporal dementia FASEB J. 24(12):4639-4647.
Zanocco-Marani T et al (1999) Biological activities and signaling pathways of the granulin/epithelin precursor Cancer Res 59(20):5331-5340.
Zhao H et al (2003) Gaucher's disease: identification of novel mutant alleles and genotype-phenotype relationships Clin Genet 64(1):57-64.
Zhou J et al (1993) Purification of an autocrine growth factor homologous with mouse epithelin precursor from a highly tumorigenic cell line J Biol Chem 268(15):10863-10869.
Zhu J et al (2002) Conversion of proepithelin to epithelins: roles of SLPI and elastase in host defense and wound repair Cell 111(6):867-878.
Aerts JM et al (1988) Glucocerebrosidase, a lysosomal enzyme that does not undergo oligosaccharide phosphorylation Biochim Biophys Acta 964(3):303-308.

Aerts JMFG et al (2011) Biomarkers in the diagnosis of lysosomal storage disorders: proteins, lipids, and inhibodies J Inherit Metab Dis 34(3):605-619.
Ahmed Z et al (2010) Accelerated lipofuscinosis and ubiquitination in granulin knockout mice suggest a role for progranulin in successful aging Am J Pathol 177(1):311-324.
Almeida S et al (2011) Progranulin, a glycoprotein deficient in frontotemporal dementia, is a novel substrate of several protein disulfide isomerase family proteins PloS One 6(10):e26454.
Baba T et al (1993) Acrogranin, an acrosomal cysteine-rich glycoprotein, is the precursor of the growth-modulating peptides, granulins, and epithelins, and is expressed in somatic as well as male germ cells Mol Reprod Dev 34(3):233-243.
Baker M et al (2006) Mutations in progranulin cause tau-negative frontotemporal dementia linked to chromosome 17 Nature 442(7105):916-919.
Bateman A et al (1990) Granulins, a novel class of peptide from leukocytes Biochem Biophys Res Commun 173(3):1161-1168.
Bateman A et al (2009) The granulin gene family:from cancer to dementia Bioessays 31(11):1245-1254.
Beutler E (1991) Gaucher's disease N Engl J Med 325(19):1354-1360.
Beutler E et al (2001) Gaucher Disease in the Metabolic and Molecular Basis of Inherited Disease CR Scriver et al eds. McGraw Hill, NY pp. 3635-3668.
Blanz J et al (2010) Disease-causing mutations within the lysosomal integral membrane protein type 2 (LIMP-2) reveal the nature of binding to its ligand beta-glucocerebrosidase Hum Mol Genet 19(4):563-572.
Brady RO et al (1965) Metabolism of Glucocerebrosides. Ii. Evidence of an Enzymatic Deficiency in Gaucher's Disease Biochem Biophys Res Commun 18(2)221-225.
Brooks DA (1999) Immune response to enzyme replacement therapy in lysosomal storage disorder patients and animal models Mol Genet Metab 68(2):268-275.
Cenik B et al (2012) Progranulin: a proteolytically processed protein at the crossroads of inflammation and neurodegeneration J Biol Chem 287(39):32298-32306.
Clarke JT et al (2004) An open-label Phase I/II clinical trial of pyrimethamine for the treatment of patients affected with chronic GM2 gangliosidosis (Tay-Sachs or Sandhoff variants) Mol Genet Metab 102(1):6-12.
Cruts M et al (2006) Null mutations in progranulin cause ubiquitin-positive frontotemporal dementia linked to chromosome 17q21 Nature 442(7105):920-924.
Daniel R et al (2000) Cellular localization of gene expression for progranulin J Histochem Cytochem 48(7):999-1009.
Davidson B et al (2004) Granulin-epithelin precursor is a novel prognostic marker in epithelial ovarian carcinoma Cancer 100(10):2139-2147.
Eblan MJ et al (2005) The glucocerebrosidase gene and Parkinson's disease in Ashkenazi Jews N Engl J Med 352(7):728-731.
Fabrega S et al (2000) Human glucocerebrosidase: heterologous expression of active site mutants in murine null cells Glycobiology 10(11):1217-1224.
Farfel-Becker T et al (2011) Animal models for Gaucher disease research Dis Model Mech 4(6):746-752.
Gaspar P et al (2014) Action myoclonus-renal failure syndrome: diagnostic applications of activity-based probes and lipid analysis J Lipid Res 55(1):138-145.
Gonzalez EM et al (2003) A novel interaction between perlecan protein core and progranulin: potential effects on tumor growth J Biol Chem 278(40):38113-38116.
Götzl JK et al (2014) Common pathobiochemical hallmarks of progranulin-associated frontotemporal lobar degeneration and neuronal ceroid lipofuscinosis Acta Neuropathol 127(6):845-860.
Grabowski GA (2008) Phenotype, diagnosis, and treatment of Gaucher's disease Lancet 372(9645):1263-1271.
Grabowski GA (2012) Gaucher disease and other storage disorders. Hematology Am Soc Hematol Educ Program 2012:13-18.
He Z et al (2003) Progranulin is a mediator of the wound response Nat Med 9(2):225-229.

(56) References Cited

OTHER PUBLICATIONS

He Zhiheng et al (2003) Progranulin (granulin-epithelin precursor, PC-cell-derived growth factor, acrogranin) mediates tissue repair and tumorigenesis J Mol Med 81(10):600-612.

Hoque M et al (2003) The growth factor granulin interacts with cyclin T1 and modulates P-TEFb-dependent transcription Mol Cell Biol 23(5):1688-1702.

Hrabal R et al (1996) The hairpin stack fold, a novel protein architecture for a new family of protein growth factors Nat Struct Biol 3(9):747-752.

Hu F et al (2010) Sortilin-mediated endocytosis determines levels of the frontotemporal dementia protein, progranulin Neuron 68(4):654-667.

Ingemann L et al (2014) Lysosomal storage diseases and the heat shock response: convergences and therapeutic opportunities J Lipid Res 55(11):2198-2210.

Jian J et al (2013) Insights into the role of progranulin in immunity, infection, and inflammation J Leukoc Biol 93(2):199-208.

Jian J et al (2013) Progranulin directly binds to the CRD2 and CRD3 of TNFR extracellular domains FEBS Lett 587(21):3428-3436.

Jones MB et al (2003) The granulin-epithelin precursor: a putative new growth factor for ovarian cancer Gynecol Oncol 88(1 pt2):S136-139.

Kirkegaard T et al (2010) Hsp70 stabilizes lysosomes and reverts Niemann-Pick disease-associated lysosomal pathology Nature 463(7280):549-553.

Kolodny E et al (2011) ALBC Newsletter (Pittsboro, North Carolina, USA: American Livestock Breeds Conservancy.

Leverenz JB et al (2007) a novel progranulin mutation associated with variable clinical presentation and tau, TDP43 and alpha-synuclein pathology Brain 130(Pt 5):1360-1374.

Li M et al (2014) Progranulin is required for proper ER stress response and inhibits ER stress-mediated apoptosis through TNFR2 Cell Signal 26(7):1539-1548.

Liu C et al (2014) Progranulin-derived Atsttrin directly binds to TNFRSF25 (DR3) and inhibits TNF-like ligand 1A (TL1A) activity PloS One 9(3):e92743.

Lu R et al (2000) Inhibition of PC cell-derived growth factor (PCDGF, epithelin/granulin precursor) expression by antisense PCDGF cDNA transfection inhibits tumorigenicity of the human breast carcinoma cell line MDA-MB-468 Proc Natl Acad Sci USA 97(8)3993-3998.

Lu J et al (2011) Histone deacetylase inhibitors prevent the degradation and restore the activity of glucocerebrosidase in Gaucher disease Proc Natl Acad Sci USA 108(52)21200-21205.

Mazzulli JR et al (2011) Gaucher disease glucocerebrosidase and alpha-synuclein form a bidirectional pathogenic loop in synucleinopathies Cell 146(1)37-52.

Mu TW et al (2008) Chemical and biological approaches synergize to ameliorate protein-folding diseases Cell 134(5):769-781.

Neculai D et al (2013) Structure of LIMP-2 provides functional insights with implications for SR-BI and CD36 Nature 504(7478):172-176.

Nguyen AD et al (2013) Progranulin: at the interface of neurodegenerative and metabolic diseases Trends Endocrinol Metab 24(12):597-606.

Chen et al., Progranulin associates with hexosaminidase A and ameliorates GM2 ganglioside accumulation and lysosomal storage in Tay-Sachs disease, Journal of Molecular Medicine (2018) 96:1359-1373.

* cited by examiner

FIG. 49

A Human PGRN

```
  1  MWTLVSWVALTAGLVAGTRCPDGQFCPVACCLDPGGASYSCCRPLLDKWPTTLSRHLGGP
 61  CQVDAHCSAGHSCIFTVSGTSSCCPFPEAVACGDGHHCCPRGFHCSADGRSCFQRSGNNS
121  VGAIQCPDSQFECPDFSTCCVMVDGSWGCCPMPQASCCEDRVHCCPHGAFCDLVHTRCIT
181  PTGTHPLAKKLPAQRTNRAVALSSSVMCPDARSRCPDGSTCCELPSGKYGCCPMPNATCC
241  SDHLHCCPQDTVCDLIQSKCLSKENATTDLLTKLPAHTVGDVKCDMEVSCPDGYTCCRLQ
301  SGAWGCCPFTQAVCCEDHIHCCPAGFTCDTQKGTCEQGPHQVPWMEKAPAHLSLPDPQAL
361  KRDVPCDNVSSCPSSDTCCQLTSGEWGCCPIPEAVCCSDHQHCCPQGYTCVAEGQCQRGS
421  EIVAGLEKMPARRASLSHPRDIGCDQHTSCPVGQTCCPSLGGSWACCQLPHAVCCEDRQH
481  CCPAGYTCNVKARSCEKEVVSAQPATFLARSPHVGVKDVECGEGHFCHDNQTCCRDNRQG
541  WACCPYRQGVCCADRRHCCPAGFRCAARGTKCLRREAPRWDAPLRDPALRQLL
```

B Mouse PGRN

```
  1  MWILVSWLAL VARLVAGTQC PDGQFCPVAC CLDQGGANYS CCNPLLDTWP IITSRRLDGS
 61  CQIRDHCPDG YSCLLTVSGT SSCCPFSEGV SCDDGQHCCP RGFHCSADGK SCSQISDSLL
121  GAVQCPGSQF ECPDSATCCI MIDGSWGCCP MPQASCCEDR VHCCPHGASC DLVHTRCISP
181  TGTHPLLKKF PAQRTNRAVA SFSVVCPDAK TQCPDDSTCC ELPTGKYGCC PMPNAICCSD
241  HLHCCPQDTV CDLIQSKCIS KDYTTDLMTK LPGYPVNEVK CDLEVSCPDG YTCCRLNTGA
                                                            GrnA
301  WGCCPFTKAV CCEDHIHCCP AGFQCHTETG TCELGVLQVP WMKKVTASLS LPDPQILKND
361  VPCDDFSSCP SNNTCCRLSS GDWGCCPMPE AVCCLDHQHC CPQGFKCMDE GYCQKGDRMV
     GrnC
421  AGLEKMPVRQ TTLLQHGDIG CDQHTSCPVG QTCCPSLKGS WACCQLPHAV CCEDRQHCCP
                        GrnD
481  AGYTCNVKAR TCEKDAGSVQ PSMDLTFGSK VGNVECGAGH FCHDNQSCCK DSQGGWACCP
                                       GrnE
541  YVKGVCCRDG RHCCPIGFHC SAKGTKCLRK KTPRWDILLR DPAPRPLL
```

FIG.50

Atsttrin peptide sequence (1/2F+P3+P4+1/2A+P5+1/2C):

PQASCCEDRVHCCPHGAFCDLVHTRCITPTGTHPLAKKLPAQRTNRAVALSSSASSKENATTDLLTKLPAHTVGDVKCD
MEVSCPDGYTCCRLQSGAWPWCEQGPHQVPWMEKAPAHLSLPDPQALKRDVPCDNVSSCPSSDTCCQLTSGEWGCCPIP

Other peptide Sequences:
F + P3:
IQCPDSQFECPDFSTCCVMVDGSWGCCPMPQASCCEDRVHCCPHGAFCDLVHTRCITPTGTHP P4 + A:
SKENATTDLLTKLPAHTVGDVKCDMEVSCPDGYTCCRLQSGAWGCCPFTQAVCCEDHIHCCPAGFTCDTQKGTCE P5 + C:
QGPHQVPWMEKAPAHLSLPDPQALKRDVPCDNVSSCPSSDTCCQLTSGEWGCCPIPEAVCCSDHQHCCPQGYTCVAEGQCQ 1/2F+P3+P4+1/2A:
PQASCCEDRVHCCPHGAFCDLVHTRCITPTGTHPLAKKLPAQRTNRAVALSSSASSKENATTDLLTKLPAHTVGDVKCDME
VSCPDGYTCCRLQSGAW P4+1/2A+P5+1/2C:
SKENATTDLLTKLPAHTVGDVKCDMEVSCPDGYTCCRLQSGAWPWCEQGPHQVPWMEKAPAHLSLPDPQALKRDVPCDNVS
SCPSSDTCCQLTSGEWGCCPIP

FIG.51-1

```
   1 CACCTGCCAG TTAAAATCTT CCCAGACTCA GCTCAAGGAG ATGCTCCTAA GGTGGAATGA
  61 AATCTCTTCT TCCCCACCTG GAGACAATCT ACTTCCTCTC CCTACACCTG GCAACTGGCG
 121 CACAACCTTG TATCTTAAAT TAGATTCAGC CTGAGACTGT CTCCCACCAA TCCCTGCTCC
 181 CTGTCCTGCT GAGCACCTTG AGGAAAGGGC TTTGGGGCTG TTTATCTTTG TCCTGGAAAC
 241 CATCCTTCAA CTCACTCTGG GGCCTGCCTA GCATGTCAAC CGAGTTTGGA GAATAGGGCA
 301 GAATAGGGCA GGACAGGACA GGACAAGACA GGGCAGGATA GGATAGGAGC GAGCCAGCTC
 361 AGTAGCTCAC ATTTGTAATC CCAGCGCCTT GGGGGGCTGC GGTAGGAGAA TCGCTTTGGG
 421 AGCAGGAGTT GCAGGCCGCA GTGAGCTATG ATCAGCTTGG GCGACTGAGC GAGACCCTGT
 481 CTCTAAAACA AACACACAAG TCCGGGCGCG GTGGCTCATG CCTGTAATCT TAGCACTTTG
 541 GGAGGCCGAG GTGGGCGGAT CACGAGGTCA AGAAATCGAG ACCATCCTGG CCAACATGGT
 601 GAAACCCCGT CTCTACTAAA AATACAAAAA TTAGCTGGGC GTGGTGGTGC GCGCCTGTAG
 661 TCCCAGCTAC TCGGGAGGCT GAGGCAGGAG AATCGCTTGA ACCCGGGAGG CAGAGGTTGC
 721 AGTGAGCCGA GATCGTGCCA CTGCACTCCA GCCTGGCGAC AGAGTGAGAC TCCGTCTCAG
 781 AACAAACAAA CAAAAGGATA GAAAGGCGAG CACAAATATT CCCAATTCAT AACACTCCCT
 841 CGCACTGTCA ATGCCCCAGA CACGCGCTAT CATCTCTAGC AAACTCCCCC AGGCGCCTGC
 901 AGGATGGGTT AAGGAAGGCG ACGAGCACCA GCTGCCCTGC TGAGGCTGTC CCGACGTCAC
 961 ATGATTCTCC AATCACATGA TCCCTAGAAA TGGGGTGTGG GGCGAGAGGA AGCAGGGAGG
1021 AGAGTGATTT GAGTAGAAAA GAAACACAGC ATTCCAGGCT GGCCCCACCT CTATATTGAT
1081 AAGTAGCCAA TGGGAGCGGG TAGCCCTGAT CCCTGGCCAA TGGAAACTGA GGTAGGCGGG
1141 TCATCGCGCT GGGGTCTGTA GTCTGAGCGC TACCCGGTTG CTGCTGCCCA AGGACCGCGG
1201 AGTCGGACGC AGGTAGGAGA GCGGCCGCGC AGACCTCTCG CCTGCTCCTG CCCAGGGGCC
1261 CGCCAGGGCC ATGTGAGCTT GAGGTTCCCC TGGAGTCTCA GCCGGAGACA ACAGAAGAAC
1321 CGCTTACTGA AACTCCTTGG GGGTTCTGAT ACACTAGGGG GAGTTTTATG GGAAAGAGGA
1381 AGCAGTAATT GCAGTGACGC CCCGTTAGAA GGGGCTTTCT ACCTCCCCAG CATTCCCCCA
1441 AAGCAGGGAC CACACCATTC TTGACCCAGC TCCACCCCTG TCGGTAGGTG CTGGCTTCTT
1501 CCCCTCTCCT GGTGGTGGTG GGTGGTTCCC GCGGCGGCCT GGAGCCGGAG GGGCGCGCGA
1561 CCCTGGGCTG GGAGCTCCGA GGGCCTGGGA ACGAGACCTG AGACCTTGGC TTCTCGAAGG
1621 TAGTAGGGAC TTGGGAGTGG TGACTGAACC TGGTCTGGCT CCTCCTTACT TCCTCTTGTT
1681 GCGGGTGGGA CGAGCTAGCT TCCGCCTCTC CCAGCCACTT TTTCCTGCTC ATTTGCAGCT
1741 AGGTTGGCTC CCCTTTTGGG AATTTCCTCT CCCCTTGGCA CTCGGAGTTG GGGGGTGCCA
1801 CCTAGTGGAA GATAACGGAG CTAGGGTCTT GAAGAGGCTG CTGTCCCCTC TGGCTGTTTT
1861 GGCGGTGTAG GGTGGCATGA GAGACTGCGA CTCGCCTCCT CATCCCTGTT TCTGTATGCG
1921 AGTGCTTGTA TTCAGTAGAA GCATACACTA TACTCCCTCA ATTTAGGGTA AACAGGAGGG
1981 GCCACATGCA CAGGTAATTC ACCAGGGAGC CGAACACTCC TGTGCAGACA GACTCCCCTT
2041 CCCAGCAAGC CATGGCAGCG GACAGCCTGC TGAGAACACC CAGGAAGCAG GCGGTGCCAG
2101 CTGCAGGTGC TTTGCCTGGG AGCTGTGGGG CTGAGGAGAG GGTCCACTGT CCAGGACCAG
2161 TGAACTTCAT CCTTATCTGT CCAGGAGGTG GCCTCTTGGG GATGCTGAGT TAGGGAGGG
2221 GCACTTGAGG AAAGCCAGGT GGAGCAGAGA GGATGTGAGT GACTGGGTGG GTGAGATTTC
2281 CTGCCCCTCC CCCCGCAGTG GTATCCACAC CTAGACTCGT GGGGTAACTG AGGCACAGAC
2341 AGAGAGCAAC TTCTCAGGCC CTCACAGTTG GCAATTCTAG GATTAGGACC CAAGTGCGAT
2401 TTTCAGGCAG TCCCTGTACC CTGTTTCTGT TGTACCTGTT GCACCATTCC CAGGCACTGC
2461 CCATCGTGCC ACTAGTGATA TGAACCCAGG TCCAATACGC TCTGGGGCCA TCAAAGCCTG
2521 ACGTCACCAT GACCTGATGT GTGACGTGTT ATAGGTGTCC CTTGGTATCT TCACGGAACT
2581 GGTTCCAGGA CCCCAAAATC TGTGGGTGCT CAAGCCCCTG AGATAAAATG GTGTAATATT
2641 TGCATATAAC CTATACATAC TTTAAATCAT TTCTAGATTA CTTATACCTA ATACAATGGA
2701 AATGACATGT CGGCTGGGCG TGGTGGCTCA TGCCTGTAAT CCCACCACTT GGGAGGCCG
2761 TGGCAGGTGG ATCACCTGAG GTCTGGAGTT TGAGACCAGC CTGACCAACA TGGTGAAACC
2821 CCCATCTCTA CTAAAAATAC AAAAATTAGC CAGGTGTGGT AGCGCACACC TATAATCCCA
2881 CCTACTTGGG AGGCTGAGGC AGGAGAATTG CTTGAACCTG GGAGGCGGAG TTCGCAGTAA
2941 GCTGAGATCG CGCCACTGTA CTACAGCCTG GGTGACAGAG CAGGACTCCA TCTCAAAAAA
3001 AAAAGAGAAA AGAAAAAGA ATGCCATGT AAATAGTTGT GATCCTGAAT TGTTTAGGGA
3061 ATAATAAGAA AGAACTATCT GTAGATGTTC AGTATAGATG CACCCATCGT AAGCCTAACT
3121 ACATTGTATA ACTCAGCAAC GATGTAACAT TTTCAGGGGT TTTTTGTTT TGTTTTTGA
3181 GACAGAATCT CAGTCTCACT CTGTCACCCA GGCTGGAGTA TGTTGGCGTG ATCTCTGCTC
3241 ACTGCAACCT CCACCTCCTG GGCTCAAGCG ATTCTCCTGC CTCAGCCTCT TGAGTAGCTG
```

FIG. 51-2

```
3301 GGATTGCAGG TGTGCGCTAC CACGCATGGC TAATTTTTGT ATTTTTAATA GAGATGGGGT
3361 TTTACCACGT TGGTCAGGCT GGTCTTGAAC TCCTGACCTT GGGATCCGCC CACCTGGGCC
3421 TCCCAAAGTG CTGGGATTAC AGGCGTTAGC CACCGCGCCC AATATATTTT GATCCCTGGT
3481 TGGATATGGA GGGCTGACTG TACTTAACAT CTCTAAGCTT CAGTTTCCTC CTTTAAAATA
3541 AAGGTGTGGC TGGGTGTGGT GGTTCAAGCC TGTAATCCCA GCACTTAGGG AGGCTGAGGT
3601 GGGTGGATCA GCTGAGGTCA GGAGTTCAAG ACCAGCCTGA CCAATATGGT GAAACCCCCT
3661 CTCTGCTAAA AATACAAAAA TTAGCCAGGC GTGGTGGCGA GCGCCTGTAG TCCCAGCTAC
3721 TTGCTTGAAC TTGGGAGGCA GAGGTTGCAG TGAGCTGAGA TCGTGCCACT GAACTCGAGC
3781 ATGGGCAACA GAGCAAGACT GTCTCAAAAA AAAAAAAAAA AAGGGGGTGA GCAGACGTGG
3841 TGGCACGCTC CCACAGTCCC AGCTACTTAG TAGGAGGCCA AGGTTGGAGG ATTGCTTGAT
3901 CCCAGGAGTC TGAGTCCAGC CTGGGCAACA TGGCAATACC TCATCTCTAA AATAAAATA
3961 AAAGTAAAGG TATTAATTAC TACTTTGGAT GGTTGTTGCA AGAAATATA TATAAATAA
4021 TGGAGAGTCT TGTAACTGGC TCCCAAGAGG CTCAACGAC ATTACTGTTT TTGCTTCTTC
4081 ATTATGAGTT ACCTCTCTGG CCACCCCACT GAACTAGCTG GGCTAGCTGA GCCTGGGAGA
4141 AGAGTTGTTT AGGAAGTGAG AGGCTGCTCT CCACAGAGAC TCAAGGCTCA GTTCCTCCTG
4201 GTGACTCAGA TGGGCAGCCC AGTGGGCACA CGTGGTCTCT CTCCACATGT GGCTGAGTTT
4261 CACTTCCAGA ATAGATGGAG AGGCAAGGGC AGGGTTTAGC ATGCTTGAGG AATCTCAGAG
4321 GGCCCTGGTG GTGTGGGGGA CCCTCAGAAC ACAGGTGTCT CAAGGGCTGA CCCAGCTTCT
4381 GTGTCCTTTT CTCTGGGTGA GGAGGGGACA TTCATGGGCA GATGGTGACC TCTGGGGAAG
4441 GCAGCCCAGA CTCCACTGGC CACCATATTT CCTTTTTCAC AACTTTCTCA CCCCTGTGGT
4501 TTCCCATGTC ATCATGTGGC CGCTTCCCGC AAGGCCTTAG CGGGGTGCAG GTATGAACAT
4561 AGTGTCAGGC AAGGAGGCAT CTGGAGGGGA ACCCTGGCTT TTCCTGGGGG GACTCCCTCC
4621 CTGCACCCTA GCCCTGTCCT CTCCCATGGC TACTGATGCC TTCCCCTCAC CCCAGAGGTG
4681 GCCCACATCT GCACAGATCA GACCCACAAA AATCACGTCT TCCTGACTCT CATAAGCCTG
4741 CCCAGTGAGG CCCAGGCATT AGGCCATGTG CTGGGGACTC AGACCCACAC ATATACGCAT
4801 GTCAGCATTC ATGCTTACAG GTCCGCACAT GCTGGGGCAA GTGTCACACA CGGGGCGCTG
4861 TAGGAAGCTG ACTCTCAGCC CCTGCAGATT TCTGCCTGCC TGGACAGGGA GGTGTTGAGA
4921 AGGCTCAGGC AGTCCTGGGC CAGGACCTTG GCCTGGGGCT AGGGTACTGA GTGACCCTAG
4981 AATCAAGGGT GGCGTGGGCT TAAGCAGTTG CCAGACGTTC CTTGGTACTT TGCAGGCAGA
5041 CCATGTGGAC CCTGGTGAGC TGGGTGGCCT TAACAGCAGG GCTGGTGGCT GGAACGCGGT
5101 GCCCAGATGG TCAGTTCTGC CCTGTGGCCT GCTGCCTGGA CCCCGGAGGA GCCAGCTACA
5161 GCTGCTGCCG TCCCCTTCTG GTGAGTGCCC CTCAGCCTAG GCAAGAGCTG GCAGCCTGGG
5221 TTTTCCCAAA GGGTCATCTT GGATTGGCCA GAGGAGGACG CCAGGCACAA GTCTGTGGTT
5281 TATCATTTTC CCTGTCTTTC TAGGACAAAT GGCCACAAC ACTGAGCAGG CATCTGGGTG
5341 GCCCCTGCCA GGTTGATGCC CACTGCTCTG CCGGCCACTC CTGCATCTTT ACCGTCTCAG
5401 GGACTTCCAG TTGCTGCCCC TTCCCAGAGG TGAGCGTGCC ATCAGCCCAG TGGAGGGGCT
5461 TAGGTCTGCA TTTATGCTTT TCCTGCACTC TACCACCTGC AGATAAAAGG GCCCTGCCAA
5521 TGCAGGTTTC TCTGTGTTCC ACAGGCCGTG GCATGCGGGG ATGGCCATCA CTGCTGCCCA
5581 CGGGGCTTCC ACTGCAGTGC AGACGGGCGA TCCTGCTTCC AAAGATCAGG TGCAGCTGGG
5641 GTGTGGGTGC AGGGCAGGCA GACGGGCAGC ATGTGGAGTC TGGAACCCAG GAGCCCAGCT
5701 GGCGGGGCA GCCCTGATTC CTGCCCTTGT GCCCTCATTC ATGTGGCATC TGTACTAAGC
5761 AACAGCCCTG CTGTGGACAG AGGGGCAGCA CTGGGATAG GAGGGTGCGG GAGAAAGTGC
5821 AAGACTCCAG GTCCAGGCGT TGTGGGGGTG GGGAGAGGTC GAGCTGGGCC GGTCTAATAC
5881 CAACCCATGG TCAGTGGGTG CCCCTTCCCC ATGCCATCTT GCTGAGGGAG GGACTGGATT
5941 GTGAGGAGGG TGAGTTAGGC CTGCCTAGGA GATCACTGAG CCTTAGTGTC ACCCTCAAAC
6001 CCCAGTAGCT GGGCTTGCAG GCCCTGGTGC CACCAGCTCC TTGTGTGATG GGGGAGTCAC
6061 CTTCCCTGAG TGGGCTGGTA GTATCCTGGG TCATCTTGTC CACAGGTAAC AACTCCGTGG
6121 GTGCCATCCA GTGCCCTGAT AGTCAGTTCG AATGCCCGGA CTTCTCCACG TGCTGTGTTA
6181 TGGTCGATGG CTCCTGGGGG TGCTGCCCCA TGCCCCAGGT ACAAATCTGG GGGAGATGGG
6241 GGTATGTGGA GGGAAGTGGG GGCAGAGTTG GGGGCCAGGG GCAGGGGTG AAGACGGAGT
6301 CAGGACCATT TTTTCTCAGG CTTCCTGCTG TGAAGACAGG GTGCACTGCT GTCCGCACGG
6361 TGCCTTCTGC GACCTGGTTC ACACCGCTG CATCACACCC ACGGGCACCC ACCCCCTGGC
6421 AAAGAAGCTC CCTGCCCAGA GGACTAACAG GGCAGGTGAG GAGGTGGGAG AGCATCAGGC
6481 CAGGGGCTGG GGCGGGGCCT CATTGACTCC AAGTGTAGGA AAAGTTTCC TCCATCCTGG
6541 CTGCCCCTCA CGTTTGCTCC TCTTCCAGTG GCCTTGTCCA GCTCGGTCAT GTGTCCGGAC
6601 GCACGGTCCC GGTGCCCTGA TGGTTCTACC TGCTGTGAGC TGCCCAGTGG GAAGTATGGC
6661 TGCTGCCCAA TGCCCAACGT GAGTGAGGGG CTGGAGCCAG CTTGGCTGTG TGCCCCCAGC
6721 CACCTGGCCC TGACACGCAC CTTACAGGGG CTCTGTGGCA TGGGGCTGGC TGGCTGCTTG
6781 CTGGGAGCCT GGCTGATGCA GGGTTCATGC TACCCCCTAG TGGGGGATTG GGGCAGTGCC
6841 AGCCATCAGC CTGGCTGCTC CCTGTGTGCT ACTGAGCCTG GAAGTGACAA AGACCCACCC
```

FIG.51-3

```
6901 CTGTCCCCAC TCAGGCCACC TGCTGCTCCG ATCACCTGCA CTGCTGCCCC CAAGACACTG
6961 TGTGTGACCT GATCCAGAGT AAGTGCCTCT CCAAGGAGAA CGCTACCACG GACCTCCTCA
7021 CTAAGCTGCC TGCGCACACA GGTACCAGAG GCAGGGTGCA GATACAGGGG TGGGGCCCCC
7081 TTTCCTCCCT TTTAGGCCTG GCCTTAGGAT CACTGCAAGG TGGTGTAAGC GGTACCCTCC
7141 ATCTTCAACA CCTGGTTCCA GCTGTGGAGC CGGCAAAGGG TTGATACCCC TGAGGGTCCC
7201 CAGTGCCACT TCTGACCTGT CCTCTCTGCT TCCCTCACAG TGGGGGATGT GAAATGTGAC
7261 ATGGAGGTGA GCTGCCCAGA TGGCTATACC TGCTGCCGTC TACAGTCGGG GGCCTGGGGC
7321 TGCTGCCCTT TTACCCAGGT ACCCAGGGGT GGCGGGTGGG TGGGCTGAGC ACAGTGTGGC
7381 AGGCAGCCGG GCCCCAGTGC CCACCTGCCC TTCTTCATCT GCCCTAGGCT GTGTGCTGTG
7441 AGGACCACAT ACACTGCTGT CCCGCGGGGT TTACGTGTGA CACGCAGAAG GGTACCTGTG
7501 AACAGGGGCC CCACCAGGTG CCCTGGATGG AGAAGGCCCC AGCTCACCTC AGCCTGCCAG
7561 ACCCACAAGC CTTGAAGAGA GATGTCCCCT GTGATAATGT CAGCAGCTGT CCCTCCTCCG
7621 ATACCTGCTG CCAACTCACG TCTGGGGAGT GGGGCTGCTG TCCAATCCCA GAGGTATATG
7681 GGAGGGGACA GCATCTTGGC CTGGGCAGGT GGGTGGCCAA GCTCCTATTG CTTTCTGCCC
7741 TCCGCATAGC CCATAGGTGA TACCCAGCTC TGACAGATTC GTCCCCAGCT GGAGGTGCTG
7801 TAAGCAGGAG AGGCGGGCTG GAGTAGGTAG GGGCTCGGCA CTGCGCCCCA CATAGTGGCT
7861 ACCTACAACG CCCTTTCCTG CCCACCCCCC AGGCTGTCTG CTGCTCGGAC CACCAGCACT
7921 GCTGCCCCCA GGGCTACACG TGTGTAGCTG AGGGGCAGTG TCAGCGAGGA AGCGAGATCG
7981 TGGCTGGACT GGAGAAGATG CCTGCCCGCC GGGCTTCCTT ATCCCACCCC AGAGACATCG
8041 GCTGTGACCA GCACACCAGC TGCCCGGTGG GGCAGACCTG CTGCCCGAGC TGGGTGGGA
8101 GCTGGGCCTG CTGCCAGTTG CCCCATGTGA GTGCCTCCCT GCCTGCCCCT GGATAGGGGA
8161 GCTAAGCCCA GTGAGGGGAC AGGAACATAA TGCCATTCTG TGCTCCCTTC CCCGCCAGGC
8221 TGTGTGCTGC GAGGATCGCC AGCACTGCTG CCCGGCTGGC TACACCTGCA ACGTGAAGGC
8281 TCGATCCTGC GAGAAGGAAG TGGTCTCTGC CCAGCCTGCC ACCTTCCTGG CCCGTAGCCC
8341 TCACGTGGGT GTGAAGGACG TGGAGTGTGG GGAAGGACAC TTCTGCCATG ATAACCAGAC
8401 CTGCTGCCGA GACAACCGAC AGGGCTGGGC CTGCTGTCCC TACCGCCAGG TCAGTGCCAA
8461 CCCCCATCCT GGGGCTGGGT ATGGCCAGGG ACCAGGTCCC ACCTCGTCCA ACCCTCTCGC
8521 CCCCCTCTGA CCATCCAGGG CGTCTGTTGT GCTGATCGGC GCCACTGCTG TCCTGCTGGC
8581 TTCCGCTGCG CAGCCAGGGG TACCAAGTGT TTGCGCAGGG AGGCCCCGCG CTGGGACGCC
8641 CCTTTGAGGG ACCCAGCCTT GAGACAGCTG CTGTGAGGGA CAGTACTGAA GACTCTGCAG
8701 CCCTCGGGAC CCCACTCGGA GGGTGCCCTC TGCTCAGGCC TCCTAGCAC CTCCCCCTAA
8761 CCAAATTCTC CCTGGACCCC ATTCTGAGCT CCCCATCACC ATGGGAGGTG GGGCCTCAAT
8821 CTAAGGCCTT CCCTGTCAGA AGGGGGTTGT GGCAAAAGCC ACATTACAAG CTGCCATCCC
8881 CTCCCCGTTT CAGTGGACCC TGTGGCCAGG TGCTTTTCCC TATCCACAGG GGTGTTTGTG
8941 TGTGTGCGCG TGTGCGTTTC AATAAAGTTT GTACACTTTC
```

PROGRANULIN (PGRN) AND ITS DERIVATIVES FOR DIAGNOSIS AND TREATMENT OF LYSOSOMAL STORAGE DISEASES

CROSS REFERENCE TO RELATED APPLICATIONS

The present application is a National Stage Application claiming the priority of PCT Application No. PCT/US2015/014364 filed Feb. 4, 2015, which in turn, claims priority from U.S. Provisional Application Ser. No. 61/935,541 filed Feb. 4, 2014. Applicants claim the benefits of 35 U.S.C. § 120 as to the PCT Application and priority under 35 U.S.C. § 119 as to the said U.S. Provisional application, and the entire disclosures of both applications are incorporated herein by reference in their entireties.

FIELD OF THE INVENTION

The present invention relates generally to lysosomal storage diseases and their diagnosis and treatment, including Gaucher's Disease, and particularly to diagnostic and therapeutic aspects thereof which utilize progranulin (PGRN), or active PGRN peptides, including atsttrin.

BACKGROUND OF THE INVENTION

Progranulin (PGRN) is a multifunctional growth factor, also known as PC-cell-derived growth factor (PCDGF), acrogranin, Granulin/epithelin precursor (GEP), proepithelin (PEPI), or GP80, and was first purified as a growth factor from conditioned tissue culture media (Wright W E et al (1989) Cell 56(4):607-617; Zhou J et al (1993) J Biol Chem 268(15):10863-10869). PGRN is a 593-amino-acid secreted glycoprotein with an apparent molecular weight of 88 kDa. PGRN contains seven and a half repeats of a cysteine-rich motif $(CX_{5-6}CX_5CCX_8CCX_6CCXDX_2HCCPX_4CX_{5-6}C)$ (SEQ ID NO:1) in the order P-G-F-B-A-C-D-E, where A-G are full repeats and P is the half motif (FIG. 24). Notably, PGRN (GEP) undergoes proteolytic processing with the liberation of small, 6-kDa repeat units known as granulins (or epithelins), which retain biological activity (Davidson B et al (2004) Cancer 100(10):2139-2147)). These peptides are active in cell growth assays and may be related to inflammation (Zanocco-Marani, T et al (1999) Cancer Res 59(20):5331-5340; Lu R and Serrero G (2000) Proc Natl Acad Sci USA 97(8):3993-3998).

PGRN has multiple physiological and pathological functions in development, would healing, anti-inflammation, neuron system disorders, as well as cancer. PGRN (GEP) is abundantly expressed in rapidly cycling epithelial cells, in cells of the immune system, and in neurons (Baba T et al (1993) Mol Reprod Dev 34(3):233-243; Daniel R et al (2000) Histochem Cytochem 48(7):999-1009). High levels of GEP expression are also found in several human cancers and contribute to tumorigenesis in diverse cancers, including breast cancer, clear cell renal carcinoma, invasive ovarian carcinoma, glioblastoma, adipocytic teratoma, and multiple myeloma (Davidson B et al (2004) Cancer 100(10):2139-2147; Bateman A et al (1990) Biochem Biophys Res Comm 173(3):1161-1168; Gonzales E M et al (2003) J Biol Chem 278(40):38113-38116; He A and Bateman A (2003) J Mol Med 81(10):600-612; Jones M B et al (2003) Gynecol Oncol 88(1 pt2):S136-139; Wang W et al (2003) Clin Cancer Res 9(6):2221-2228). Although GEP mainly functions as a secreted growth factor, it was also found to be localized inside cells and to directly modulate intracellular activities (Daniel R et al (2000) Histochem Cytochem 48(7):999-1009; Hoque M et al (2003) Mol Cell Biol 23(5):1688-1702). Mutations of PGRN were found to cause frontotemporal lobular degeneration (FTLD) by two groups at the same time (Baker M et al (2006) Nature 442:916-919; Cruts M et al (2006) Nature 442:920-924). Since the initial FTLD studies, 70 pathogenic mutations of PGRN have been reported (reviewed by van Swieten (Van Sweiten J C et al (2008) Lancet Neurol 7(10):965-974) to cause FTLD.

Several PGRN-associated partners have been reported and found to affect PGRN action in various processes. One example is the secretory leukocyte protease inibitor (SLPI). Elastase digests PGRN exclusively in the intergranulin linkers with the generation of granulin peptides. SLPI blocks this proteolysis either by directly binding to elastase or by sequestering granulin peptides from the enzyme (Zhu J et al (2002) Cell 111(6):867-878). PGRN was also found to bind to Sortilin and mediate neurite growth (Hu F et al (2010) Neuron 68:654-667).

Recently, PGRN and PGRN peptides, particularly including the peptide denoted atsttrin, were identified as modulators of TNF/TNFR activity and signaling, and demonstrated to inhibit or block TNF-mediated signaling or response, including TNF-α-induced inflammatory arthritis (Tang W et al (2011) Science 332:478-484; WO 2010120374). Atsttrin is a PGRN-derived engineered protein (Antagonist of TNF/TNFR Signaling via Targeting TNF Receptors), comprising combinations of half units of PGRN units A, C and F in combination with linker units P3, P4 and P5 (U.S. Pat. No. 8,362,218; WO 2010120374). Atsttrin provides a PGRN-derived active peptide having overlapping activity and capability with the full length PGRN molecule. U.S. Pat. No. 8,362,218 and PCT publication WO 2010120374 describe PGRN-derived peptides comprising a combination of half units of progranin/granulin units, wherein at least one half unit is ½ F, and linker units, particularly at least two linker units. The amino acid sequence of PGRN, and PGRN-derived peptides, including atttstrin, are depicted in FIGS. 49 and 50.

Lysosomal Storage Diseases

Lysosomes are subcellular organelles responsible for the physiologic turnover of cell constituents. They contain catabolic enzymes, which require a low pH environment in order to function optimally. Lysosomal storage diseases (LSD) describe a heterogeneous group of dozens of rare inherited disorders characterized by the accumulation of undigested or partially digested macromolecules, which ultimately results in cellular dysfunction and clinical abnormalities. LSDs result from gene mutations in one or more of lysosomal enzymes, resulting in accumulation of the enzyme substrates in lysosomes. Organomegaly, connective-tissue and ocular pathology, and central nervous system dysfunction may result. Classically, lysosomal storage diseases encompassed enzyme deficiencies of the lysosomal hydrolases. More recently, the concept of lysosomal storage disease has been expanded to include deficiencies or defects in proteins necessary for the normal post-translational modification of lysosomal enzymes, activator proteins, or proteins important for proper intracellular trafficking between the lysosome and other intracellular compartments.

Over 50 lysosomal storage diseases have been described. The age of onset and clinical manifestations may vary widely among patients with a given lysosomal storage disease, and significant phenotypic heterogeneity between family members carrying identical mutations has been reported. Lysosomal storage diseases are generally classified by the accumulated substrate and include the sphingolipidoses, oligosaccharidoses, mucolipidoses, mucopolysaccharidoses (MPSs), lipoprotein storage disorders, lysosomal transport defects, neuronal ceroid lipofuscinoses and others. FIG. 1 depicts pathways for glycosphingolipids and indicates the altered metabolic enzymes associated with different lysosomal storage diseases.

The most common of the LSDs is Gaucher's Disease, which involves dysfunctional metabolism of sphingolipids and results from hereditary deficiency of the enzyme glucocerebrosidase. Glucocerebrosidase enzyme acts on the fatty acid glucosylceramide and when the enzyme is defective, glucosylceramide accumulates particularly in white blood cells, most often macrophages. Over 300 unique mutations of the glycocerebrosidase encoding gene GBA1 have been identified in Gaucher's Disease (Beutler E and Grabowski G A (2001) Gaucher Disease. in The Metabolic and Molecular Basis of Inherited Disease CR Scriver et al eds. McGraw Hill, N.Y. pp3635-3668; Grabowski G A (2008) Lancet 372(9645):1263-1271; Zhao et al (2003) Clin Genet 64(1):57-64). Glucosylceramide can collect in the spleen, liver, kidneys, lungs, brain and bone marrow.

Gaucher's Disease (GD) falls into three subtypes, with varying pathology and severity. Type I (or non-neuropathic type) is the most common form of the disease, with an incidence of 1 in 50,000 live births of Ashkenazi Jewish heritage. Type I patients have hepatosplenomegaly. The brain is generally not affected pathologically, and depending on disease onset and severity, type 1 patients may live well into adulthood. Many patients have a mild form of the disease or may not show any symptoms. Type I is associated genetically with a GBA1 gene mutation N370S homozygote. Type II (or acute infantile neuropathic Gaucher's disease), begins within 6 months of birth and has an incidence rate of approximately 1 in 100,000 live births. Type II patients have an enlarged liver and spleen, extensive and progressive brain damage, eye movement disorders, spasticity, seizures, limb rigidity, and a poor ability to suck and swallow. Type II patients suffer from serious convulsions, hypertonia, mental retardation and apnea. Affected children usually die by age 2. Type II GD is associated with GBA1 mutation alleles including GBA1 mutation L444P. Type III GD, a chronic neuropathic form, can begin at any time in childhood or even in adulthood, and occurs in approximately 1 in 100,000 live births. It is characterized by slowly progressive but milder neurologic symptoms compared to the acute or type II GD. Major symptoms include an enlarged spleen and/or liver, seizures, poor coordination, skeletal irregularities, eye movement disorders, blood disorders including anemia and respiratory problems. Type III patients suffer from muscle twitches known as myoclonus, convulsions, dementia and ocular muscle apraxia. Patients often live into their early teen years and adulthood. The genetics and any specific GBA1 mutations associated with Type III GD are not clear.

Diagnostic indicators for Gaucher's Disease include increased alkaline phosphatase (ALP), angiotensin-converting enzyme (ACE) and immunoglobulin levels. Alternatively or in addition, cell analysis showing "crinkled paper" cytoplasm and glycolipid-laden macrophages, which are also called "Gaucher's cells" are cellular hallmarks of GD. Mutations in the GBA1 gene are also evaluated, particularly those known to be associated with the disease and Types as noted above. GBA1 mutational analysis can be valuable particularly in families at risk of GD due to family history or that are carriers of GBA1 mutations.

Therapy for LSDs includes enzyme replacement therapy to replace the disease mutant enzyme. Enzyme replacement therapy (ERT) and substrate reduction therapy (SRT) may be applicable for peripheral manifestations in patients with Gaucher disease types I and III, Fabry disease, mucopolysaccharidosis I (Hurler, Hurler-Scheie, and Scheie syndromes), mucopolysaccharidosis II (Hunter syndrome), mucopolysaccharidosis VI (Maroteaux-Lamy syndrome), and Pompe disease. Efforts are underway to develop enzyme replacement options for several other disorders. TABLE 1 provides ERTs being evaluated or approved for treatment of certain LSDs. Exemplary therapies, including ERT, for Gaucher's Disease are listed in TABLE 2. Thus far, ERT has been largely unsuccessful in improving central nervous system manifestations of the lysosomal storage diseases, possibly due to difficulty in penetrating the blood-brain barrier. This has led to active clinical trials evaluating the safety and efficacy of intrathecal enzyme delivery in several lysosomal storage diseases. Also, immune response to enzyme replacement therepay proteins has been reported and can have adverse effects and alter the safety and efficacy of ERT (Brooks D A (1999) Molec Genet Metab 68(2):268-275).

TABLE 1

Enzyme Replacement Therapy (ERT) for Lysosomal Storage Diseases (LSD)

| Disease | Enzyme replaced | Company | Status |
| --- | --- | --- | --- |
| Gaucher, type 1 and type 3 | Glucocerebrosidase | Genzyme | approved EU/US (1991) |
| Fabry | α-galactosidase A | Genzyme | approved EU (2001) |
| | | | approved US (2003) |
| | | Transkaryotic Therapies | approved EU (2001) |
| MPS I (Hurler) | α-L-iduronidase | BioMarin Pharmaceutical/ Genzyme | approved EU/US (2003) |
| MPS IV (Maroteaux-Lamy) | arylsulfatase B | BioMarin Pharmaceutical | approved US (2005) |
| Pompe | α-glucosidase | Genzyme | phase III clinical trial |
| MPS II (Hunter) | α-L-iduronate sulfatase | Transkaryotic Therapies | phase III clinical trial |
| Niemann-Pick B | acid sphingomylinase | Genzyme | preclinical |
| Metachromatic leukodystrophy | arylsulfatase A | Zymenex | preclinical |
| α-Mannosidosis | 1183α-mannosidase | Zymenex | preclinical |

TABLE 2

Therapies including ERT in Gaucher Diseases

| Agent | Mechanism | Manufacturer | Status |
| --- | --- | --- | --- |
| Imiglucerase (ERT) | Rh GBA1 | Genzyme Corporation | FDA approved |
| Velaglucerase alfa (ERT) | Rh GBA1 | Shire plc | FDA approved |
| Taliglucerase alpha (ERT) | Plant-derived GBA1 | Protalix and Pfizer | FDA approved |
| Miglusta (SRT) | Inhibits glucosylceramide synthase | Actelion | Under development |

TABLE 2-continued

Therapies including ERT in Gaucher Diseases

| Agent | Mechanism | Manufacturer | Status |
|---|---|---|---|
| Isofagomine tartrate (PCT) | Chaperoning, facilitates GBA folding and trafficking | Amicus Therapeutics | Under development |

Therefore, in view of the aforementioned deficiencies attendant with prior art methods of evaluating, ameliorating and treating lysosomal storage diseases, including Gaucher's Disease, it should be apparent that there still exists a need in the art for alternative therapies, additional agents, and improved and more correlative diagnostics for lysosomal storage diseases, including Gaucher's Disease. The present invention provides novel activity, use and application of progranulin (PGRN) and peptide derivatives thereof including atsttrin, including in diagnosis, amelioration, and treatment of lysosomal storage diseases, including Gaucher's Disease.

The citation of references herein shall not be construed as an admission that such is prior art to the present invention.

SUMMARY OF THE INVENTION

In accordance with the present invention, it has been discovered that mutations in the gene encoding progranulin (PGRN), including the absence of PGRN by gene knockout, leads to Gaucher's disease, a genetic disease previously known to be only caused by or associated with glycocerebrosidase enzyme gene (GBA1) mutations. Thus, PGRN and its encoding gene provides a novel gene associated with and capable of generating GD in an animal, in addition to or instead of the glycocerebrosidase GBA1 gene. The examples and studies provided herein demonstrate that PGRN knockout (KO) (null mutant) mice develop Gaucher's disease, including the classical pathological appearance of Gaucher cells, which is diagnostic of lysosome storage disorders under the electronic microscope. Lipid analysis of PGRN KO mice shows glycocerebrosidase enzyme substrate glucosylceramide, denoted β-GlcCer, accumulation in macrophages.

The examples and studies provided herein demonstrate that PGRN binds glycocerebrosidase (GBA1), and the delivery of the GBA1 enzyme to the lysosome is impaired in PGRN KO mice. A clinical drug used to treat Gaucher's disease imuglucerase rescues the Gaucher's disease phenotype in PGRN KO mice.

Also, 15% Gaucher's disease patients have a significantly reduced level of PGRN protein and over 70% of GD patients have a PGRN gene mutation. These findings reveal that PGRN has an important function in the lysosome and trafficking of proteins to the lysosome, and that mutation of the PGRN gene is associated with lysisimal storage disease (LSD). PGRN, or PGRN-derived peptides including atsttrin, provide novel protein therapeutics for prophylaxis and treatment of LSDs, including Gaucher's Disease.

The invention provides PGRN and PGRN peptides, particularly including the peptide(s) denoted atsttrin, as modulators of lysosomal storage disease and of lysosomal trafficking. In particular, the invention provides PGRN and PGRN peptides, including atsttrin, as facilitators of lysosomal enzyme trafficking to the lysosome. In a particular embodiment, the present invention relates to all members of the herein disclosed family of PGRN peptides and of atsttrin, which are capable of facilitating enzyme delivery to the lysosome, and/or binding or complexing with lysosomal enzymes such as glycocerebrosidase (GBA), or with sortilin and/or HSP70. The family of peptides includes fragments or portions, including mixed portions of PGRN sequence and half units, particularly comprising one or more granulin unit and one or more linker unit of PGRN. In one aspect the peptide comprises two or more half units of granulin units and one or more linker unit of PGRN. In a particular aspect of the invention, the PGRN peptide comprises the peptide atsttrin, comprising combinations of half units of granulin units A, C and F in combination with linker units P3, P4 and P5. In a particular aspect, the GEP peptide comprises a combination of half units of granulin units, wherein at least one half unit is ½ F, and linker units, particularly at least two linker units. In a further particular aspect atsttrin has the amino acid sequence set out in FIG. 50 (SEQ ID NO: 4) and comprises granulin units and linker units ½F-P3-P4-½A-P5-½ C, including as set out herein.

It is an object of the present invention to provide pharmaceutical compositions for use in therapeutic methods which comprise or are based upon the PGRN peptides and/or atsttrin. It is an object of the present invention to provide pharmaceutical compositions for use in therapeutic methods which comprise or are based upon the PGRN peptides and/or atsttrin, including comprising the peptide sequences set out in any of SEQ ID NOs: 2, 3 and 4-9, particularly comprising SEQ ID NO: 2, 3, 4. The pharmaceutical compositions include combinations of one or more PGRN peptides and/or atsttrin which are capable of facilitating enzyme delivery to the lysosome, and/or binding or complexing with lysosomal enzymes such as glycocerebrosidase (GBA), or with sortilin and/or HSP70, and/or capable of reducing lysosomal substrate accumulation, such as β-GlcCer, in the lysosome or macrophage. The pharmaceutical compositions include combinations of one or more PGRN peptides and/or atsttrin having activity as provided herein and one or more lysosomal enzyme or lysosomal substrate reducing agent. Lysosomal enzymes or lysosomal substrate reducing agents include and may be selected from one or more of glucocerebrosidase, α-galactosidase, β-galactosidase, β-hexosaminidase and sphingomyelinase. The pharmaceutical compositions include combinations of one or more PGRN peptides and/or atsttrin having GBA binding activity and one or more of Imiglucerase, Velaglucerase alfa, Taliglucerase alpha, Miglusta and Isofagomine tartrate.

Thus, the invention provides a composition for treatment or alleviation of a lysosomal storage disease comprising isolated PGRN, or active fragments thereof including atsttrin, wherein said PGRN or active fragment comprises an amino acid sequence as set out in any of FIG. 49 or 50, including as set out in any of SEQ ID NOS: 2, 3 and 4-9. The composition may further comprising an enzyme replacement therapy agent or substrate reduction therapy agent for a lysosomal storage disease, including one or more of glucocerebrosidase, α-galactosidase, β-galactosidase, β-hexosaminidase and sphingomyelinase. In one such aspect, the invention provides a composition comprising PGRN or atsttrin in combination with glucocerebrosidase for treatment or alleviation of Gaucher's Disease. In an aspect, compositions of the invention may further comprise one or more molecular chaperone or lysosomal delivery protein, including HSP70 and/or sortilin. Compositions of the invention include pharmaceutical compositions further comprising a pharmaceutically acceptable carrier, vehicle, diluent or excipient.

In a further embodiment, the present invention relates to certain therapeutic methods which would be based upon the activity of PGRN, PGRN peptides and/or atsttrin, or active fragments thereof, in facilitating enzyme delivery to the lysosome, and/or binding or complexing with lysosomal enzymes such as glycocerebrosidase (GBA), or with sortilin and/or HSP70, and/or being capable of reducing lysosomal substrate accumulation, such as β-GlcCer, in the lysosome or macrophage.

Thus, the present invention provides methods for facilitating lysosomal delivery of a protein or enzyme in an animal comprising administering to said animal isolated PGRN, or active fragments thereof including atsttrin. In an aspect thereof said PGRN or active fragment comprises an amino acid sequence as set out in any of FIG. 49 or 50, including comprising or as set out in any of SEQ ID NOS: 2, 3 and 4-9. In an aspect of the invention, a method is provided for facilitating delivery of glycocerebrisidase (GBA) in a patient with Gaucher's Disease comprising administering to said patient isolated PGRN, or active fragments thereof including atsttrin, wherein said PGRN or active fragment comprises an amino acid sequence as set out in any of FIG. 49 or 50, including comprising or as set out in any of SEQ ID NOS: 2, 3 and 4-9.

The invention provides methods for treating or alleviating a lysosomal storage disease in an animal comprising administering to said animal isolated PGRN, or active fragments thereof including atsttrin, wherein said PGRN or active fragment comprises an amino acid sequence as set out in any of FIG. 49 or 50. The invention provides methods for treating or alleviating a lysosomal storage disease in an animal comprising administering to said animal isolated PGRN, or active fragments thereof including atsttrin, wherein said PGRN or active fragment comprises an amino acid sequence including comprising or as set out in any of SEQ ID NOS: 2, 3 and 4-9. In an aspect of these methods, the method comprises additionally administering one or more lysosomal enzyme which is reduced, absent, mutated or altered in the lysosomal storage disease. The lysosomal enzyme may be selected from one or more of a glucocerebrosidase, α-galactosidase, β-galactosidase, β-hexosaminidase and sphingomyelinase.

The lysosomal storage disease of the methods of the invention may be selected from Gaucher's Disease (GD), Tay-Sachs disease, Fabry disease, Farber disease, Sandhoff disease, $G_{M1}$ gangliosidosis, Krabbe disease, Niemann-Pick Disease (Type A, Type B, Type C), Pompe disease, mucolipidosis Type II (Hunter syndrome), mucolipidosis Type IIIA, infantile free sialic acid storage disease (ISSD), lysosomal acid lipase deficiency, Juvenile Hexosaminidase A deficiency, Wollman disease and Salla disease. In an aspect, the lysosomal storage disease of the methods of the invention may be selected from Gaucher's disease (GD), Tay-sachs disease (TSD), mucolipidosis (ML), mucopolysaccharidosis (MPS), metachromatic leukodystrophy (MLD), Farber disease (FD) and Krabbe disease (KD). In one aspect, the lysosomal storage disease of the methods of the invention may be selected from Gaucher's disease (GD) including GD Type I, II or III, Tay-Sachs disease (TSD), mucolipidosis (ML) including ML III, mucopolysaccharidosis (MPS) including MPS II, III, VI, metachromatic leukodystrophy (MLD), Farber disease (FD) and Krabbe disease (KD). In a particular preferred aspect of the methods of the invention, the lysosomal storage disease (LSD) is Gaucher's Disease (GD). In an aspect of the methods of the invention, the method comprise additionally administering the lysosmal enzyme glycerbrisidase (GBA) or an active fragment or recombinant form thereof for treating or alleviating Gaucher's Disease. In a particular preferred aspect of the methods of the invention, the lysosomal storage disease (LSD) is Tay-Sachs disease.

The present invention provides methods and assays for diagnosing or evaluating lysosomal storage disease in an animal comprising determining the expression or activity of PGRN or detecting one or more mutation in the genomic DNA or gene encoding PGRN in said animal.

Any such methods or assays may comprise additionally determining the expression or activity of one or more lysosomal enzyme or detecting one or more mutation in the genomic DNA or gene encoding one or more lysosomal enzyme in said animal. In a particular aspect, a method or assay is provided for diagnosing or evaluating Gaucher's disease in an animal. In this aspect, the method or assay may comprise additionally determining the expression or activity of GBA or detecting one or more mutation in the genomic DNA or gene encoding GBA in said animal.

In accordance with the present invention, it has now been recognized and determined that lysosomal storage disease patients may and indeed often carry PGRN gene or protein mutations. Particularly prevalent PGRN gene variations include four SNP sites rs4792937, rs850713, rs78403836, rs5848, and three point mutatiions, p.C315S, p,E316Q, and p.P365A. Diagnostic methods and assays of the invention include particularly wherein one or more of the PGRN mutations provided herein are assessed or determined. Methods, assays and kits are provided wherein one or more PGRN mutation selected from rs4792937, rs850713, rs78403836, rs5848, and three point mutatiions, p.C315S, p,E316Q, and p.P365A. is determined.

Particular such methods or kits, are wherein one or more PGRN mutation selected from rs4792937, rs850713, rs78403836, rs5848 is determined. In an aspect of the invention, the 4 PGRN SNP sites are determined by Taqman genotyping methods. In one such aspect, the methods or kits utilize exemplary primers including: rs4792937 forward primer, 5'-TGTCCTGGAAACCATCCTTC-3' (SEQ ID NO: 11), reverse primer 5'-CTCCCAAAGCGATTCTCCTA-3' (SEQ ID NO: 12), and Taqman tag sequence 5'-TCAGTAGCTCACA[T/C]TTGTAA-3'(SEQ ID NO: 13); rs850713 forward primer 5'-CCTTCCCTGAGTGGGCTGGTA-3' (SEQ ID NO: 14), reverse primer 5'-AGTGCACCCTGTCTTCACAGC-3'(SEQ ID NO: 15), and Taqman tag sequence 5'-AGGTACAAATCTGGGGGAGATGGGG[A/G]TATGTGGAGGGAAGTGGG GGCAGAG-3' (SEQ ID NO: 16); rs78403836 forward primer 5'-CTGTCCTCTCCCATGGCTAC-3' (SEQ ID NO: 17), reverse primer 5'-GCGGACCTGTAAGCATGAAT-3' (SEQ ID NO: 18), and Taqman tag sequence 5'-AGGAAGAC[G/C]TGATTTT-3' (SEQ ID NO: 19); rs5848 forward primer 5'-CCAGGGGTACCAAGTGTTTG-3' (SEQ ID NO: 20), reverse primer 5'-CACAGGGTCCACTGAAACG-3' (SEQ ID NO: 21), and Taqman tag sequence TCTGCTCAGGCCTCCCTAGCACCTC[C/T]CCCTAACCAAATTCTCCCTGGACCC (SEQ ID NO: 22). Point mutations of p.C315S, p,E316Q, and p.P365A may be amplified by recognized methods, including PCR, and may utilize exemplary primers including the forward primer 5'-GGTGGTGTAAGCGGTACCCT-3' (SEQ ID NO: 23), reverse primer 5'-ACCTGCCCAGGCCAAGATGC-3' (SEQ ID NO: 24), followed by sequencing.

The invention includes kits for diagnosing or evaluating lysosomal storage disease in an animal by detecting the presence or activity and amount of PGRN comprising: (a) a predetermined amount of a detectably labelled specific binding partner of or antibody directed against PGRN; (b) other reagents; and (c) directions for use of said kit.

In an aspect, the invention includes kits for diagnosing or evaluating lysosomal storage disease in an animal by detecting the presence of a PGRN mutation in said animal comprising: (a) one or more nucleic acid probe or primer specific for or directed against the PGRN gene or encoding DNA; (b) other reagents; and (c) directions for use of said kit. An aspect of the kits is provided wherein one or more nucleic acid primer or probe is specific for or suitable for detection or determination of one or more of PGRN mutations rs4792937, rs850713, rs78403836, rs5848, and point mutations, p.C315S, p.E316Q, and p.P365A.

A kit of the invention may further comprise a detectably labelled specific binding partner of or antibody directed against GBA or one or more nucleic acid probe or primer specific for or directed against the GBA gene or encoding DNA.

In an assay, diagnostic method or kit of the invention, a control quantity of the PGRN, PGRN peptides, atsttrin, GBA, or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached. In the instance where a radioactive label, such as the isotopes $^{3}$H, $^{14}$C, $^{32}$P, $^{35}$S, $^{36}$Cl, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention provides an animal model for Gaucher's Disease wherein the animal comprises altered PGRN, wherein PGRN is null, absent or mutated and lysosomal substrate β-GlcCer is increased in macrophages. The animal model may additionally comprise a GBA mutation associated with Gaucher's Disease or wherein GBA is null or absent.

The invention includes an assay system for screening of potential drugs or compounds effective to modulate lysosomal enzyme trafficking and/or lysosomal substrate accumulation by mimicking the activity of PGRN or the PGRN peptides. This aspect includes assays to screen for additional active PGRN fragments, granulin/linker unit combinations, derivatives, variants and amino acid modifications effective to modulate lysosomal enzyme trafficking and/or lysosomal substrate accumulation in a like manner to PGRN and atsttrin peptide. In one instance, the test drug or compound is administered to a cellular sample with GBA, to determine the effect of the test drug or compound upon β-GlcCer accumulation, by comparison with a control, including wherein the control is PGRN, active PGRN peptide(s), atsttrin.

Other objects and advantages will become apparent to those skilled in the art from a review of the following description which proceeds with reference to the following illustrative drawings.

BRIEF DESCRIPTION OF THE DRAWINGS

FIGS. 49A and 49B depict the amino acid sequence of (A) human PGRN (SEQ ID NO: 2) and (B) mouse PGRN (SEQ ID NO: 3). In (B), the granulin units GrnA, GrnC, GrnD and GrnE are underlined and indicated at each unit.

FIG. 50 depicts the sequence of atsttrin peptide (½F+P3+P4+½A+P5+½C) (SEQ ID NO: 4), and sequences of various other PGRN peptides (SEQ ID NOS: 5-9).

FIG. 51 provides the 8 kb PGRN human gene nucleic acid sequence (SEQ ID NO: 10). PGRN mRNA starts at nucleotide 101.

DETAILED DESCRIPTION

Figure 1:
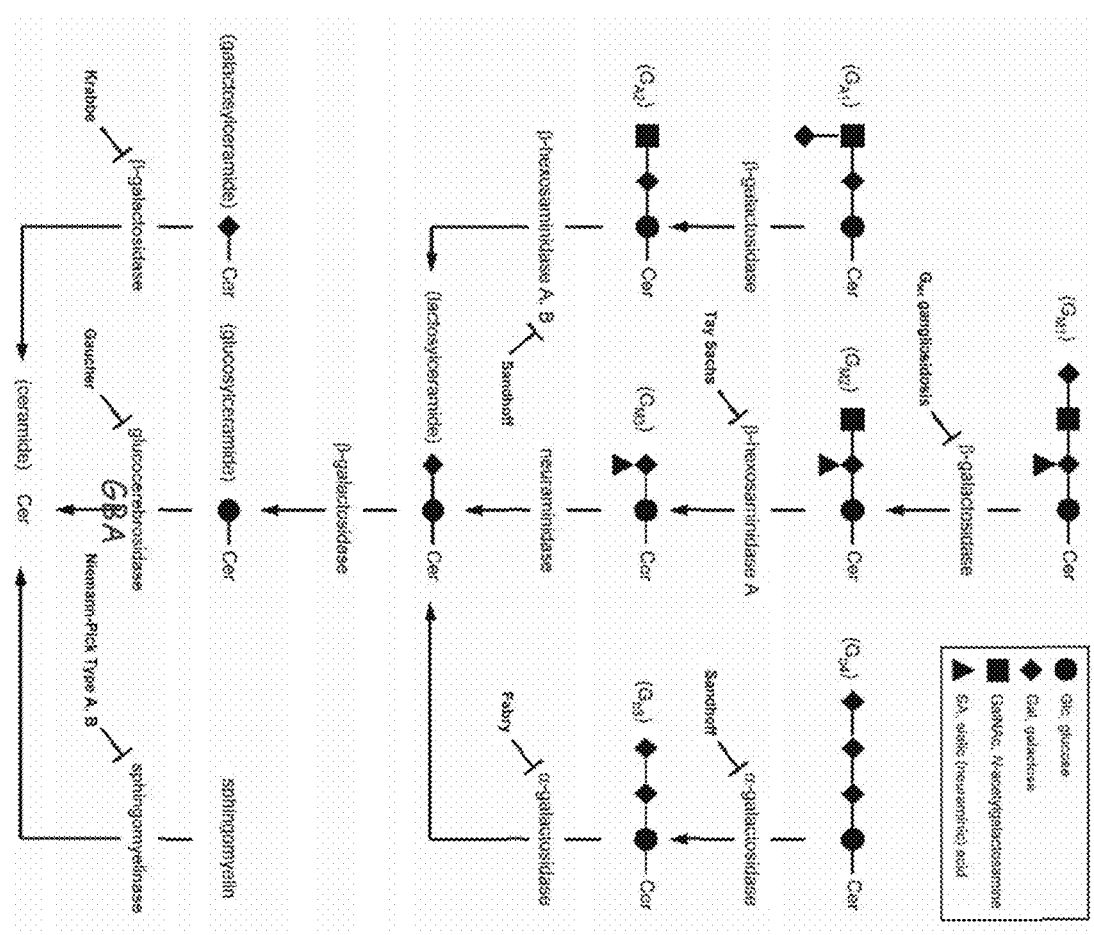
FIG. 1 depicts pathways for glycosphingolipids implicated in lysosomal storage diseases (LSD). Glycosphingolipid metabolism is a process mediated by multiple enzymes. Enzyme insufficiency causes accumulation of the corresponding substrate in lysosomes. Gaucher's disease, the most common LSD, is caused by mutation of glucocerebrosidase (GBA). Mutation of GBA leads to the accumulation of the GBA substrate, β-glucosylceramide (β-GlcCer), in macrophages.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "progranulin", "PGRN", "granulin-epithelin precursor", "GEP", "PC-cell-derived growth factor", "PCDGF", "proepithelin", "acrogranin", and "GP80" and any variants not specifically listed, may be used herein interchangeably, and as used throughout the present application and claims refer to proteinaceous material including single or multiple proteins, and active fragments thereof and extends to those proteins having the amino acid sequence data described herein and presented in FIG. 49, including as set out in SEQ ID NO: 2 and SEQ ID NO: 3, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "progranulin", "PGRN", "granulin-epithelin precursor", "GEP", "PC-cell-derived growth factor", "PCDGF", "proepithelin", "acrogranin", and "GP80" are intended to include within their scope proteins specifically recited herein as well as all substantially homologous analogs and allelic variations.

The terms "granulin(s)", "epithelins" or any of "Granulins A-E", "GrnA", "GrnB", "GrnC", "GrnD", "GrnE" refer to particular cysteine rich motifs, of approximately 6 kDa in size, including comprising or having the sequence motif $CX_{5-6}CX_5CCX_8CCX_6CCXDX_2HCCPX_4CX_{5-6}C$ (SEQ ID NO: 1), which granulins can be released by proteolytic processing from the GEP polypeptide molecule. These granulin(s) may retain biological activity and be active in activity assays, including in cell growth assays, enzyme substrate accumulation assays, protein binding including GBA, sortilin and/or HSP70 binding, GBA and/or other lysosomal enzyme processing or delivery to the lysosome, and assessment for Gaucher type cells. The granulins can provide active fragments of PGRN. Exemplary granulin sequences include those proteins having the amino acid sequence data described herein and presented in FIG. 49 or 50 or fragments thereof, and the profile of activities set forth herein. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "granulin(s)", "epithelins" or any of "Granulins A-E", "GrnA", "GrnB", "GrnC", "GrnD", "GrnE" are intended to include within their scope proteins specifically recited herein as well as all substantially homologous analogs and allelic variations.

Figure 48:
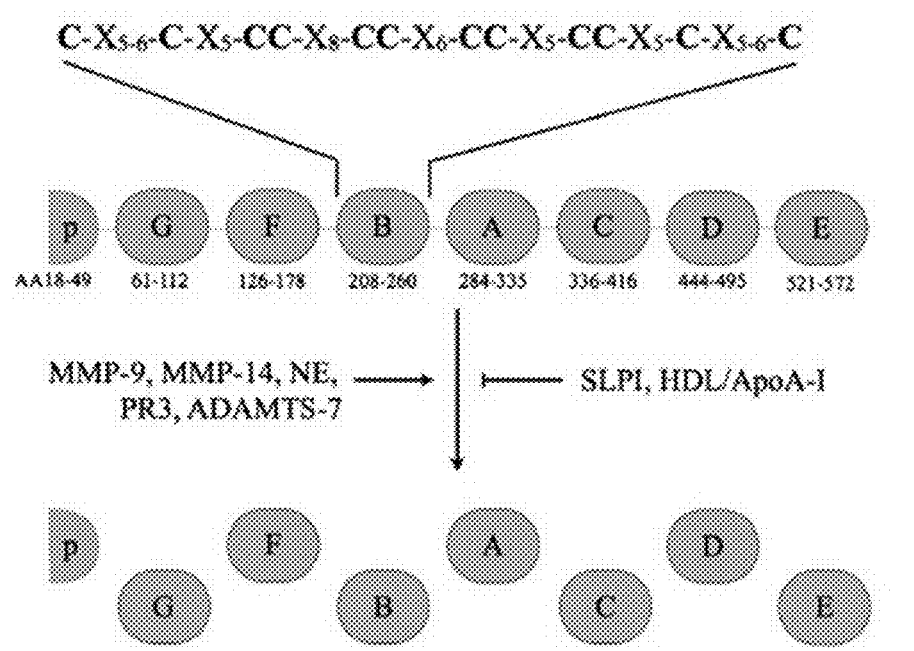
FIG. 48 depicts PGRN protein structure with the Granulin units denoted.

The terms "Atsttrin", "Antagonist of TNF/TNFR Signaling via Targeting TNF Receptors", "atsttrin peptide" and any variants not specifically listed, may be used herein interchangeably, and as used throughout the present application and claims refer to peptides including single or multiple proteins, particularly which are derived from or fragments of PGRN and extends to those proteins having the amino acid sequence data described herein and presented in FIG. 50 and also diagrammed in FIG. 48, and as set out in SEQ ID NO: 4, and the profile of activities and capabilities described and set forth herein and provided in the Claims. Active PGRN peptides having activity in facilitating enzyme delivery to the lysosome, and/or binding or complexing with lysosomal enzymes such as glycocerebrosidase (GBA), or with sortilin and/or HSP70, are included and provided herein. These active PGRN peptides may retain biological activity and be active in activity assays, including in cell growth assays, enzyme substrate accumulation assays, protein binding including GBA, sortilin and/or HSP70 binding, GBA and/or other lysosomal enzyme processing or delivery to the lysosome, and assessment for Gaucher type cells. The full length sequence of human PGRN and of mouse PGRN is provided in FIGS. 49A and 49B respectively (SEQ ID NO: 2 and 3). Thus, lysosomal enzyme binding peptides, including GBA-binding peptides, derived from PGRN sequences(s) or comprising PGRN sequence(s), particularly including Atsttrin or atsttrin derived sequences, and having activity in binding to and/or facilitating delivery of enzymes to the lysosome are encompassed herein. These atsttrin peptides include and encompass fragments, variants, and derivatives of the peptides. Accordingly, proteins displaying substantially equivalent activity, and which are modifications thereof, are likewise contemplated. These modifications may be deliberate, for example, such as modifications obtained through site-directed mutagenesis, or may be accidental, such as those obtained through mutations in hosts that are producers of the complex or its named subunits. Corresponding mouse or other species or ortholog PGRN sequences to the human atsttrin and active PGRN peptide sequences are further contemplated. Also, the terms "Atsttrin", "Antagonist of TNF/TNFR Signaling via Targeting TNF Receptors", "atsttrin peptide", are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |

-continued

| TABLE OF CORRESPONDENCE | | |
|---|---|---|
| SYMBOL | | |
| 1-Letter | 3-Letter | AMINO ACID |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding PGRN (including SEQ ID NO: 10), PGRN-derived peptide Atsttrin, or other PGRN peptide, including or comprising one or more granulin, which code for a peptide having the same amino acid sequence as PGRN or a PGRN peptide, including as set out in any of the FIG. 49 or 50 and SEQ ID NOs: 2, 3 and 4-9 associated therewith, but which are degenerate to any such sequences. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |

| | |
|---|---|
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in the PGRN, PGRN-derived peptide Atsttrin, or PGRN peptide(s) sequence(s) such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids, based on their R groups: Amino acids with nonpolar R groups: Alanine, Valine, Leucine, Isoleucine, Proline, Phenylalanine, Tryptophan, Methionine; Amino acids with uncharged polar R groups: Glycine, Serine, Threonine, Cysteine, Tyrosine, Asparagine, Glutamine; Amino acids with charged polar R groups (negatively charged at Ph 6.0): Aspartic acid, Glutamic acid; Basic amino acids (positively charged at pH 6.0): Lysine, Arginine, Histidine (at pH 6.0). Another grouping may be those amino acids with phenyl groups: Phenylalanine, Tryptophan, and Tyrosine. Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^N$C below the predicted or determined $T_m$ with washes of higher stringency, if desired.

As used herein, "pg" means picogram, "ng" means nanogram, "ug" or "µg" mean microgram, "mg" means milligram, "ul" or "µl" mean microliter, "ml" means milliliter, "l" means liter.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein. Fab and F(ab')$_2$ portions of antibody molecules are prepared by the proteolytic reaction of papain and pepsin, respectively, on substantially intact antibody molecules by methods that are well-known. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The term "therapeutically effective amount" means that amount of a drug, compound, peptide, or pharmaceutical agent that will elicit the biological, physiological, clinical, or medical response of a subject that is being sought by a medical doctor or other clinician. The phrase "therapeutically effective amount" is used herein to include an amount sufficient to prevent, and preferably reduce by at least about 30 percent, more preferably by at least 50 percent, most preferably by at least 90 percent, a clinically significant change in the S phase activity of a target cellular mass, in the enlargement of an organ, in the accumulation of a substrate or protein, in a neurological deficit or impairment, or other feature of pathology such as for example, elevated blood pressure, fever or white cell count, enlargement of the spleen or liver as may attend its presence and activity.

The term "preventing" or "prevention" refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term "prophylaxis" is related to and encompassed in the term "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term "solvate" means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term "subject" includes humans and other mammals.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, 'treating' or 'treatment' relates to slowing the progression of the disease.

The term "lysosomal storage disease(s)", "LSD" refers to a heterogeneous group of diseases or disorders characterized by the accumulation of undigested or partially digested macromolecules, which ultimately results in cellular dysfunction and clinical abnormalities. LSDs result from gene mutations in one or more of lysosomal enzymes, resulting in accumulation of the enzyme substrates in lysosomes, ultimately leading in many instances to organomegaly, connective-tissue and ocular pathology, and central nervous system dysfunction. Lysosomal storage disease(s) include sphingolipidoses, gangliosidosis, mucopolysaccharidoses, glycoprotein storage diseases, mucolipidoses. The term includes, but is not limited to, exemplary diseases selected from Gaucher's Disease (GD), Tay-Sachs disease, Fabry disease, Farber disease, Sandhoff disease, $G_{M1}$ gangliosidosis, Krabbe disease, Niemann-Pick Disease (Type A, Type B, Type C), Pompe disease, mucolipidosis Type II (Hunter syndrome), mucolipidosis Type IIIA, infantile free sialic acid storage disease (ISSD), lysosomal acid lipase deficiency, Juvenile Hexosaminidase A deficiency, Wollman disease and Salla disease. In a particular aspect a preferred lysosomal storage disease is Gaucher's Disease, including Type I, Type II and/or Type III Gaucher's Disease.

The term "Gaucher's Disease", "GD", refers to the most common of the lysosomal storage diseases, Gaucher's Disease. Gaucher's disease involves dysfunctional metabolism of sphingolipids and classically results from hereditary deficiency of the enzyme glucocerebrosidase (GBA).

The present invention demonstrates that the protein Progranulin PGRN plays an important and criticial role in the transport of lysosomal enzymes to the lysosome. As such, PGRN, and PGRN-derived active peptides, including atsttrin, have a therapeutic, prophylactic, and diagnostic use and application in lysosomal storage diseases and disorders. PGRN is demonstrated herein to bind to lysosomal enzymes, including particularly to galactocerebrosidase (GBA). PGRN and particularly PGRN/lysosmal enzyme complexes, such as PGRN/GBA complexes, bind to lysosomal/endosomal trafficking and sorting proteins, including sortilin and HSP70. Lysosomal storage disease, including Gaucher's disease, develops in the absence of PGRN or with mutated PGRN, such as in PGRN knockout (KO) animals. Over 70% of GD patients also have mutations in PGRN. Thus, PGRN and PGRN-derived active peptides including atsrttrin, are applicable for diagnosis, amelioration and therapy in lysosomal storage disease(s), including Gaucher's Disease.

The invention includes use and applications of PGRN, PGRN peptides, atsttrin, and/or active derivatives thereof for prevention, treatment or alleviation of lysosomal storage disease or disorders (LSD). The invention includes use and applications of PGRN, PGRN peptides, atsttrin, and/or derivatives thereof for prevention, treatment or alleviation of lysosomal storage diseases, including conditions, symptoms and clinical manifestations of accumulation of substrates and/or molecules in lysosomes. Lysosomal storage diseases include sphingolipidoses, gangliosidosis, mucopolysaccharidoses, glycoprotein storage diseases, mucolipidoses and exemplary diseases selected from Gaucher's Disease (GD), Tay-Sachs disease, Fabry disease, Farber disease, Sandhoff disease, $G_{M1}$ gangliosidosis, Krabbe disease, Niemann-Pick Disease (Type A, Type B, Type C), Pompe disease, mucolipidosis Type II (Hunter syndrome), mucolipidosis Type IIIA, infantile free sialic acid storage disease (ISSD), lysosomal acid lipase deficiency, Juvenile Hexosaminidase A deficiency, Wollman disease and Salla disease. The invention includes use and applications of GEP, GEP peptides, atsttrin, and/or derivatives thereof for prevention, treatment or alleviation of and/or for specific therapeutic intervention of lysosomal storage disorders by facilitating delivering of required or relevant lysosomal agents, enzymes and/or other molecules to the lysosome.

The possibilities both diagnostic and therapeutic that are raised by the existence of lysosomal protein/enzyme binding peptides, including PGRN, PGRN peptides and/or atsttrin as described herein, derive from the fact that the peptides participate in direct and causal protein-protein interaction with lysosomal protein(s)/enzyme(s), such as glucocerebrosidase (GBA), and serve to initiate, facilitate, mediate or are required for the transport and/or trafficking of lysosomal protein(s)/enzyme(s), such as glucocerebrosidase (GBA), to the lysosyome where they are required for activity to maintain the lysosomal compartment and overall proper and effective protein trafficking and degradation. Thus, the present invention contemplates pharmaceutical intervention in the trafficking and delivery of required enzymes/proteins in and to the lysosome and proper lysosomal function to modulate, alleviate, prevent or treat lysosomal storage diseases or disorders and any other conditions which are associated with altered or insufficient trafficking of proteins and enzymes to the lysosome or endosome.

The invention provides PGRN and PGRN peptides, particularly including the peptide(s) denoted atsttrin, as modulators of lysosomal storage disease and of lysosomal trafficking. In particular, the invention provides PGRN and PGRN peptides, including atsttrin, as facilitators of lysosomal enzyme trafficking to the lysosome. In a particular embodiment, the present invention relates to all members of the herein disclosed family of PGRN peptides and of atsttrin, which are capable of facilitating enzyme delivery to the lysosome, and/or binding or complexing with lysosomal enzymes such as glycocerebrosidase (GBA), or with sortilin and/or HSP70. The family of peptides includes fragments or portions, including mixed portions of PGRN sequence and half units, particularly comprising one or more granulin unit and one or more linker unit of PGRN. In one aspect the peptide comprises two or more half units of granulin units and one or more linker unit of PGRN. In a particular aspect of the invention, the PGRN peptide comprises the peptide atsttrin, comprising combinations of half units of granulin units A, C and F in combination with linker units P3, P4 and P5. In a particular aspect, the GEP peptide comprises a combination of half units of granulin units, wherein at least one half unit is ½ F, and linker units, particularly at least two linker units. In a further particular aspect atsttrin has the amino acid sequence set out in FIG. 50 and SEQ ID NO: 4 and comprises granulin units and linker units ½F-P3-P4-½A-P5-½C, including as set out herein.

It is an object of the present invention to provide pharmaceutical compositions for use in therapeutic methods which comprise or are based upon the PGRN peptides and/or atsttrin. The pharmaceutical compositions include combinations of one or more PGRN peptides and/or atsttrin which are capable of facilitating enzyme delivery to the lysosome, and/or binding or complexing with lysosomal enzymes such as glycocerebrosidase (GBA), or with sortilin and/or HSP70, and/or capable of reducing lysosomal substrate accumulation, such as β-GlcCer, in the lysosome or macrophage. The pharmaceutical compositions include combinations of one or more PGRN peptides and/or atsttrin having activity as provided herein and one or more lysosomal enzyme or lysosomal substrate reducing agent. Lysosomal enzymes or lysosomal substrate reducing agents include and may be selected from one or more of glucocerebrosidase, α-galactosidase, β-galactosidase, β-hexosaminidase and sphingomyelinase. The pharmaceutical compositions include combinations of one or more PGRN peptides and/or atsttrin having GBA binding activity and one or more of Imiglucerase, Velaglucerase alfa, Taliglucerase alpha, Miglusta and Isofagomine tartrate.

Thus, the invention provides a composition for treatment or alleviation of a lysosomal storage disease comprising isolated PGRN, or active fragments thereof including atsttrin, wherein said PGRN or active fragment comprises an amino acid sequence as set out in any of FIG. 49 or 50 and in SEQ ID NOS: 2, 3 or 4-9. In an aspect, the invention provides a composition for treatment or alleviation of a lysosomal storage disease comprising isolated PGRN, wherein said PGRN comprises an amino acid sequence having at least one amino acid substitution, deletion or addition in comparison to the sequence as set out in FIG. 49 and in SEQ ID NOS: 2 and/or 3. Thus, in one aspect the PGRN of use in the invention has at least one amino acid difference versus wild type or natural human or mouse PGRN. In one such aspect, compositions are provided comprising PGRN, a PGRN peptide, or atsttrin in combination with glucocerebrosidase for treatment or alleviation of Gaucher's Disease. In an aspect, compositions of the invention may further comprise one or more molecular chaperone or lysosomal delivery protein, including HSP70 and/or sortilin.

Compositions of the invention include pharmaceutical compositions further comprising a pharmaceutically acceptable carrier, vehicle, diluent or excipient. The PGRN, PGRN peptides and/or atsttrin as described herein, may be prepared in pharmaceutical compositions, with a suitable carrier and at a strength effective for administration by various means to a patient experiencing an adverse medical condition associated with altered or ineffective lysosomal processing or lysosomal enzyme(s), particularly any of a lysosomal storage disease or associated condition, particularly Gaucher's Disease. A variety of administrative techniques may be utilized, among them parenteral techniques such as subcutaneous, intravenous and intraperitoneal injections, catheterizations and the like. Average quantities of the PGRN, PGRN peptides and/or atsttrin as described herein or their subunits may vary and in particular should be based upon the recommendations and prescription of a qualified physician or veterinarian.

The peptides and compositions of the invention include those PGRN peptides, including atsttrin, which are based on the human PGRN sequence, including as set out in FIGS. 49 and 50, including SEQ ID NOS: 2, 3 and 4-9, as well as variants thereof having one or more or a few or many substitutions, wherein the binding and activity profiles of the variant(s) are retained when compared to PGRN, PGRN peptide or the atsttrin peptide. In as much as PGRN peptides from various animals or mammals, including humans, are known, these sequences provide alternative amino acid sequences and variants of potential use in the compositions and methods of the invention, including by substitution of some of the atsttrin human peptide amino acids. Mouse GEP sequence is provided herein in FIG. 49B (SEQ ID NO: 2). PGRN sequences for various animals are publicly known and disclosed and would be available for evaluation and assessment in the methods and compositions of the invention, and their corresponding and correlating amino acids suitable for evaluation and use as variants of the PGRN peptides herein. PGRN sequences are available and herein incorporated by reference as follows: rat (Genbank accession AAA16903.1, CAA44198.1), mouse (Genbank accession P28798.2, BAE35389.1, NP_032201.2), Sumatran orangutan (Genbank accession NP_001126689.1), crab-eating macaque (Genbank accession BAE01796.1), horse (Genbank accession XP_001489791.1), cattle (Genbank accession NP_001070482.1), rabbit (Genbank accession XP_002719228.1), pig (Genbank accession NP_001038043.1), chimpanzee (Genbank accession XP_511549.2) and opossum (Genbank accession XP_001374870.1).

Also, antibodies including both polyclonal and monoclonal antibodies, and drugs that modulate the production or activity of PGRN and/or PGRN peptides and/or their subunits may possess certain diagnostic applications and may for example, be utilized for the purpose of detecting and/or measuring conditions associated with or resulting from altered PGRN, lysosomal storage diseases, Gaucher's disease. For example, the PGRN, atsttrin or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the PGRN of the invention, particularly those which demonstrate binding to lysosomal enzyme, such as binding to GBA, may be discovered or synthesized and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. Panels of monoclonal antibodies produced against PGRN peptides can be screened for various properties; i.e., isotype, epitope, affinity, etc. Of particular interest are monoclonal antibodies that neutralize the activity of the PGRN or its subunits or that bind to GBA. Such monoclonals can be readily identified in binding or activity assays. Preferably, the anti-PGRN antibody used in the diagnostic methods of this invention is an affinity purified polyclonal antibody. More preferably, the antibody is a monoclonal antibody (mAb). In addition, it is preferable for the anti-PGRN antibody molecules used herein be in the form of Fab, Fab', F(ab')$_2$ or F(v) portions of whole antibody molecules.

The invention provides therapeutic methods based upon the activity of PGRN, PGRN peptides and/or atsttrin, or active fragments thereof, in facilitating enzyme delivery to the lysosome, and/or binding or complexing with lysosomal enzymes such as glycocerebrosidase (GBA), or with sortilin and/or HSP70, and/or being capable of reducing lysosomal substrate accumulation, such as β-GlcCer, in the lysosome or macrophage.

Methods are thus provided for facilitating lysosomal delivery of a protein or enzyme in an animal comprising administering to said animal isolated PGRN, or active fragments thereof including atsttrin. In an aspect thereof said PGRN or active fragment comprises an amino acid sequence as set out in any of FIG. 49 or 50, including SEQ ID NOS: 2, 3 and 4-9. Methods include methods for treating or alleviating a lysosomal storage disease in an animal comprising administering to said animal isolated PGRN, or active fragments thereof including atsttrin, wherein said PGRN or active fragment comprises an amino acid sequence as set out in any of FIG. 49 or 50. In an aspect of these methods, the method comprises additionally administering one or more lysosomal enzyme which is reduced, absent, mutated or altered in the lysosomal storage disease. The lysosomal enzyme may be selected from one or more of a glucocerebrosidase, α-galactosidase, β-galactosidase, β-hexosaminidase and sphingomyelinase. The lysosomal storage disease of the methods of the invention may be selected from Gaucher's Disease (GD), Tay-Sachs disease, Fabry disease, Farber disease, Sandhoff disease, $G_{M1}$ gangliosidosis, Krabbe disease, Niemann-Pick Disease (Type A, Type B, Type C), Pompe disease, mucolipidosis Type II (Hunter syndrome), mucolipidosis Type IIIA, infantile free sialic acid storage disease (ISSD), lysosomal acid lipase deficiency, Juvenile Hexosaminidase A deficiency, Wollman disease and Salla disease. In an aspect, the lysosomal storage disease of the methods of the invention may be selected from Gaucher's disease (GD), Tay-sachs disease (TSD), mucolipidosis (ML), mucopolysaccharidosis (MPS), metachromatic leukodystrophy (MLD), Farber disease (FD) and Krabbe disease (KD). In one aspect, the lysosomal storage disease of the methods of the invention may be selected from Gaucher's disease (GD) including GD Type I, II or III, Tay-Sachs disease (TSD), mucolipidosis (ML) including ML III, mucopolysaccharidosis (MPS) including MPS II, III, VI, metachromatic leukodystrophy (MLD), Farber disease (FD) and Krabbe disease (KD). In a particular preferred aspect of the methods of the invention, the lysosomal storage disease (LSD) is Gaucher's Disease (GD). In a particular preferred aspect of the methods of the invention, the lysosomal storage disease (LSD) is Gaucher's Disease (GD). In an aspect of the methods of the invention, the method comprise additionally administering the lysosmal enzyme glycocerebrisidase (GBA) or an active fragment or recombinant form thereof for treating or alleviating Gaucher's Disease. In a particular preferred aspect of the methods of the invention, the lysosomal storage disease (LSD) is Tay-Sachs Disease (TSD).

With regard to the lysosomal storage disease, Gaucher's disease, methods are provided for facilitating delivery of glycocerebrisidase (GBA) in a patient with Gaucher's Disease comprising administering to said patient isolated PGRN, or active fragments thereof including atsttrin. The PGRN or active fragment may particularly comprise an amino acid sequence as set out in any of FIG. 49 or 50, including SEQ ID NOS: 2, 3 and 4-9. For Gaucher's Disease in humans, the human PGRN protein or a peptide thereof may particularly be utilized, and may optionally be combined with recombinant human glucocerebrosidase or GBA, such as imiglucerase.

Methods and assays of the invention include methods and assays for diagnosing or evaluating lysosomal storage disease in an animal comprising determining the expression or activity of PGRN or detecting one or more mutation in the genomic DNA or gene encoding PGRN in said animal. Any such methods or assays may comprise additionally determining the expression or activity of one or more lysosomal enzyme or detecting one or more mutation in the genomic DNA or gene encoding one or more lysosomal enzyme in said animal. A method or assay is provided for diagnosing or evaluating Gaucher's disease in an animal. In this aspect, the method or assay may comprise additionally determining the expression or activity of GBA or detecting one or more mutation in the genomic DNA or gene encoding GBA in said animal.

In accordance with the present invention, it has now been recognized and determined that lysosomal storage disease patients may and indeed often carry PGRN gene or protein mutations. Particularly prevalent PGRN gene mutations include rs4792937, rs850713, rs78403836, rs5848, and three point mutations, p.C315S, p,E316Q, and p.P365A. Diagnostic methods and assays of the invention include particularly wherein one or more of the PGRN mutations provided herein are assessed or determined. Methods, assays and kits are provided wherein one or more PGRN mutation selected from rs4792937, rs850713, rs78403836, rs5848, and three point mutations, p.C315S, p,E316Q, and p.P365 is determined.

Particular such methods or kits, are wherein one or more PGRN mutation selected from rs4792937, rs850713, rs78403836, rs5848 is determined. In an aspect, the 4 PGRN SNP sites are determined by Taqman genotyping methods including the following exemplary primers: rs4792937 forward primer, 5'-TGTCCTGGAAA CCATCCTTC-3' (SEQ ID NO: 11), reverse primer 5'-CTCCCAAAGCGATTCTC-CTA-3' (SEQ ID NO: 12), and Taqman tag sequence 5'-TCAGTAGCTCACA[T/C]TTGTAA-3' (SEQ ID NO: 13); rs850713 forward primer 5'-CCTTCCCT-GAGTGGGCTGGTA-3' (SEQ ID NO: 14), reverse primer 5'-AGTGCACCCTGTCTTCACAG C-3' (SEQ ID NO: 15), and Taqman tag sequence 5'-AGGTA-CAAATCTGGGGGAGATGGGG[A/G]TATGTG-GAGGGAAGTGGG GGCAGAG-3' (SEQ ID NO: 16); rs78403836 forward primer 5'-CTGTCCTCTCCCATGGC-TAC-3' (SEQ ID NO: 17), reverse primer 5'-GCGGACCT-GTAAGCATGAAT-3' (SEQ ID NO: 18), and Tagman tag sequence 5'-AGGAAGAC[G/C]TGATTTT-3' (SEQ ID NO: 19); rs5848 forward primer 5'-CCAGGGGTACCAAGT-GTTTG-3' (SEQ ID NO: 20), reverse primer 5'-CACA-GGGTCCACTGAAACG-3' (SEQ ID NO: 21), and Taqman tag sequence TCTGCTCAGGCCTCCCTAGC ACCTC[C/T]CCCTAACCAAATTCTCCCTGGACCC (SEQ ID NO: 22). In an aspect, point mutations of p.C315S, p,E316Q, and p.P365A are amplified by PCR, and the forward primer 5'-GGTGGTGTAAGCGGTACCCT-3' (SEQ ID NO: 23), reverse primer 5'-ACCTGCCCAGGCCAAGATGC-3' (SEQ ID NO: 24), followed by sequencing.

Kits are provided herein for diagnosing or evaluating lysosomal storage disease in an animal by detecting the presence or activity and amount of PGRN comprising: (a) a predetermined amount of a detectably labelled specific binding partner of or antibody directed against PGRN; (b) other reagents; and (c) directions for use of said kit. Such kits include kits for diagnosing or evaluating lysosomal storage disease in an animal by detecting the presence of a PGRN mutation in said animal comprising: (a) one or more nucleic acid probe or primer specific for or directed against the PGRN gene or encoding DNA; (b) other reagents; and (c) directions for use of said kit. An aspect of the kits is provided wherein one or more nucleic acid primer or probe is specific for or suitable for detection or determination of one or more PRN mutation selected from rs4792937, rs850713, rs78403836, rs5848, and three point mutatiions, p.C315S, p,E316Q, and p.P365A.

A kit of the invention may further comprise a detectably labelled specific binding partner of or antibody directed against GBA or one or more nucleic acid probe or primer specific for or directed against the GBA gene or encoding DNA.

In an assay, diagnostic method or kit of the invention, a control quantity of the PGRN, PGRN peptides, atsttrin, GBA, or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached. In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

As suggested earlier, the diagnostic method of the present invention comprises examining a cellular sample or medium by means of an assay including an effective amount of an antagonist to PGRN protein or a peptide thereof including atsttrin, such as an anti-PGRN antibody, preferably an affinity-purified polyclonal antibody, and more preferably a mAb. In addition, it is preferable for the antibody molecules used herein be in the form of Fab, Fab', F(ab')$_2$ or F(v) portions or whole antibody molecules. As previously discussed, patients capable of benefiting from this method include those suffering from a lysosomal storage disease or Gaucher's disease. Methods for isolating the antibody and inducing anti-PGRN antibodies and for determining and optimizing the ability of anti-PGRN antibodies to assist in the examination and evaluation of the target cells or of clinical samples are all well-known in the art.

The present invention further contemplates therapeutic compositions useful in practicing the therapeutic methods of this invention. A subject therapeutic composition includes, in admixture, a pharmaceutically acceptable excipient (carrier) and one or more of PGRN, polypeptide analog thereof or fragment thereof such as atsttrin, as described herein as an active ingredient.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic PGRN polypeptide, analog such as atsttrin, or active fragment-containing compositions are conventionally administered intravenously, as by injection of a unit dose, for example, but may be administered via any suitable means including IM, IP, IV, orally, transdermally, etc. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and PGRN activity or PGRN-GBA binding capacity desired. Precise amounts of active ingredient required to be administered depend on the judgment of the practitioner and are peculiar to each individual. However, suitable dosages may range from about 0.001 to 1, 0.01 to 10, 0.1 to 20, 0.5 to 50, preferably about 0.5 to about 10, and more preferably one to several, milligrams of active ingredient per kilogram body weight of individual per day and depend on the route of administration. Suitable regimes for initial administration and subsequent administration are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The present invention naturally contemplates several means for preparation of the PGRN, PGRN peptides and/or atsttrin of the present invention, including as illustrated herein and/or using known recombinant techniques, and the invention is accordingly intended to cover such synthetic preparations within its scope. The determination of the amino acid sequences disclosed herein facilitates the reproduction of the peptides by any of various synthetic methods or any known recombinant techniques, and accordingly, the invention extends to expression vectors comprising nucleic acid encoding the peptides of the present invention for expression in host systems by recombinant DNA techniques, and to the resulting transformed hosts.

The present invention also relates to a recombinant DNA molecule, recombinant nucleic acid, or cloned gene, or a degenerate variant thereof, preferably a nucleic acid molecule, in particular a recombinant DNA molecule or cloned gene, encoding the amino acid of one or more PGRN peptides shown in FIG. 49 or 50 or variants thereof. In a particular embodiment, the recombinant DNA molecule, recombinant nucleic acid, or a degenerate variant thereof, preferably a nucleic acid molecule, encodes a PGRN peptide capable of binding GBA, facilitating lysosomal enzyme transport, and/or reducing lysosomal substrate such as β-GlcCer accumulation, which comprises one or more granulin unit and one or more linker unit of PGRN as depicted in FIG. 48 and as set out in the sequence of PGRN, or PGRN peptide, such as atsttrin, for example as in FIGS. 48, 49 and 50, including comprising a sequence as set out in SEQ ID NOS: 2, 3 or 4-9. In a further particular embodiment, the recombinant DNA molecule, recombinant nucleic acid, or a degenerate variant thereof, preferably a nucleic acid molecule, encodes PGRN or a PGRN peptide atsttrin capable of binding GBA, facilitating lysosomal enzyme transport, and/or reducing lysosomal substrate such as β-GlcCer accumulation as set out in FIG. 49 or 50 and comprising granulin units and linker units ½F-P3-P4-½A-P5-½C.

As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B—W and L-M cells, African Green Monkey kidney cells (e.g., COS 1, COS 7, BSC1, BSC40, and BMT10), insect cells (e.g., Sf9), and human cells and plant cells in tissue culture.

One skilled in the art will be able to select the proper vectors, expression control sequences, and hosts without undue experimentation to accomplish the desired expression without departing from the scope of this invention.

Synthetic DNA sequences allow convenient construction of genes which will express PGRN or atsttrin analogs or "muteins". Alternatively, DNA encoding muteins can be made by site-directed mutagenesis of native PGRN genes or cDNAs, and muteins can be made directly using conventional polypeptide synthesis.

In assays and diagnostic kits of the invention, labels may be used. The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The PGRN or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$ $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase.

The generation of animal models for lysosomal storage diseases, including Gaucher's Disease, particularly ones that recapitulate the clinical conditions has proven to be a challenge (Farfel-Becker T et al (2011) Dis Model Mech 4(6):746-752). For GD, many GBA knockouts and null mutations in animals have led to lethality or early death (Sun Y et al (2005) J Lipid Res 46:2102-2113). Animal models have been generated based on known GBA mutations, including L449P, N370S, V394L, D409H and D409V point mutations, which are associated with various common forms of GD, as well as chemically induced models, for example involving administration of a GlcCerase inhibitor (Farfel-Becker T et al (2011) Dis Model Mech 4(6):746-752).

Tay-Sachs disease naturally exists in Jacob sheep and the biochemical mechanism for the disease in Jacob Sheep is virtually identical to that in humans (Torres P A, et al (2010) *Molecular Genetics and Metabolism* 101 (4): 357-363). In Jacob sheep, diminished activity of hexosaminidase A resulting in increased concentrations of GM2 ganglioside in the affected animal sheep has been shown (Porter B F, et al (2011) *Veterinary Pathology* 48 (3): 807-813). The sheep HexA gene is identical in number of nucleotides and has 86% nucleotide identity to the human HexA gene. A missense mutation (G444R) was found in the HEXA cDNA of affected sheep, providing a single nucleotide change at the end of exon 11, resulting in that exon's deletion (before translation) via splicing (Kolodny E, Horak F, Horak J (2011) *ALBC Newsletter* (Pittsboro, N.C., USA: American Livestock Breeds Conservancy). Jacob sheep provide an available animal model for Tay-Sachs disease, however, sheep are not as readily manipulated or housed as smaller animals or those with established recombinant methods protocols, such as mice or rats. Therefore, an alternative model for Tay-Sachs in mice, etc would be very beneficial.

The invention provides new and novel animal models for lysosomal storage diseases, including Gaucher's disease. Animals with altered PGRN or PGRN knock out/null (KO) develop lysosomal storage disease, resembling clinical Gaucher's disease. The animals accumulate the GBA substrate β-GlcCer in lysosomes, develop hepatosplenomegaly, which is a well-documented symptom of Gaucher's disease, and Gaucher cells can be seen histologically. PGRN KO or null mutant animals may be treated with ovalbumin or other agent(s) to generate chronic inflammatory models which have GD and lysosomal storage disease phenoytpes and mimic the disease. Thus, in an aspect of the invention, animal models for GD and/or other lysosomal storage diseases are provided. Exemplary animal models of the invention may be based on knockout or null mutations of PGRN, altered expression or conditional PGRN mutants, rs4792937, rs850713, rs78403836, rs5848, and three point mutations, p.C315S, p,E316Q, and p.P365A. One or more PGRN alteration or mutation may be combined with one or more GBA mutation or alteration, or with a mutation in another lysosomal enzyme, including for example, one or more of an α-galactosidase, β-galactosidase, sphingomyelinase, to generate an animal model of GD or other lysosomal storage disease.

The invention also provides animal models for other lysosomal storage diseases, including Tay-Sachs disease, particularly wherein animals with altered PGRN or PGRN knock out/null animals show physiological or molecular aspects of the lysosomal storage disease. For instance, the examples provided herein demonstrate alterations in HexA and GM2 ganglioside with PGRN KO mice that are hallmarks of Tay-Sachs disease. Animals with altered PGRN or PGRN knock out/null animals, alone or combined with HexA gene mutations or HexA mutants, provide a novel alternative Tay-Sach's disease model.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Progranulin is Required for the Lysosomal Delivery of β-Glucocerebrosidase and its Deficiency Causes Gaucher Disease Glycosphingolipid metabolism is a process mediated by multiple enzymes. Insufficiency of a metabolic enzyme causes accumulation of its corresponding substrate in the lysosome. Pathways for glycosphingolipid metabolism implicated in lysosome storage diseases (LSD) are depicted in FIG. 1. Gaucher's disease, the most common LSD, is caused by mutation of glucocerebrosidase (GBA), which metabolizes β-glucosylceramide to ceramide, as shown in FIG. 1. Mutation of GBA leads to the accumulation of the GBA substrate, β-glucosylceramide (β-GlcCer), in macrophages.

Gaucher disease (GD), the most common lysosomal storage disease, is typically caused by inherited deficiency of glucocerebrosidase (GBA). Herein we report that deficiency of progranulin (PGRN), a growth factor with a unique structure and multiple functions, also causes Gaucher-like disease unexpectedly. Both ovalbumin-challenged and aged PGRN-deficient mice exhibit signs of GD, and relevant tissues are infiltrated with "Gaucher cells", i.e., macrophages that show a characteristic "crinkled paper" cytoplasmic appearance resulting from the accumulation of glucosylceramide. Recombinant PGRN promotes glucosylceramide clearance in PGRN-deficient macrophages and prevents the GD development in PGRN-deficient mice. PGRN binds directly to GBA and is required for the delivery of GBA to lysosome. Unbiased Mass Spectrometry approaches identify heat shock protein 70 (HSP70), an evolutionarily conserved molecular chaperone, as a GBA-associated protein that mediates trafficking of GBA through PGRN as an indispensable adaptor. Collectively, these findings not only demonstrate that PGRN is a novel co-chaperone of HSP70-mediated folding and trafficking pathway and plays an essential role in the GBA lysosomal delivery, but they also provide a new paradigm to guide therapeutic interventions for various HSP70-mediated pathologies and lysosomal storage diseases, including GD.

Gaucher's disease (GD), the most common lysosomal storage disease (LSD), is caused by glucocerebrosidase (GBA) mutations that lead to the accumulation of glucosylceramide (β-GlcCer) in macrophages and other cell types[1,2]. β-GlcCer storage transforms lysosome into tubular-like structure viewed by electronic microscopy, with the lipid-engorged macrophage (Gaucher cell) showing characteristic "wrinkled tissue paper" appearance under light microscopy. There are three types of GD based on its neurological complications (type I is non-neuropathic, type II is acute neuropathic and type III is mild chronic neuropathic). Extra-neurologic systematic features include hepatosplenomegaly, pancytopenia, and osteoporosis as a consequence of Gaucher cells infiltration in these organs[3].

Progranulin (PGRN), also known as granulin epithelin precursor (GEP), PC-cell-derived growth factor (PCDGF), proepithelin, and acrogranin, contains seven-and-a-half repeats of a cysteine-rich motif ($CX_{5-6}CX_5CCX_8CCX_6CCXDX_2HCCPX_4CX_{5-6}C$) (SEQ ID NO: 1) and forms a unique "beads-on-a-string" structure[4]. PGRN is abundantly expressed in epithelial cells, in cells of the immune system, and in neurons[5]. PGRN is known to play a critical role in a variety of physiologic and disease processes, including early embryogenesis, wound healing[6,7], and host defense[8]. PGRN also functions as a neurotrophic factor and mutations in the PGRN gene (GRN) resulting in partial or complete loss of the PGRN protein cause frontotemporal dementia (FTD)[9,10] and neuronal ceroid lipofuscinosis (NCL)[11,12], respectively.

PGRN associates with some members in the TNF receptor superfamily, including TNFR1, TNFR2 and DR3[13-16], and possesses the ability to suppress inflammation in various kinds of conditions[7,13]. Auto-antibodies against PGRN have been found in several autoimmune diseases, including rheumatoid arthritis, psoriatic arthritis, and inflammatory bowel disease, and such antibodies promoted a proinflammatory environment in a subgroup of patients[17,18]. In an effort to determine whether PGRN also plays a role in chronic lung inflammation, we challenged PGRN deficient mice with ovalbumin (OVA), which led to the unanticipated discovery of PGRN as an indispensible GBA-associated factor. Here we report that PGRN is an essential co-chaperone for the lysosomal delivery of GBA through linking GBA/LIMP2 complex to heat shock protein 70 (HSP70), an evolutionarily highly conserved molecular chaperone that mediates the folding and trafficking of numerous proteins[19].

Figure 2:
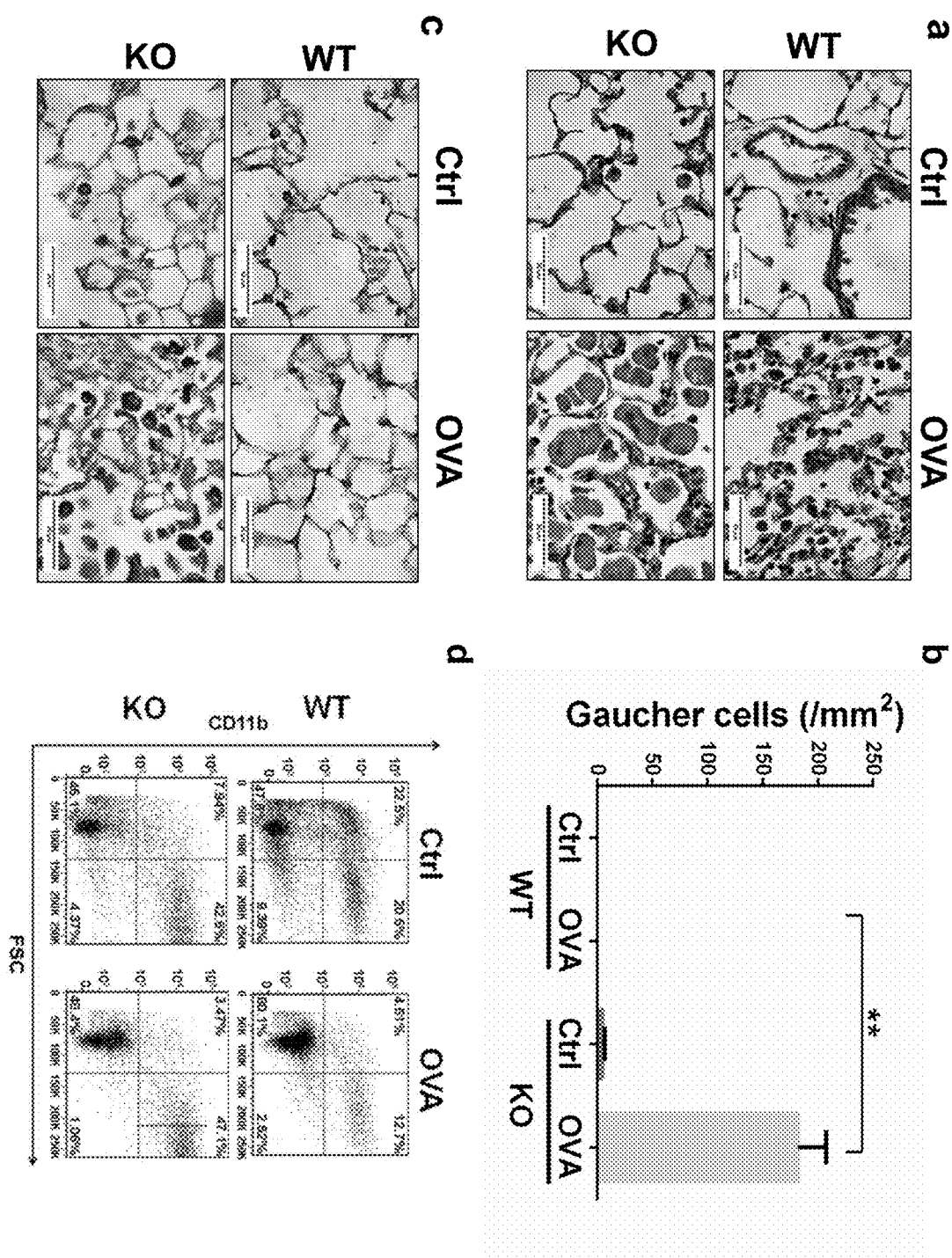
FIGS. 2A-2D. OVA-challenged PGRN KO mice develop Gaucher disease. WT and PGRN KO mice received I.P. injection of OVA at Day 1 and 15, followed by intranasal challenge of 1% OVA at Day 29 for three times a week for four weeks. (A) H&E staining shows giant Gaucher cells in lung of both male and female PGRN KO mice, especially after OVA treatment. (n=10, 5 male and 5 female for each group). (B) Quantification of Gaucher cells in WT and PGRN KO mice, control and OVA challenged. (C) PAS staining of lung from WT and PGRN KO mice, control and OVA challenged. The results show the accumulation of glycolipid in Gaucher cells in PGRN KO mice. (D) Flow cytometry of cells isolated from bronchial alveolar lavage from WT and PGRN KO mice, control and OVA challenged. There is a subpopulation of giant macrophages in PGRN KO mice after OVA treatment, as evidenced by CD11b$^{+}$FSC$^{high}$.

PGRN Deficiency Causes Gaucher-Like Diseases in Both OVA-Challenged and "Aged" Mice Models The findings that PGRN plays important anti-inflammatory and immune regulatory roles in various conditions, including inflammatory arthritis[13], prompted us to examine its involvements in the chronic lung inflammation. For this purpose, chronic lung inflammation was induced in 8-week old WT and PGRN knockout (KO) mice by intraperitoneal (IP) injection of OVA at Day 1 and 15, followed by intranasal challenge of 1% OVA beginning at Day 29 three times a week for four weeks. Surprisingly and remarkably, large numbers of "giant cells" were found in the lungs of PGRN KO mice, particularly after OVA treatment (FIG. 2A). These cells were engorged with materials with a "wrinkled tissue paper" appearance, which is the typical morphology of Gaucher cells. No such cell was found in WT mice, either with or without OVA challenge. A few Gaucher-like cells were identified in unchallenged PGRN KO mice, and the number significantly increased after OVA challenge (FIG. 2A, 2B). Periodic acid-Schiff (PAS) staining showed accumulation of glycolipid material in Gaucher-like cells in PGRN KO mice (FIG. 2C). Flow cytometry analysis of bronchoalveolar lavage identified a subpopulation of giant macrophages in PGRN KO mice after OVA treatment, evidenced by $CD11b^+FSC^{high}$, as the value of forward scattered light (FSC) is proportional to cell size (FIG. 2D).

Figure 3:
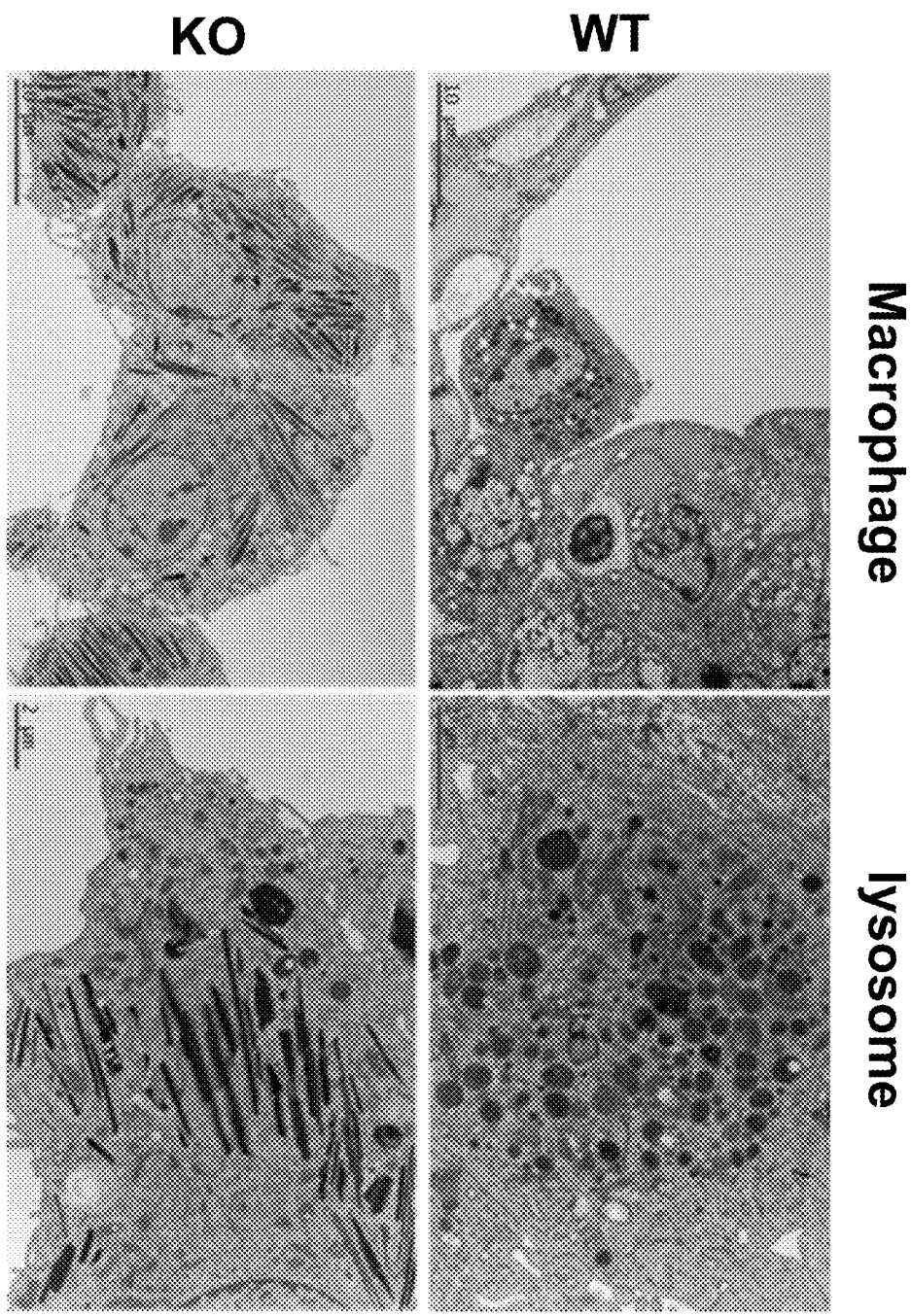
FIG. 3. Macrophage from PGRN KO mice is much larger than that in WT mice, and lysosome become tubular-like shape instead of regular round shape, assayed by transmission electronic microscope (EM) (upper and lower left: 2650×; upper right: 11500×, lower right: 7100×).
Figure 18:
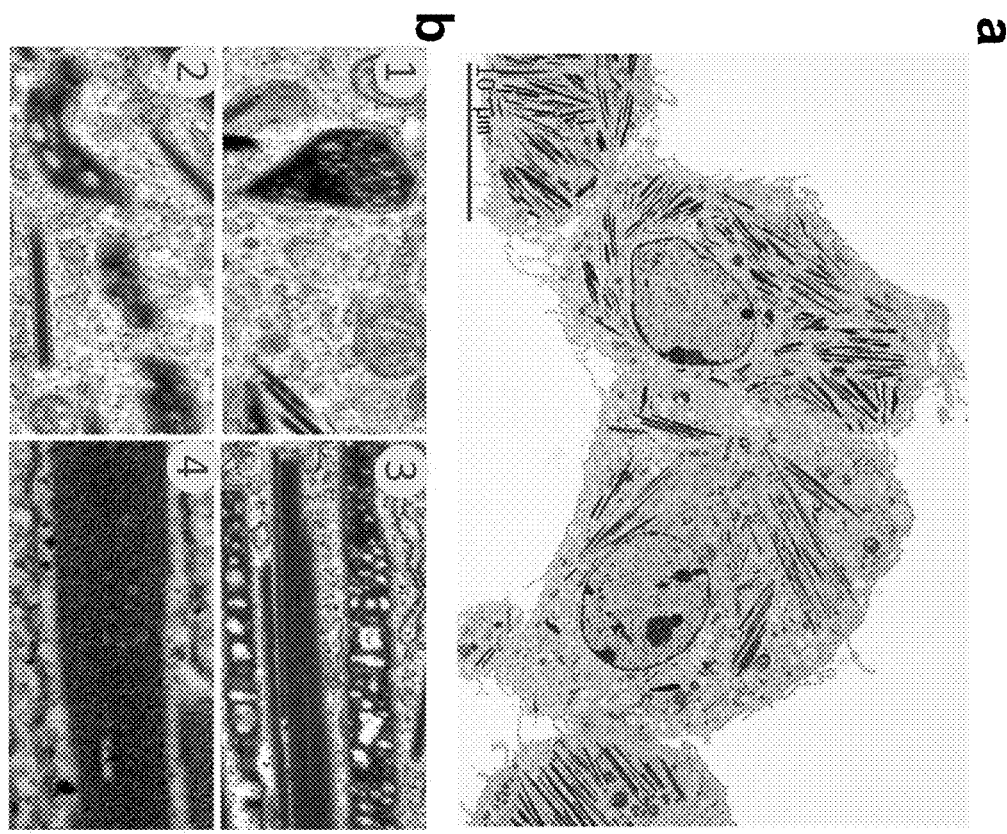
FIGS. 18A-18B. Transmission electronic microscope assays of lung tissues from OVA-challenged WT and PGRN KO mice. (A) Colored and enlarged image of left bottom panel of FIG. 3. Tubular-like lysosomes and mitochondria are shown in purple and orange, respectively (Thanks to Chris Petzold and Kristen Dancel at NYU Medical School OCS Microscopy Core for creating this colored image from the original black and white electronic microscope image). (B) Transformation of lysosome in PGRN null macrophages. 1, Lysosomes show elongated profiles associated with accumulation of material storage (19,500×); 2, Lysosomes became curved-shape with both high dense and low dense material in the lysosomes (19,500×); 3, Lysosome eventually became tubular-like structures with both high dense and low dense material storage (19,500×); 4, Low dense material were eventually replaced with high dense material with intact membrane structure (110,000×).
Figure 19:
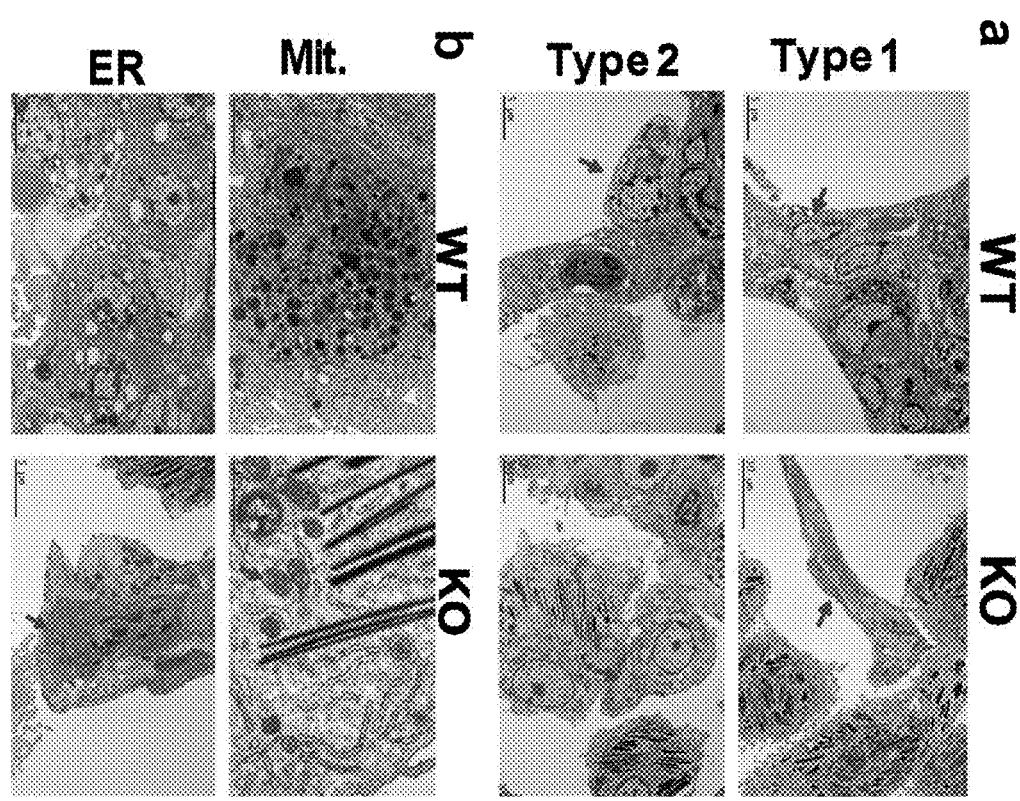
FIGS. 19A-19B. (A) Mitochondria and Endoplasmic reticulum were normal in PGRN null macrophages. Lung tissues from OVA-challenged WT and PGRN KO mice were examined under transmission electronic microscope. Mitochondria (Mit.) from WT (11500×) and PGRN KO (31000×), and endoplasmic reticulum (ER) from WT (4400×) and PGRN KO macrophages (7100×) appeared normal. (B) Type 1 and 2 pneumocytes were normal in PGRN null mice. Lung tissues from OVA-challenged WT and PGRN KO mice were examined under transmission electronic microscope. Both type 1 and 2 pneumocytes from WT and PGRN KO mice appeared normal (all the images were amplified 3400×, except type 1 pneumocytes from PGRN KO was amplified at 2650×).

The PGRN null macrophage displayed the classical tubular-like lysosomal appearance of Gaucher-like cells when examined by transmission electronic microscope (TEM). Macrophage from PGRN KO mice was much larger than those in WT mice, and the PGRN null lysosome became tubular-like instead of a regular round shape (FIG. 3, FIG. 18A). The transformation of lysosome from normal round to tubular-like structure was found along with material accumulation (FIG. 18B). Other organelles, such as mitochondria and endoplasmic reticulum, and other types of cells, type1 and 2 pneumocyte appeared normal (FIG. 19A, 19B).

Figure 4:
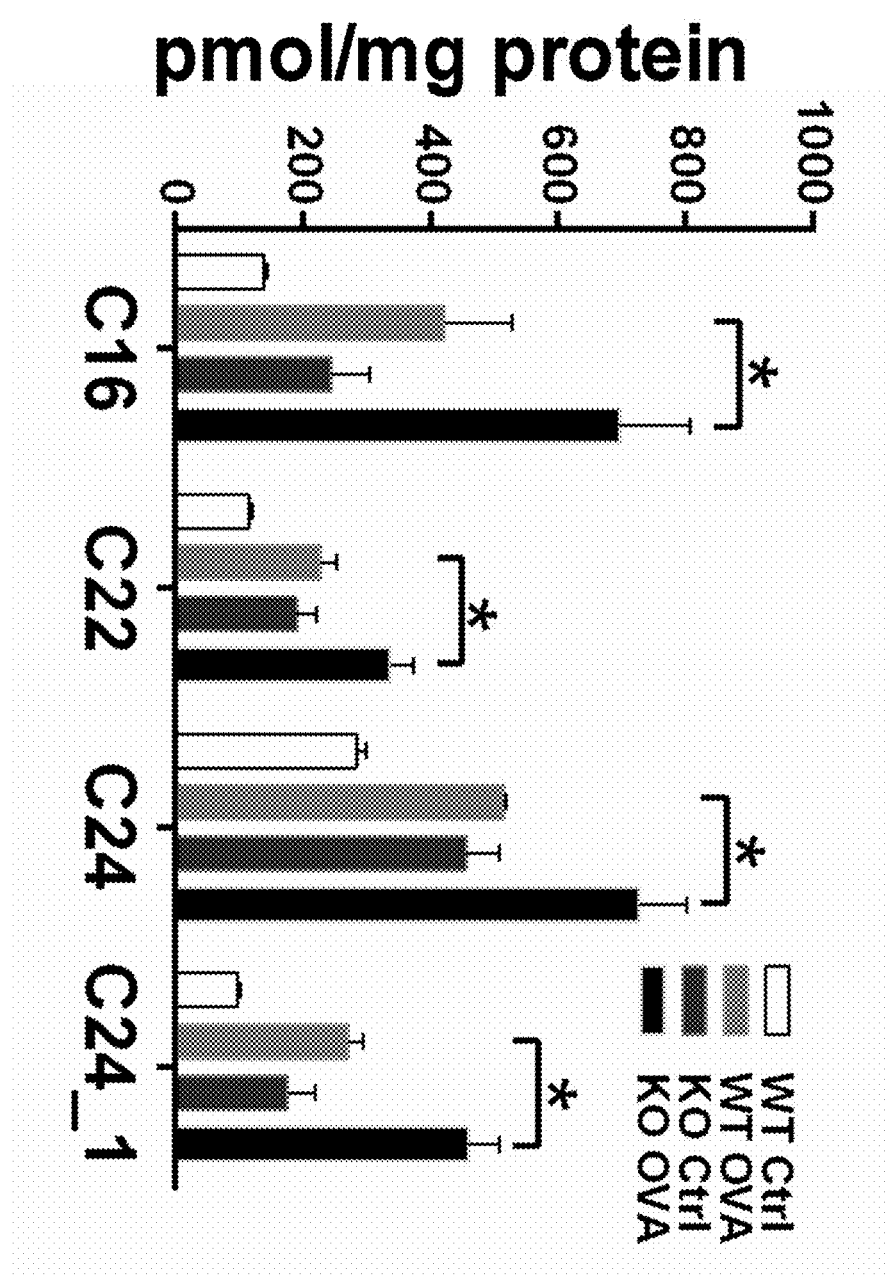
FIG. 4. β-GlcCer accumulates in PGRN KO mice. Lung tissue from WT and PGRN KO mice, with or without OVA challenge, was lysed and 1 mg of protein of each sample was used for lipid composition analysis. The levels of β-GlcCer (pmol/mg protein) with different carbon chain lengths are graphed, as indicated.
Figure 20:
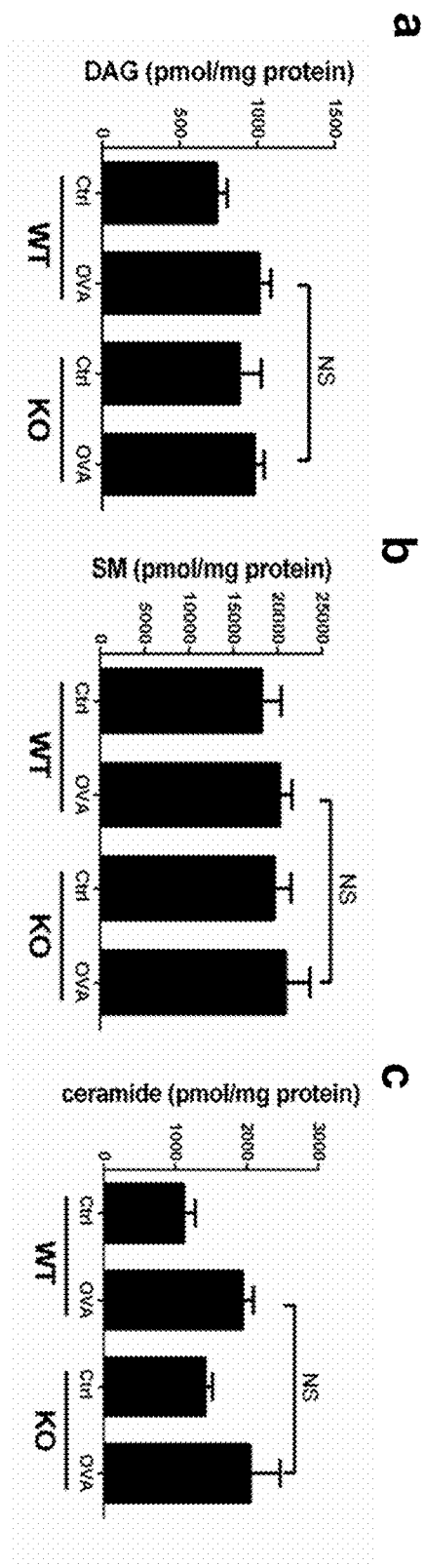
FIGS. 20A-20C. Lipid composition analyses in the tissues and plasma of PGRN KO mice and GD patients. The levels of diacylglycerol (DAG) (A), sphingomyelin (SM) (B), and ceramide (C) are not increased in the lung tissues from OVA-challenged PGRN KO mice compared to OVA-challenged WT mice. Levels of DAG, SM, and ceramide in wild type and PGRN KO animals with and without ovalbumin (OVA) challenge were measured, and levels of DAG, SM, and ceramide are indicated as pmol per mg protein.
Figure 21:
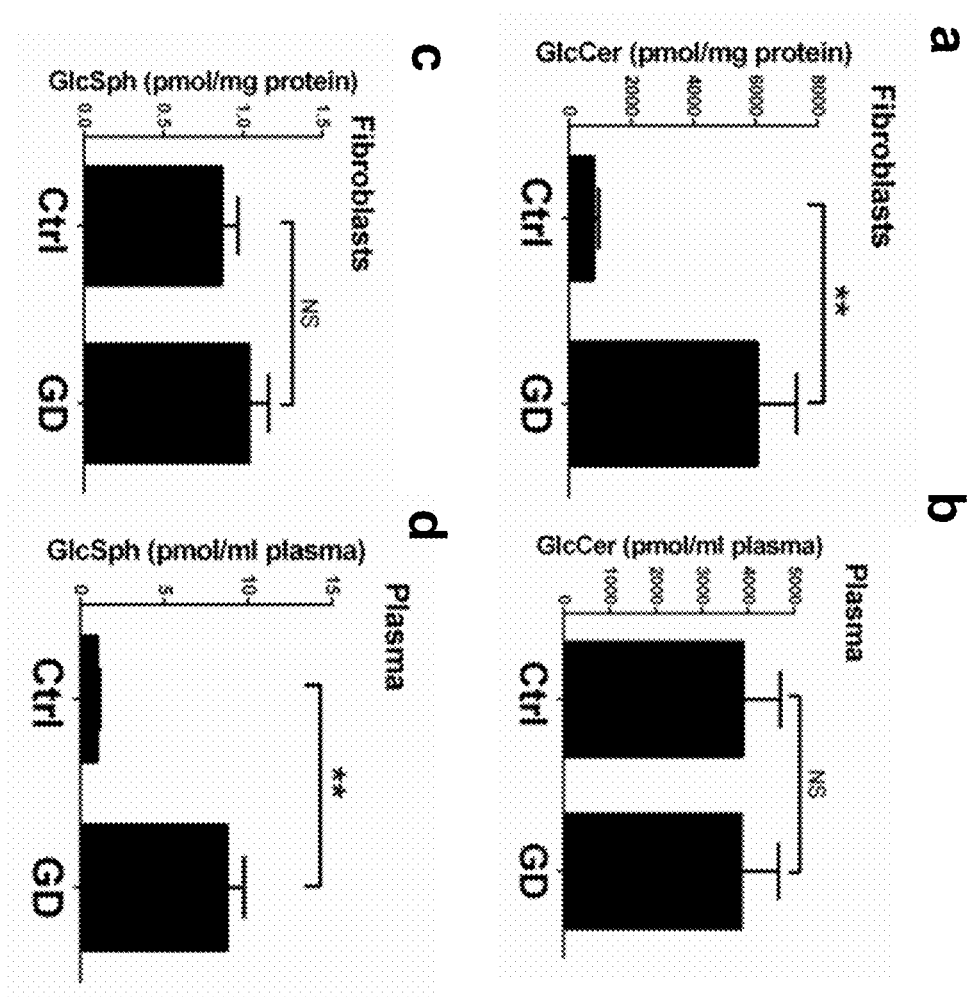
FIGS. 21A-21D. Levels of glucosylceramide (GlcCer) and glucosylsphingosine (GlcSph) in the fibroblasts and plasma of healthy control (Ctrl) and GD patients. The levels of GlcCer are significantly increased in GD fibroblasts (A) but not in GD plasma (B), whereas the levels of GlcSph are increased in GD plasma (D) but not in GD fibroblasts (C).
Figure 22:
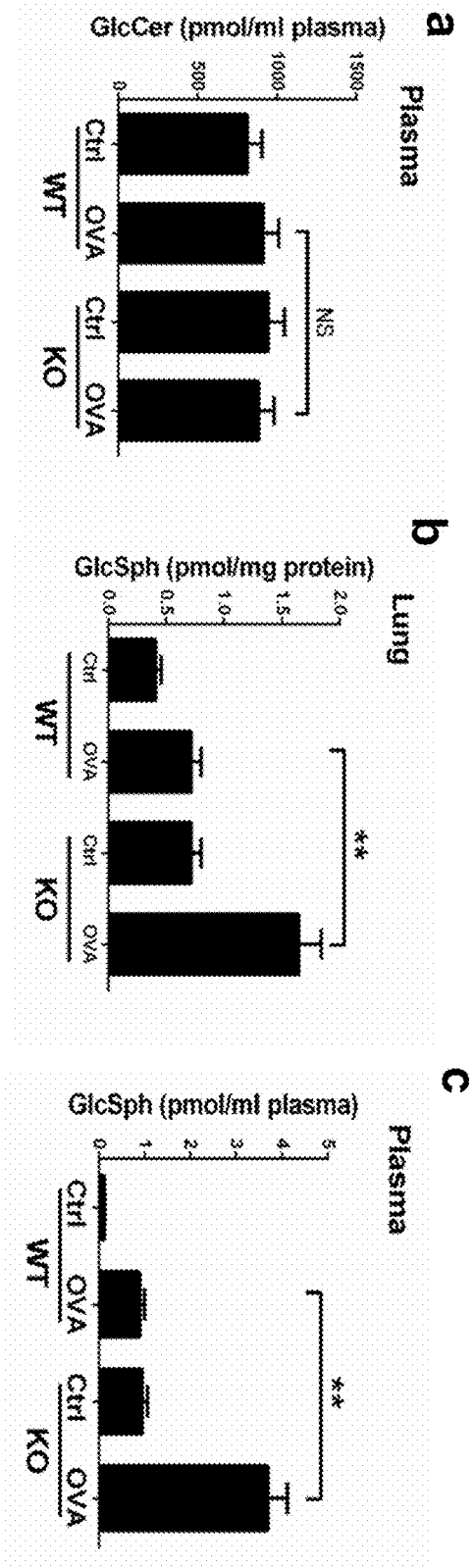
FIGS. 22A-22C. (A) The levels of GlcCer are not elevated in plasma of OVA-challenged PGRN KO mice compare to the OVA-challenged WT mice. (B-C) The levels of GlcSph are elevated in both lung tissues (B) and plasma (C) in OVA-challenged PGRN KO mice compare to the OVA-challenged WT mice.

GD is caused by reduced GBA enzymatic activity that leads to the β-GlcCer accumulation[20]. Lipid composition of lung lysates from WT and PGRN KO mice, with or without OVA challenge, was analyzed as reported previously[21]. As shown in FIG. 4, β-GlcCer showed increases in all chain-length species in both WT and PGRN KO mice with OVA vs. PBS challenge. Moreover, after OVA challenge all species of β-GlcCer were significantly higher in the PGRN KO vs. WT mice (FIG. 4). Even untreated PGRN KO mice had a higher level of β-GlcCer than WT mice. The accumulation of β-GlcCer in PGRN KO mice was specific, because other lipid compositions, such as sphingomyelin, diacylglycerol (DAG), and ceramide, remained unchanged between WT and PGRN KO mice (FIGS. 20A-20C). Interestingly, plasma levels of beta-glucosylsphingosine was found to be significantly elevated in the PGRN deficient mice, although no significant increase was observed in the plasma levels of β-GlcCer (FIGS. 21A-21D and FIGS. 22A-22C).

Figure 5:
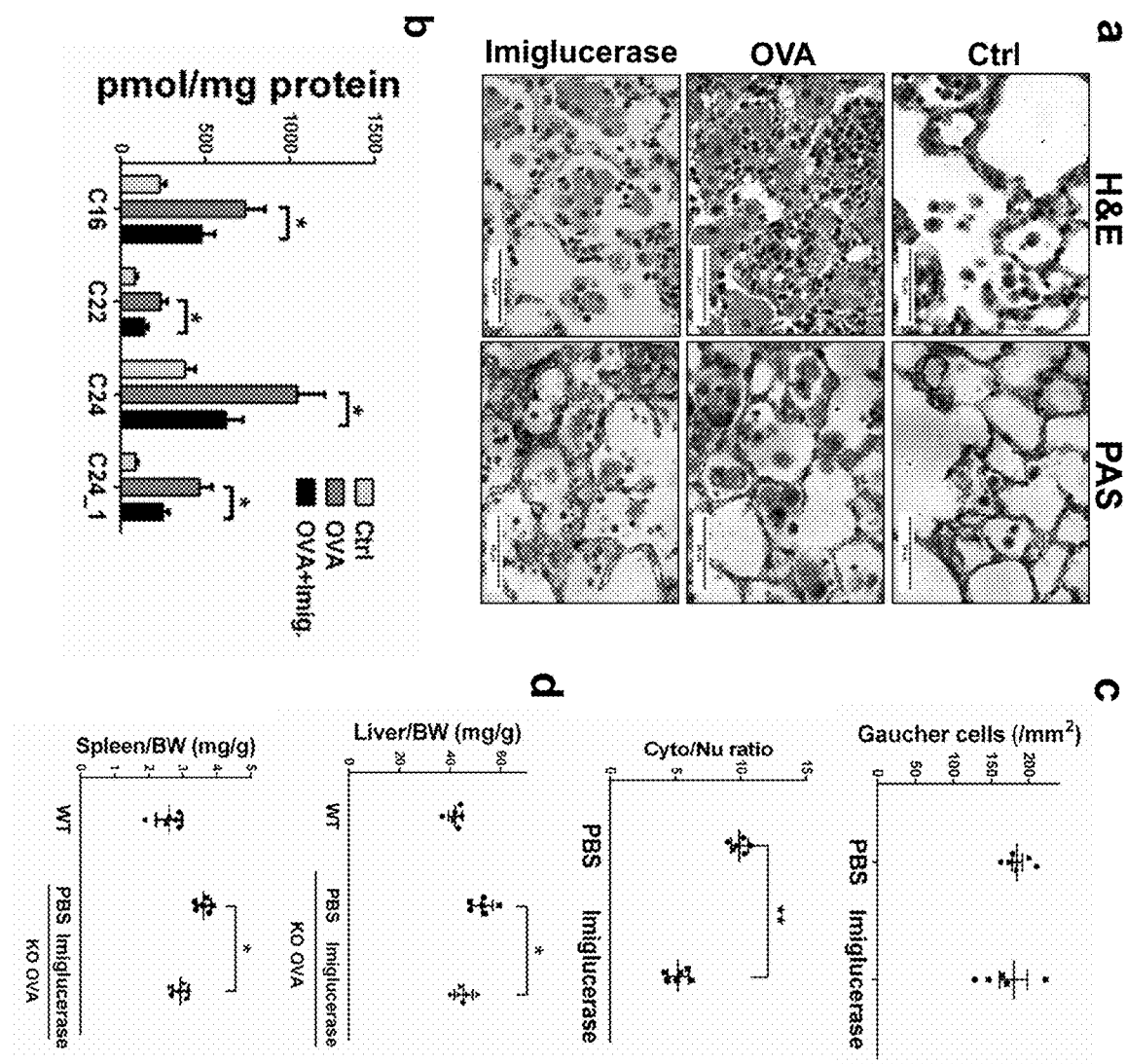
FIGS. 5A-5D. (A) Imiglucerase alleviates lipid accumulation in PGRN KO mice. OVA-challenged PGRN KO mice were treated with imiglucerase (60 u/kg) once a week starting at the week of first intranasal challenge with 1% OVA. H&E and PAS staining of lung tissues (n=6 for each group). (B) Imiglucerase treatment reduces β-GlcCer accumulation in OVA-challenged PGRN KO mice. Lung tissue from OVA-unchallenged (Ctrl), OVA-challenged PGRN KO mice treated with vehicle (OVA) or Imiglucerase (Imig.), was processed and analyzed as described in FIG. 4. (C) Quantification of Gaucher cells in PGRN KO mice with or without imiglucerase treatment. (D) Sizes of the liver and spleen of PGRN KO mice induced by OVA challenge, with and without imiglucerase treatment. Both liver and spleen were significantly reduced following imiglucerase treatment. One-way ANOVA tests was used to compare means among groups (*p<0.05; **p<0.01, two sided).

Although GBA is transported to lysosome independently of the mannose-6-phophate receptor (MPR) system[22,23], Imiglucerase, a macrophage-targeted, mannose-terminated human GBA for use in enzyme replacement therapy (ERT) for Gaucher's disease, is delivered to lysosome via an MPR-dependent pathway. PGRN KO mice were challenged with OVA, and treated with PBS or imiglucerase injection (60 u/kg/week) at the beginning of the first week of intranasal challenge until to the end of the experiment[24]. Following OVA challenge many Gaucher-like cells were present and almost occupied the whole alveolar space (FIG. 5A, middle panel). Imiglucerase injection significantly decreased size and accumulation of PAS-positive material (FIG. 5A, lower panels) as well as β-GlcCer storage (FIG. 5B) in Gaucher-like cells. The numbers of Gaucher-like cells were comparable, however the ratio between size of the cytoplasm and nucleus significantly decreased with imiglucerase (FIG. 5C), indicating the size of the Gaucher-like cells became smaller after imiglucerase treatment. The size of the enlarged liver and spleen of PGRN KO mice induced by OVA challenge was also significantly reduced following imiglucerase treatment (FIG. 5D). The general physical activities in PGRN null mice challenged with OVA were improved by imiglucerase treatment. PGRN KO mice challenged with OVA had decreased physical activity because of compromised pulmonary function. Such mice were sick and did not like to move until touched by forceps (data not shown). OVA-challenged PGRN KO mice receiving imiglucerase therapy became normal and active (data not shown). Collectively, these data and the response of the PGRN KO mice to imiglucerase confirmed that OVA-challenged PGRN deficient mice developed the Gaucher's disease phenotype.

Figure 6:
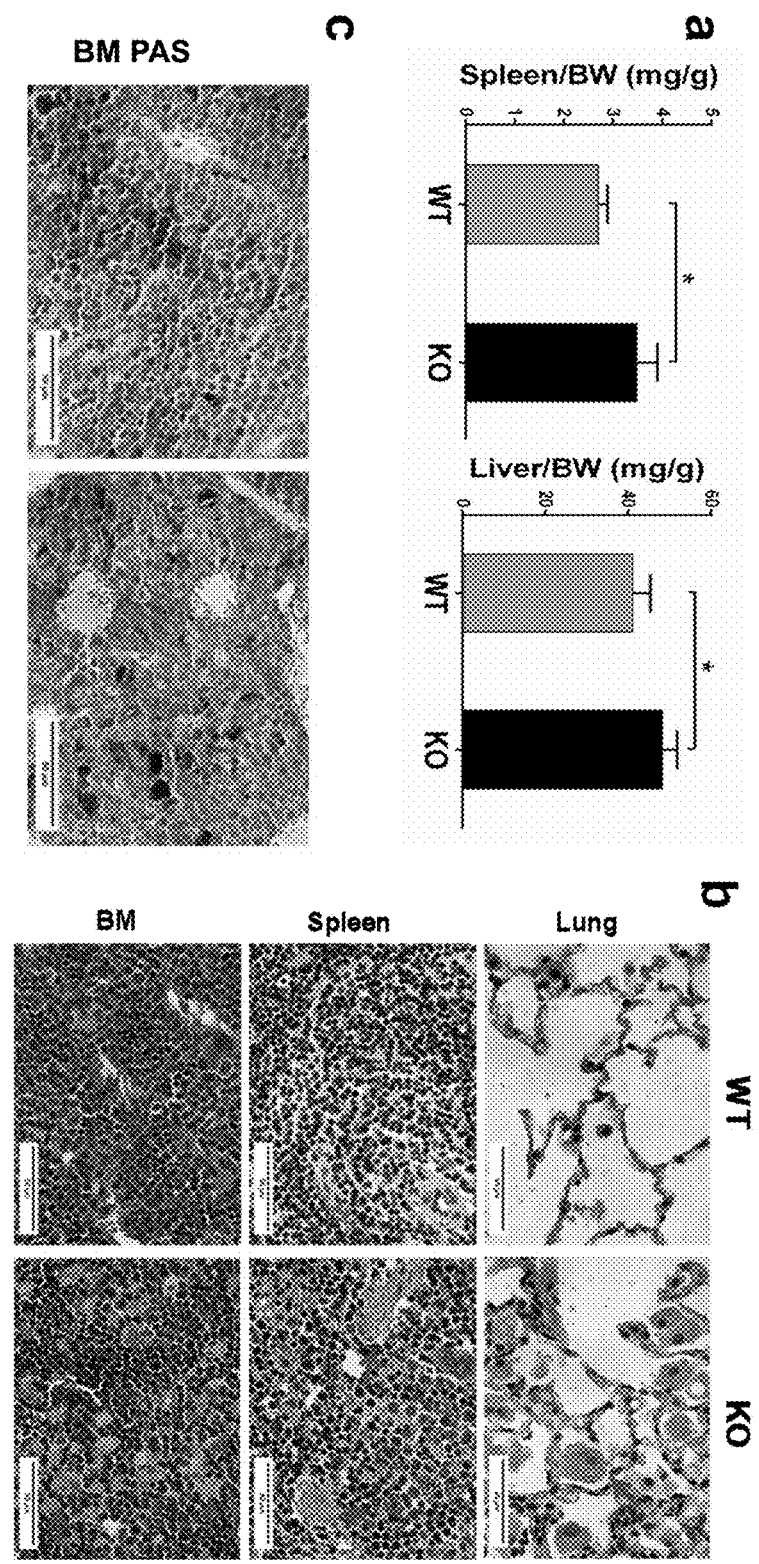
FIGS. 6A-6C. Aged PGRN null mice develop Gaucher's disease spontaneously. 1 year-old WT and PGRN KO mice without any challenge were sacrificed and lung, spleen, liver, and bone marrow were collected for histology. (A) Aged PGRN KO mice develop hepatosplenomegaly. Liver and spleen weight divided by total animal body weight is graphed for WT and KO mice (n=8 per group). (B) Histology of lung, spleen and bone marrow. Gaucher cells were found in lung, spleen, and bone marrow in PGRN KO mice, but not in WT mice. (C) PAS staining of bone marrow shows glycolipid storage in Gaucher cells.
Figure 7:
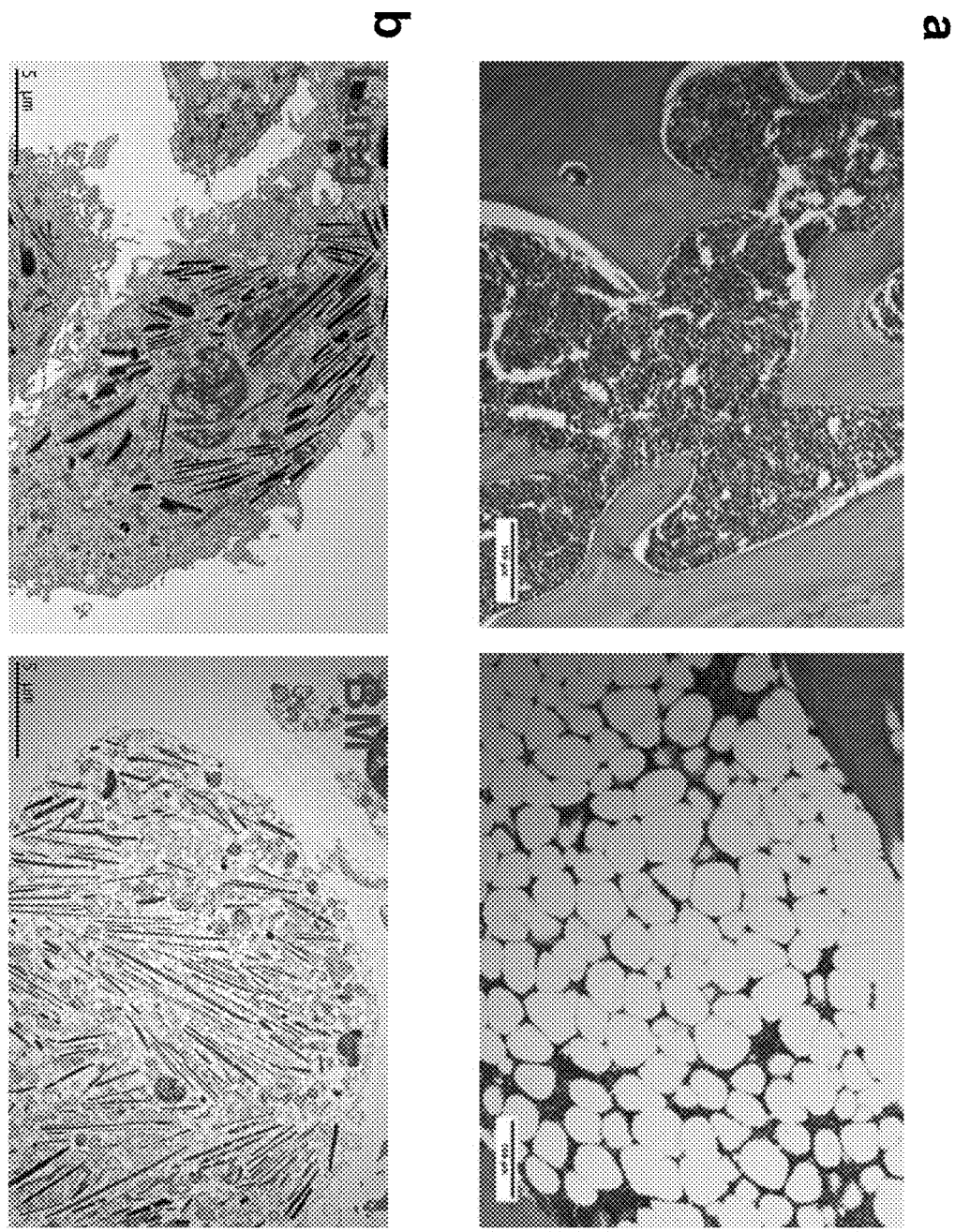
FIGS. 7A-7B. (A) Histology of bone marrow in WT and PGRN KO mice, BM were replaced by fat tissues in PGRN KO, but not in WT mice. (B) Gaucher cells under EM. Typical tubular-like lysosomes were founded in lung and bone marrow in PGRN KO mice. Non-paired student T-test were used to compare liver size and spleen size between WT and PGRN KO mice (*p<0.05).
Figure 23:
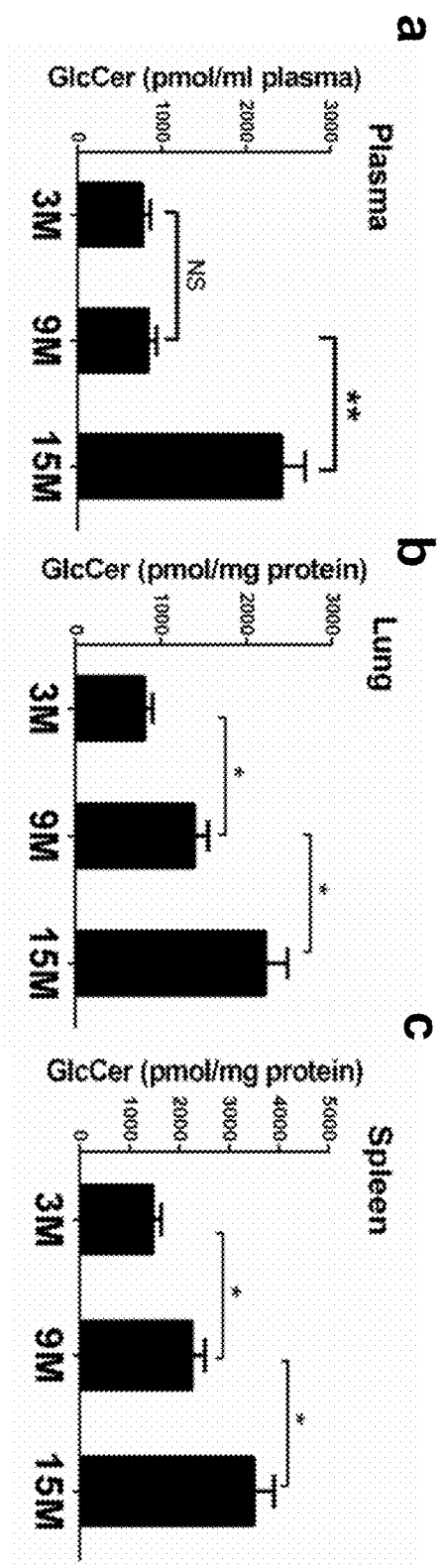
FIGS. 23A-23C. The levels of GlcCer in plasma (A), lung (B) and spleen (C) are increased in aging of PGRN KO mice. 3 month-, 9 month-, and 15 month-old PGRN KO mice (n=6 for each group) were sacrificed, and plasma, lung and spleen were used to measured β-GlcCer. Independent student-T test and one-way ANOVA were used for statistical analysis (*p<0.05; **p<0.01; two-sided).
Figure 24:
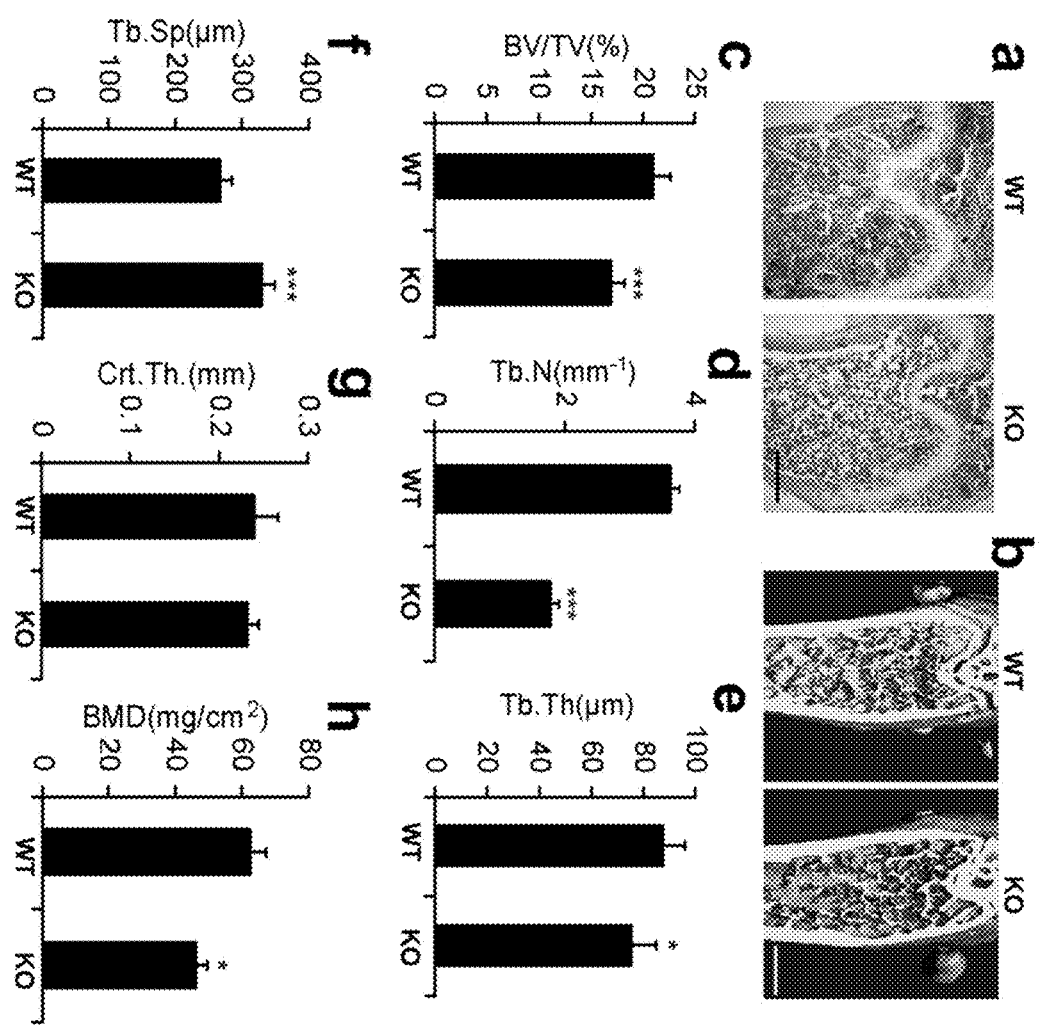
FIGS. 24A-24H. Aged PGRN KO mice develop osteopenia in long bone. 1 year-old WT and PGRN KO mice were sacrificed and two femurs of each mice were dissected, one was for bone histology and the other one was for micro-CT. (A) Longitudinal sections of WT and PGRN KO femurs stained with H&E. Trabecular bone thickness and connectivity are decreased in the PGRN KO femur. Scale bars represent 0.5 mm. (B) Representative images of three-dimensional micro-CT reconstructions of femur from aged WT and PGRN KO femurs. Histograms of 3-D trabecular structure parameters in the secondary spongiosa of the proximal femurs of WT and KO mice: BV/TV=bone volume/total volume (C); TbN=trabecular number (D); Tb.Th=trabecular thickness (E); TbSp=trabecular separation (F). Cortical thickness (Crt.Th) (G). (H) Whole-body bone mineral density (BMD) as assessed by dual x-ray absorptiometry scanning.
Figure 25:
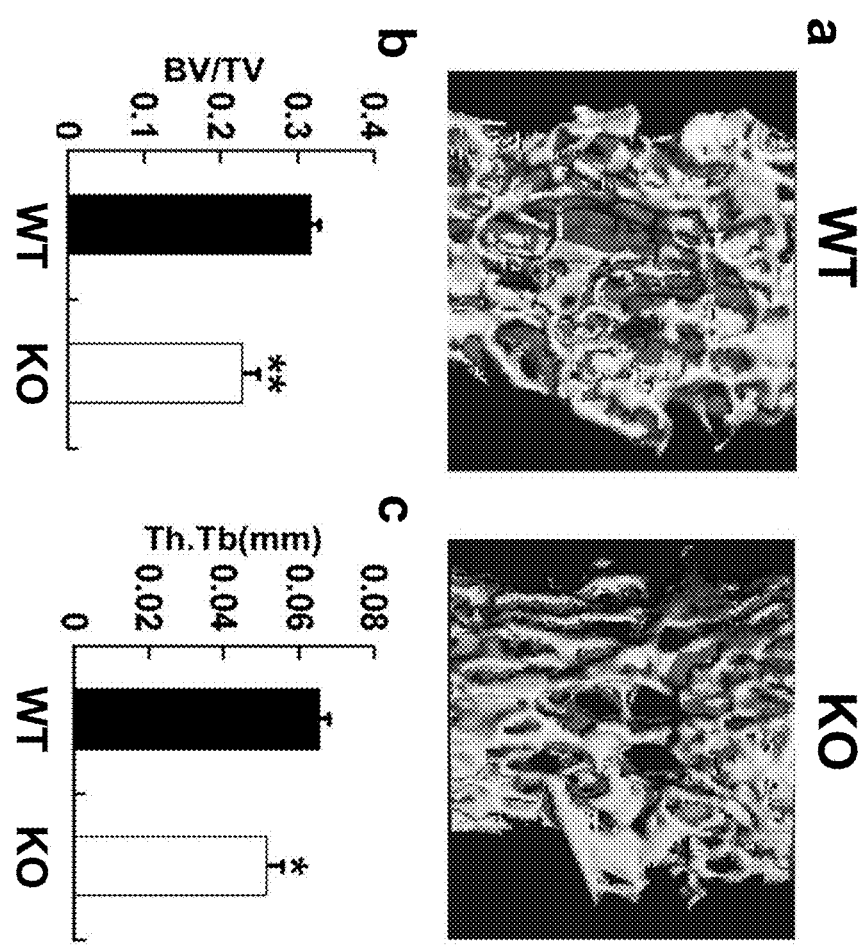
FIGS. 25A-25C. Aged PGRN KO mice develop osteopenia in spine. Lumbar spine from aged WT and PGRN KO mice were dissected for micro-CT analysis. (A) Images of L4 vertebrae from WT and PGRN KO mice shows reduced bone mineral density. Bone volume (B) and thickness of trabecular bone (C) were significantly decreased in PGRN KO mice. Data are expressed as means±S.D. (n=8 per group); Independent student-T test and one-way ANOVA were used for statistical analysis (*P<0.05; P<0.01; *P<0.001 versus the WT group; two-sided)

Since the PGRN KO mice showed pulmonary Gaucher-like cells even in the absence of OVA challenge, we next sought to determine whether aged PGRN deficient mice developed Gaucher-like disease spontaneously. WT and PGRN KO mice were maintained for up to one year, and then 1 year-old WT and PGRN KO mice without any challenge were sacrificed. Lung, spleen, liver, femur, and spine were collected for histology and micro-CT analyses. Similar to GD patients, aged PGRN KO mice developed hepatosplenomegaly (FIG. 6A), which is a most common symptom of Gaucher's disease. Histologically, Gaucher-like cells were found in lung, spleen, and bone marrow in aged PGRN KO mice, but not in age-matched WT mice (FIG. 6B). PAS staining of bone marrow showed glycolipid storage in the PGRN null Gaucher-like cells (FIG. 6C). β-GlcCer levels in tissues and plasma were increased in aging in PGRN deficient mice (FIGS. 23A-23C). The bone marrow was replaced by fat tissue in some aged PGRN KO mice (FIG. 7A). When examined under TEM, the tubular-like lysosome was observed in PGRN-null Gaucher-like cells from PGRN KO lung and bone marrow (FIG. 7B). In addition, aged PGRN deficient mice exhibited features of osteopenia in long bone (FIGS. 24A-24H) and vertebrae (FIGS. 25A-25C), which is also a well-documented symptom of Gaucher's disease. In conclusion, aged PGRN deficient mice developed Gaucher-like disease phenotype spontaneously.

Figure 8:
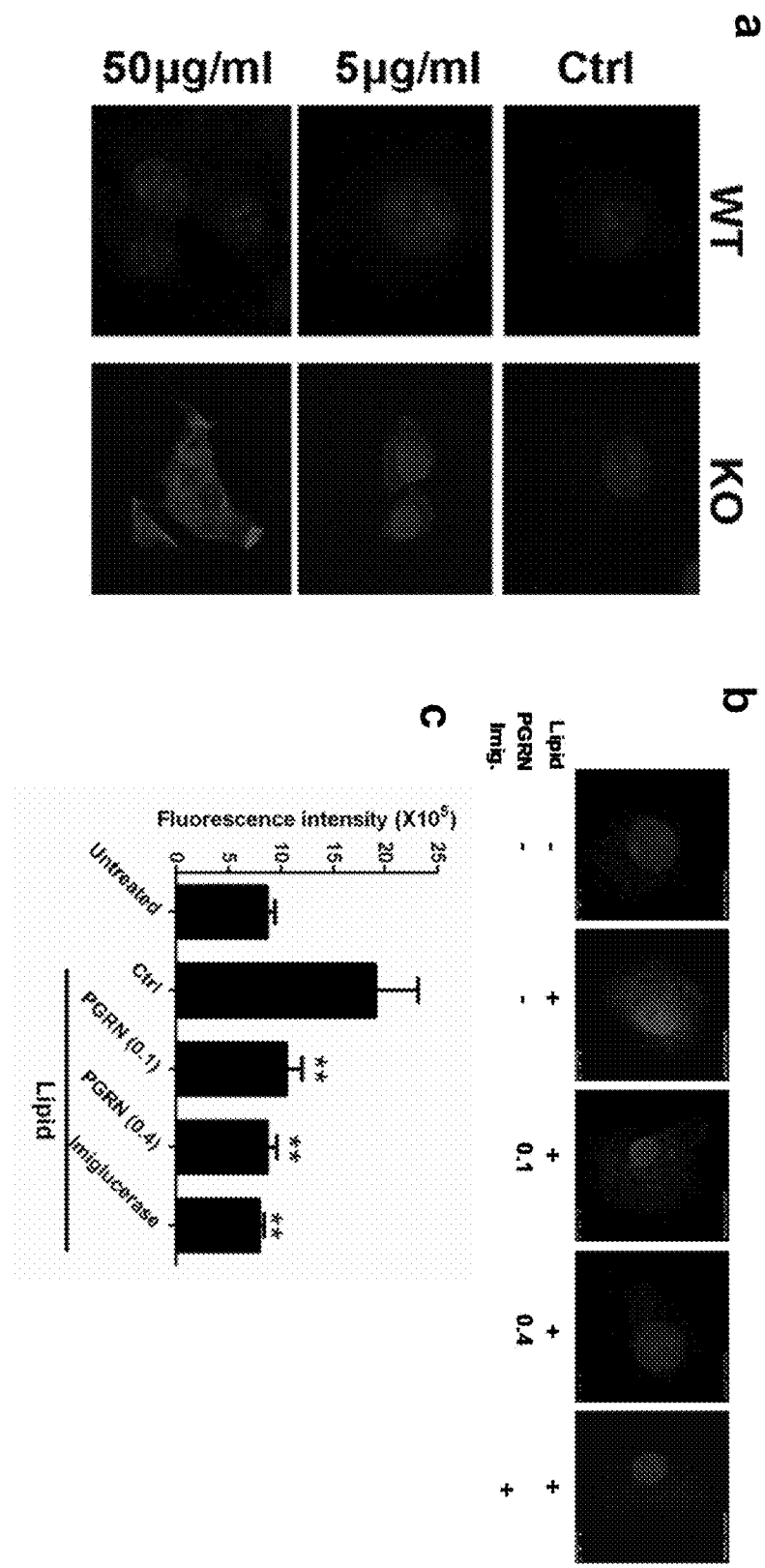
FIGS. 8A-8C. rPGRN rescues the GD phenotype in vitro and in vivo. (A) β-GlcCer is accumulated in PGRN-deficient BMDM. BMDM from WT and PGRN KO mice were treated with lipid mixture at 5 and 50 μg/ml for 10 days. Accumulation of β-GlcCer was detected by immunofluorescence staining with specific antibodies against β-GlcCer and visualized by confocal microscope. (B) rPGRN prevents β-GlcCer accumulation in PGRN KO BMDM in dose-dependent manner. BMDM from PGRN KO mice were treated with lipid mixture in the presence of various amounts of PGRN, as indicated, or imiglucerase (Imig, 160 mU/ml, serving as a positive control) for 10 days. β-GlcCer was stained by immunofluorescence and a representative image presented. (C) Quantification of β-GlcCer accumulation. Ten individual images, as shown in panel B, were selected and fluorescence intensities measured by Image J software. Data are presented as mean values obtained from three independent experiments.
Figure 26:
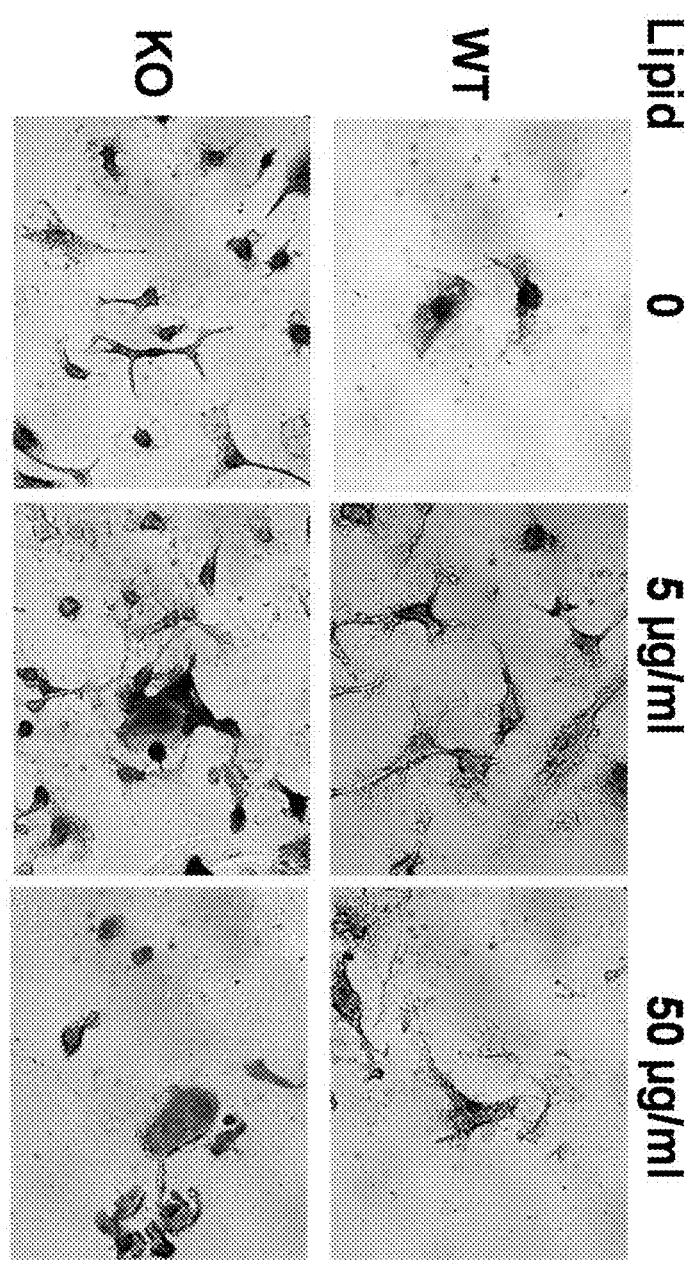
FIG. 26. Giant macrophages were found in PGRN-deficient BMDM treated with lipid. BMDM were isolated and differentiated from WT and PGRN KO mice, and the cells were treated with lipid mixture at 5 and 50 µg/ml for 10 days. H&E staining of cultured BMDM. Giant BMDM are present in PGRN KO mice after lipid treatment.

Recombinant PGRN Prevents β-GlcCer Accumulation in PGRN Null Macrophages and GD Development in PGRN-Deficient Mice To evaluate whether recombinant PGRN (rPGRN) could rescue the GD-like phenotype seen in PGRN KO animals, we first developed an in vitro cell culture model to mimic β-GlcCer accumulation in macrophage in GD. Bone-marrow-derived-macrophage (BMDM) were isolated and differentiated from WT and PGRN KO mice as described previously[25]. BMDM cells were treated with 5 and 50 µg/ml brain lysates which contains many types of lipids for 10 days. H&E staining showed that giant macrophages were present in PGRN KO BMDM, but not in WT BMDM (FIG. 26). Immunofluorescence staining revealed that β-GlcCer was accumulated in PGRN KO BMDM in a dose-dependent manner after lipid mixture treatment. However BMDM from WT mice did not show an increased level of β-GlcCer (FIG. 8A).

Figure 27:
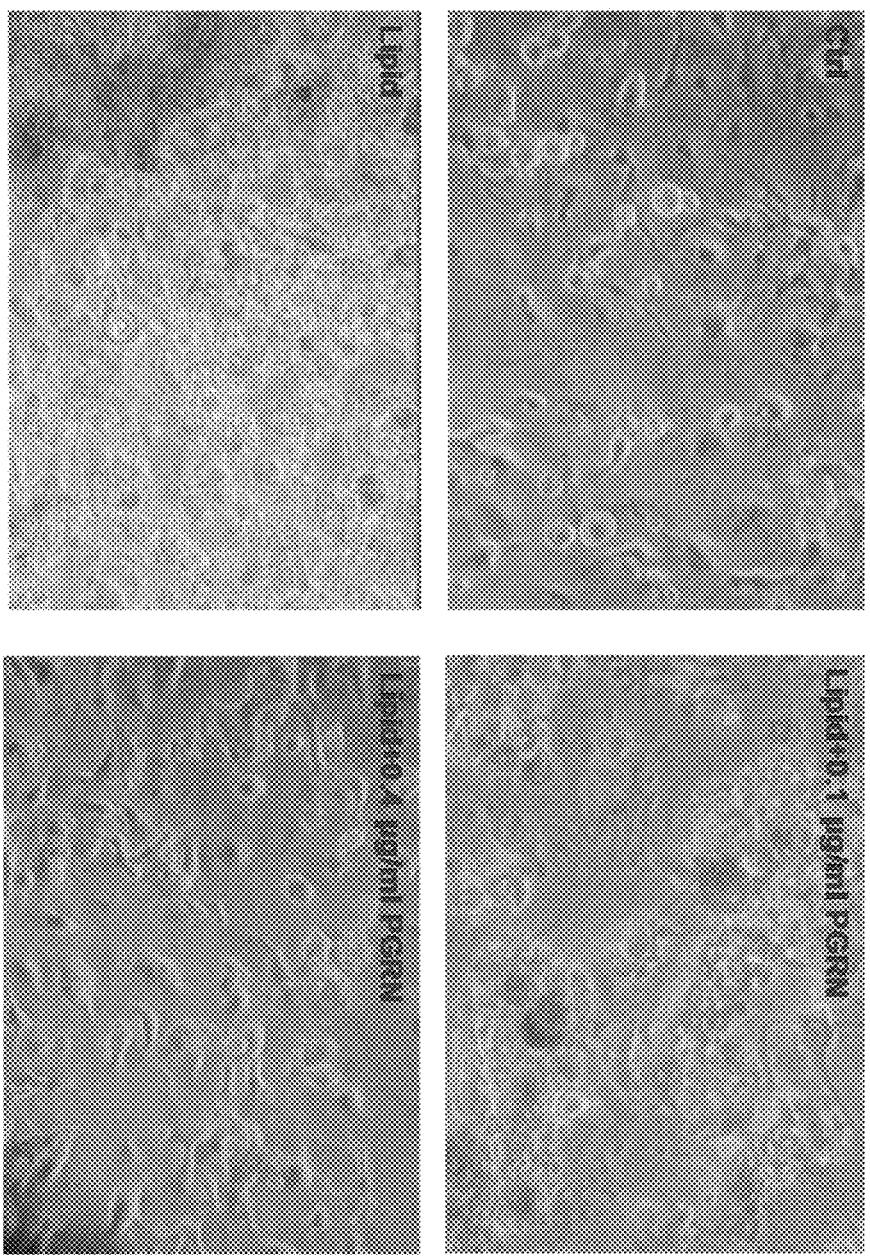
FIG. 27. PGRN reversed lipid-induced morphology changes of PGRN null BMDM. BMDM from PGRN KO mice were isolated and differentiated in vitro for 5 days. Then BMDM were treated with 50 µg/ml lipid mixture alone or with different doses of recombinant PGRN (0.1, 0.4 µg/ml) for 10 days, the cell culture medium were replenished every three days. The cell morphology was observed under phase-contrast microscope.
Figure 29:
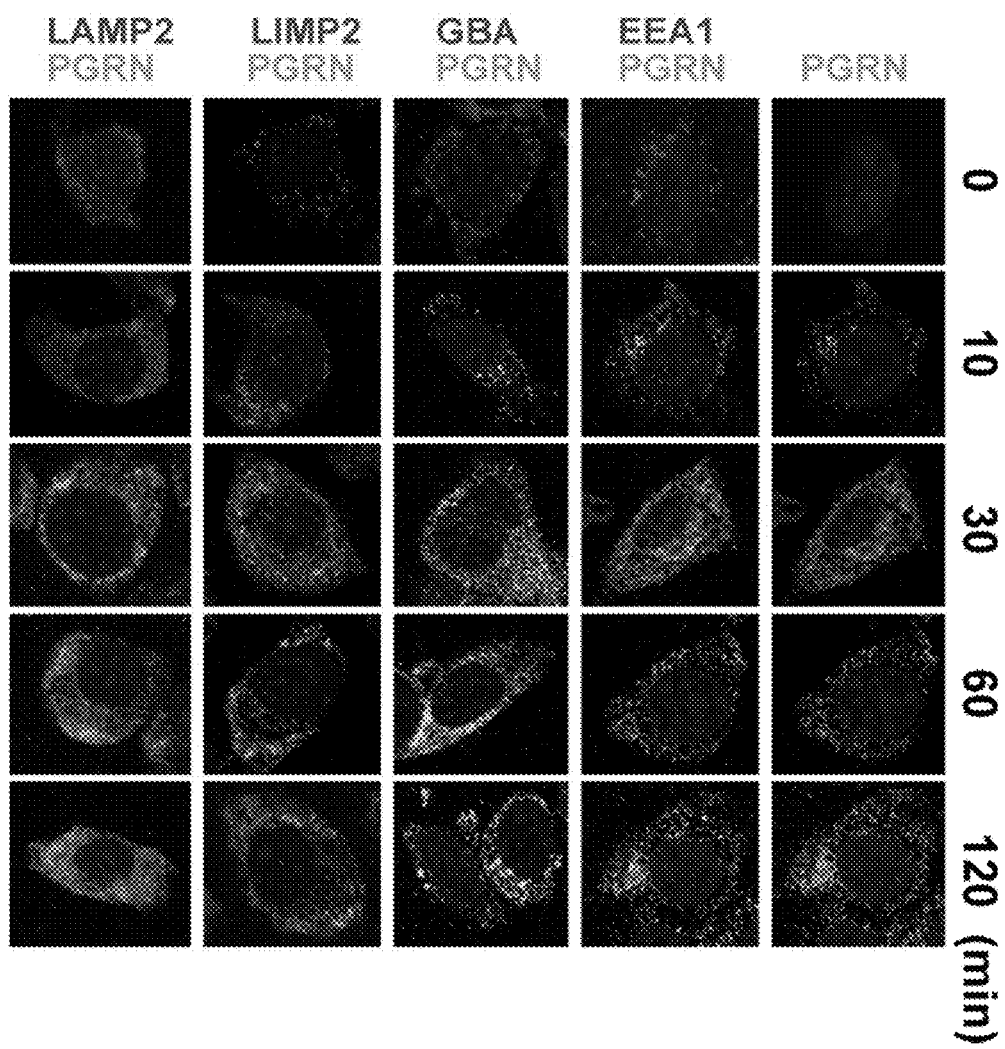
FIG. 29. rPGRN was efficiently taken-up through endocytosis in BMDMs and blocking known PGRN's signal pathways, including ERK, PI3K and mTOR, did not affect rPGRN's effect on β-GlcCer clearance. Endocytosis of rPGRN in PGRN null BMDMs. BMDMs from PGRN KO mice were differentiated for 5 days as described in Materials and Methods. rPGRN were added in the culture medium at final concentration of 5 µg/ml for different time points, as indicated. The cells were fixed immediately at the end of each time points. The uptake and distribution of rPGRN were examined by immunofluorescence staining with PGRN antibody and antibodies against different molecules, as indicated. The images in the 1st row shows the endocytosis of rPGRN alone, and the images in the 2nd, the 3rd, the 4th and the 5th row reveal the co-localizations between uptaked rPGRN and EEA1, GBA, LIMP2, and LAMP2, respectively.

To test whether rPGRN, which was effectively taken-up through endocytosis and delivered to lysosome[26] (FIG. 29 and FIG. 30), could prevent β-GlcCer accumulation in PGRN KO BMDM, 0.1 and 0.4 µg/ml PGRN protein was added to the culture medium with lipid mixture (50 µg/ml) for 10 days, and the accumulation of β-GlcCer was measured by immunofluorescence staining. Under a light microscope, BMDM after lipid exposure looked enlarged and disorganized with highly refractile cytoplasmic punctae, and this morphological change was corrected by PGRN in a dose-dependent manner (FIG. 27). β-GlcCer was accumulated with lipid treatment, and this accumulation was effectively blocked by addition of rPGRN and imiglucerase (serving as a positive control) (FIGS. 8B and 8C). In addition, blocking the known PGRN's signal pathways, including ERK, PI3K and mTOR, did not affect rPGRN's effect on β-GlcCer clearance (FIG. 30), indicating that prevention of β-GlcCer accumulation by recombinant PGRN was mediated mainly by uptake through endocytosis, but not by activating cytosolic signaling pathways.

Figure 9:
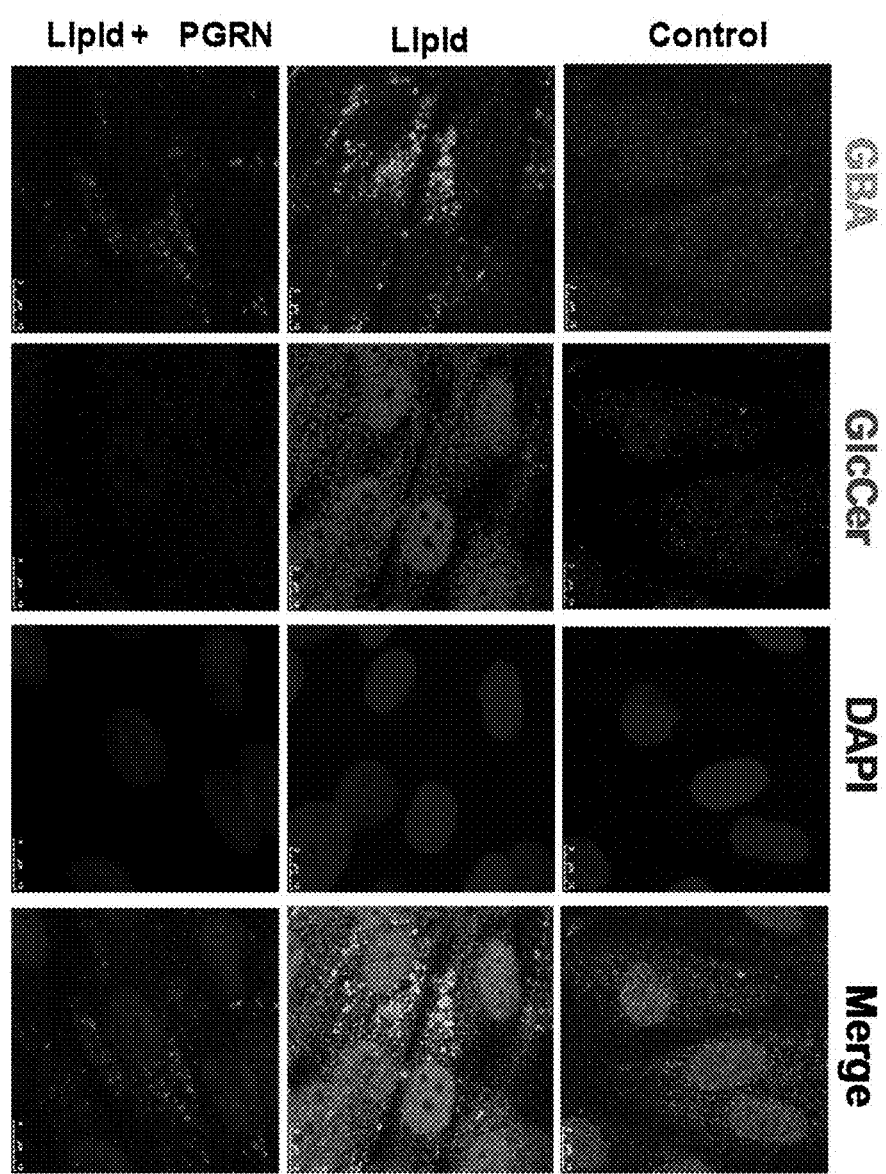
FIG. 9. rPGRN prevents GBA aggregation and β-GlcCer accumulation in the fibroblasts from GD patients. Fibroblasts from type II GD patients were treated with lipid mixture in the presence or absence of rPGRN for 2 days, and levels of GBA (Green) and β-GlcCer (Red) were measured by immunofluorescence staining with their specific antibodies, the nuclei stained with DAPI, and images captured by co-focal microscope.

The finding that recombinant PGRN prevents GBA aggregation and β-GlcCer accumulation in PGRN KO BMDMs was further confirmed with fibroblasts from GD patients. Briefly, fibroblasts from type II GD patients were treated with 50 µg/ml lipid mixture with or without 0.4 µg/ml rPGRN. GBA became aggregated around nucleus accompanied with β-GlcCer accumulation following lipid treatment, and all these phenotypes were markedly inhibited by addition of rPGRN (FIG. 9).

Figure 10:
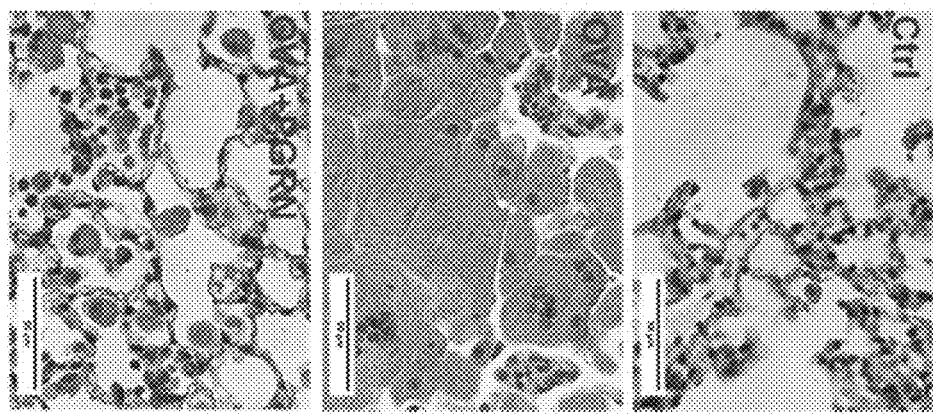
FIGS. 10A-10C. (A) rPGRN prevents GD development in OVA-challenged PGRN null mice. PGRN KO mice were challenged by OVA, and treated with PBS or rPGRN (4 mg/kg) once a week starting at the week of first intranasal challenge with OVA (n=6 per group). H&E staining of lung tissues reveals that rPGRN dramatically decreased Gaucher cells formation. (B) Quantification of Gaucher cells number from untreated, OVA-treated, and OVA+PGRN treated PGRN KO mice. (C) Quantification of Gaucher cell size from untreated, OVA-treated, and OVA+PGRN treated PGRN KO mice. One-way ANOVA was used to compare means among multiple groups (*p<0.05; **p<0.01; two sided).
Figure 10:
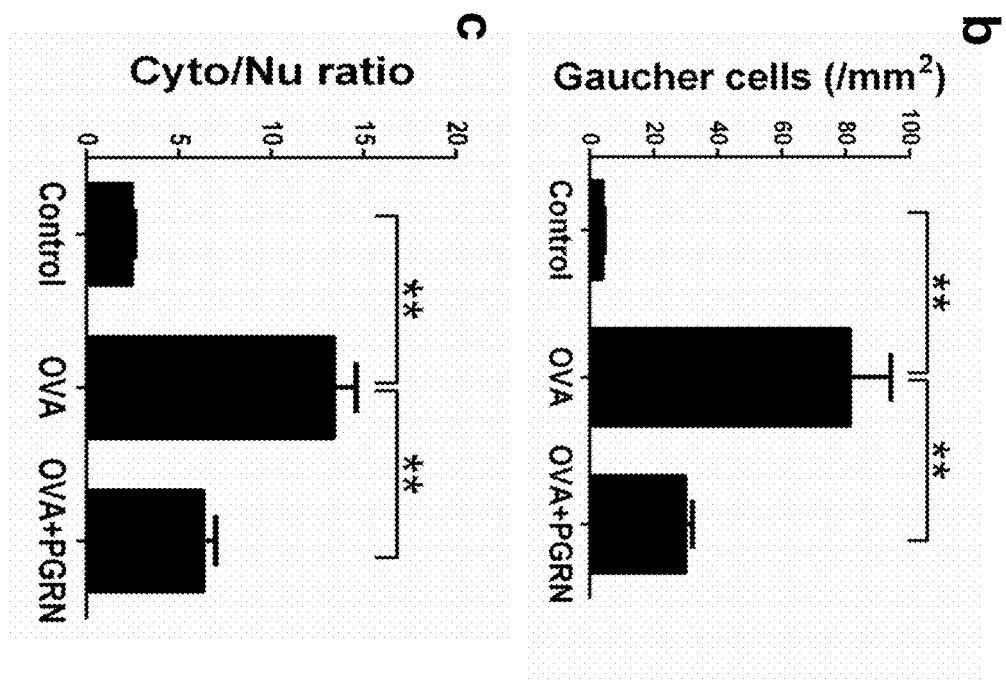

Next we examined whether rPGRN could also rescue the GD phenotype in vivo. PGRN KO mice challenged with OVA were I.P. injected with either PBS or rPGRN (4 mg/kg per week) from the first week of starting the intranasal challenge until to the end of the experiment. Histology of lung tissues showed infiltration with Gaucher-like cells induced by OVA challenge in PGRN KO mice, and rPGRN dramatically reversed the phenotype (FIG. 10A). Unlike Imiglucerase treatment which reduced size without a significant effect on the number of Gaucher-like cells (FIG. 5C, 5D), rPGRN significantly decreased both number and size of Gaucher-like cells (FIG. 10B, 10C), indicating that PGRN inhibited both Gaucher-like cells formation and β-GlcCer accumulation.

Figure 11:
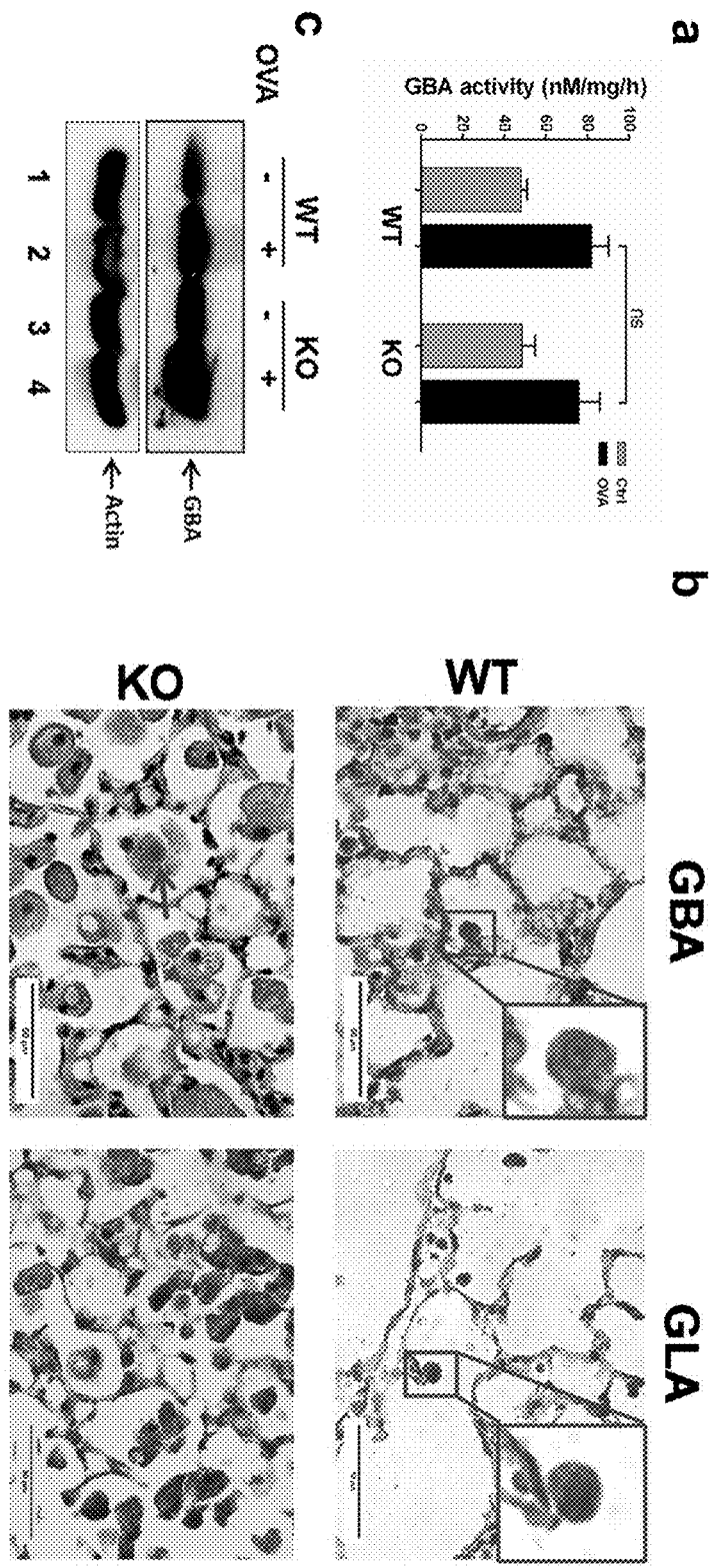
FIGS. 11A-11C. PGRN is required to deliver GBA and LIMP2 to lysosomes. (A) GBA enzyme activities are unchanged in PGRN KO vs. WT mice. Lung tissues from WT and PGRN KO mice after either PBS or OVA challenge were lysed, and GBA activity measured by cleavage of its substrate 4 MUGP. (B) GBA protein levels are not decreased, in fact are slightly increased, in KO vs. WT mice after PBS and OVA challenge. Lung tissues were lysed and the level of GBA was measured by Western blotting. (C) Distribution of GBA, but not GLA, is altered in PGRN KO macrophage. Paraffin-embedded lung slides were stained with GBA or GLA antibody by immunohistochemistry. The aggregation of GBA in PGRN KO macrophages is indicated with an arrow.
Figure 12:
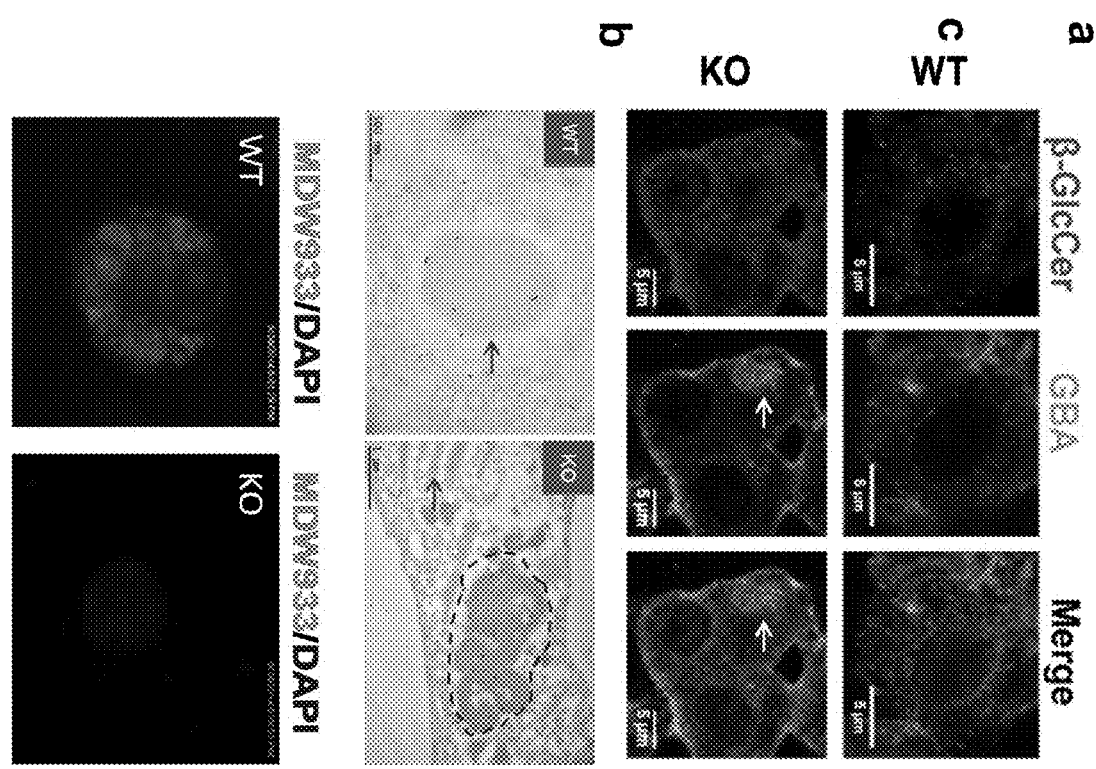
FIGS. 12A-12C. (A) Distribution of GBA is altered accompanied with β-GlcCer accumulation in PGRN KO mice. Frozen sections of lung tissue from OVA-challenged WT and PGRN KO mice were stained with GBA and β-GlcCer antibodies by immunofluorescence. The aggregation of GBA is indicated with an arrow. (B) GBA is aggregated in the cytoplasm in PGRN null macrophage, assayed by immunogold labeling of lung tissue. GBA is expressed in lysosome, indicated by an arrow, in WT macrophage (left panel 53,000×), while GBA is absent in tubular-like lysosome, and GBA is aggregated in the macrophage of PGRN KO mice (right panel, 25,000×). A aggregation region of denser immunogold labeling is circled with a dashed line. (C) Lysosomal GBA is undetectable in PGRN deficient macrophages, assayed with activity-based probe MDW933. BMDMs from WT and PGRN KO mice pre-stimulated with lipid mixture was labelled with 50 nM MDW933 for 2 hours, followed by fixation and DAPI staining, and the images were taken under confocal microscope.
Figure 28:
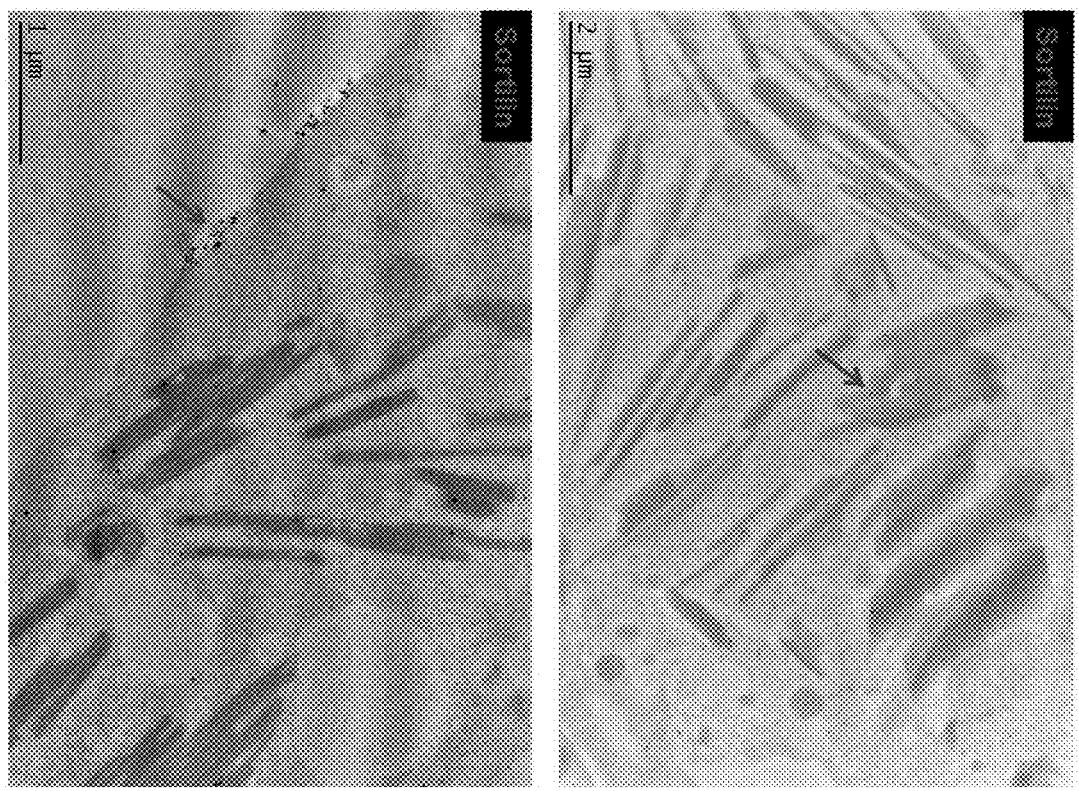
FIG. 28. Distribution of Sortilin is normal in PGRN null macrophages. PGRN KO mice were challenged with OVA, and lung were fixed and processed for transmission electronic microscope. Expressions of Sortilin were stained by Sortilin antibody, followed by gold-labeled secondary antibody. The distribution of Sortilin is normal in Gaucher cells in PGRN KO mice, mainly expressed in tubular-like lysosomes (upper panel), and some expressed on the cell surface to mediate endocytosis (lower panel).
Figure 30:
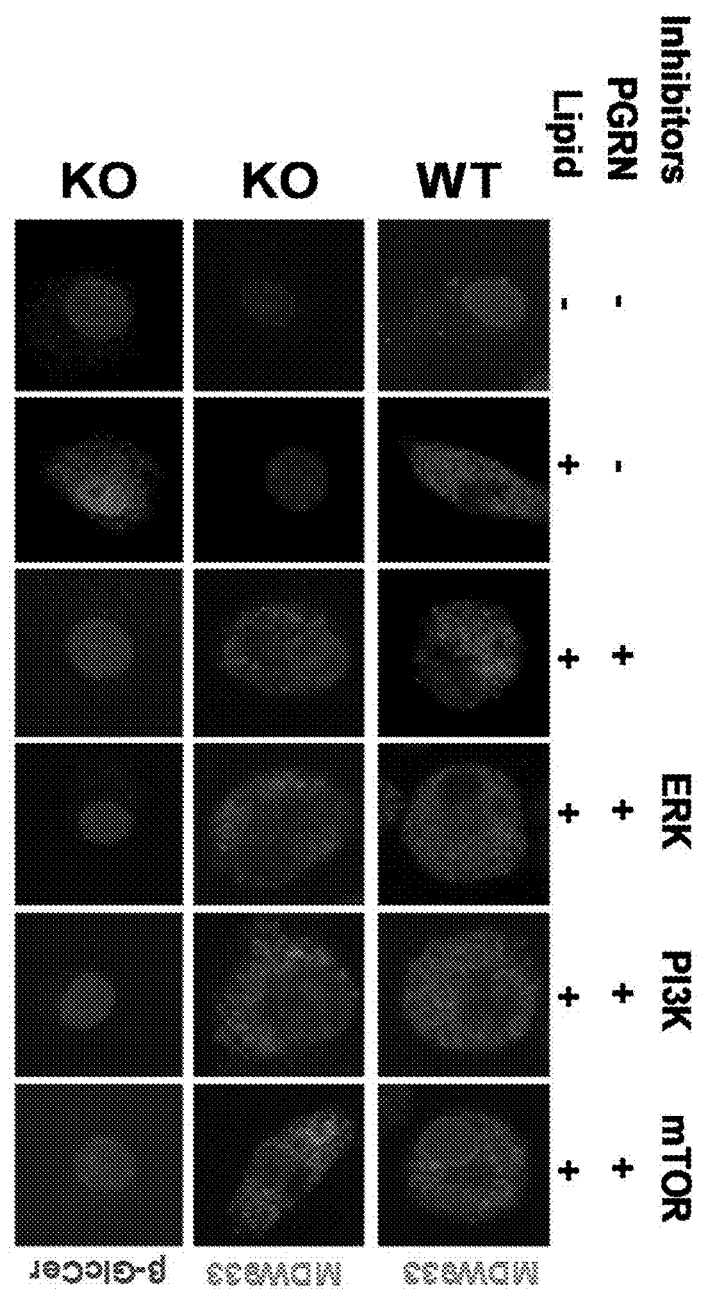
FIG. 30. rPGRN's effect on β-GlcCer clearance is independent of ERK, PI3K and mTOR signaling pathways. WT and PGRN KO BMDMs were stimulated lipid mixture (5 µg/ml) for 2 days, in the presence or absence of 0.4 µg/ml rPGRN protein with or without kinase inhibitors of ERK, PI3K and mTOR pathways, as indicated. The cells were labeled with MDW933 for 2 hours, then the cells were fixed and mounted with DAPI-medium. The MDW933-labelled lysosomal GBA was visualized by the intensity of green fluorescence under confocal microscope, and the accumulation of β-GlcCer was stained with β-GlcCer antibody (red) by immunofluorescence staining.

GBA and its Transport Receptor LIMP2 are Aggregated in the Cytoplasm and Absent in the Lysosome of PGRN-Deficient Macrophage We next sought to determine the mechanism underlying PGRN-null induced GD-like phenotype by evaluating GBA activity and expression. Accumulation of β-GlcCer in GD is caused by reduced GBA enzymatic activity or decreased GBA protein expression[20]. To our surprise, both GBA enzymatic activities and protein expression were normal in PGRN KO mice, actually the GBA expression was slightly increased after OVA challenge in PGRN KO mice (FIG. 11A, 11B). Although the protein level and activity of GBA were not decreased, immunohistochemistry staining of GBA revealed that GBA cellular distribution was dramatically altered. GBA was distributed in the cytoplasm of the macrophage in WT mice, while GBA expression was aggregated in the cytoplasm in PGRN KO mice (FIG. 11C). In contrast, the cellular distribution of alpha-galactosidase A (GLA), a lysosomal enzyme that is primarily delivered to lysosome via a mannose-6-phosphate receptor-dependent pathway[27], was not affected in PGRN deficient cells (FIG. 11C). Confocal staining with frozen sections of lung tissues confirmed that GBA was aggregated, accompanied with β-GlcCer accumulation in PGRN deficient tissues (FIG. 12A). Immunogold labeling TEM also demonstrated that GBA was aggregated in the cytoplasm in Gaucher-like cells, and GBA was absent in the tubular-like lysosomes in PGRN null macrophages, while GBA was detectable in lysosomes in WT macrophages (FIG. 12B). As a control for the immunogold labeling TEM, Sortilin was found mainly to be clustered close to the cell membrane, mediating endocytosis, and was present in the tubular-like lysosomes of Gaucher cells in PGRN KO mice (FIG. 28) To further visualize the defect of GBA lysosomal appearance in PGRN KO macrophages, we employed the activity-based probe (ABP) MDW933, which can spontaneously cross membranes and allow sensitive and specific labeling of active lysosomal GBA in living cells[28-30]. This probe failed to detect GBA in PGRN deficient BMDMs, although it efficiently labelled lysosomal GBA in WT BMDMs (FIG. 12C, FIG. 30). In addition, recombinant PGRN rescued the lysosomal appearance of GBA in PGRN-deficient macrophages (FIG. 30). Taken together, these results demonstrate that the delivery of GBA to the lysosome depends on the presence of PGRN.

Figure 13:
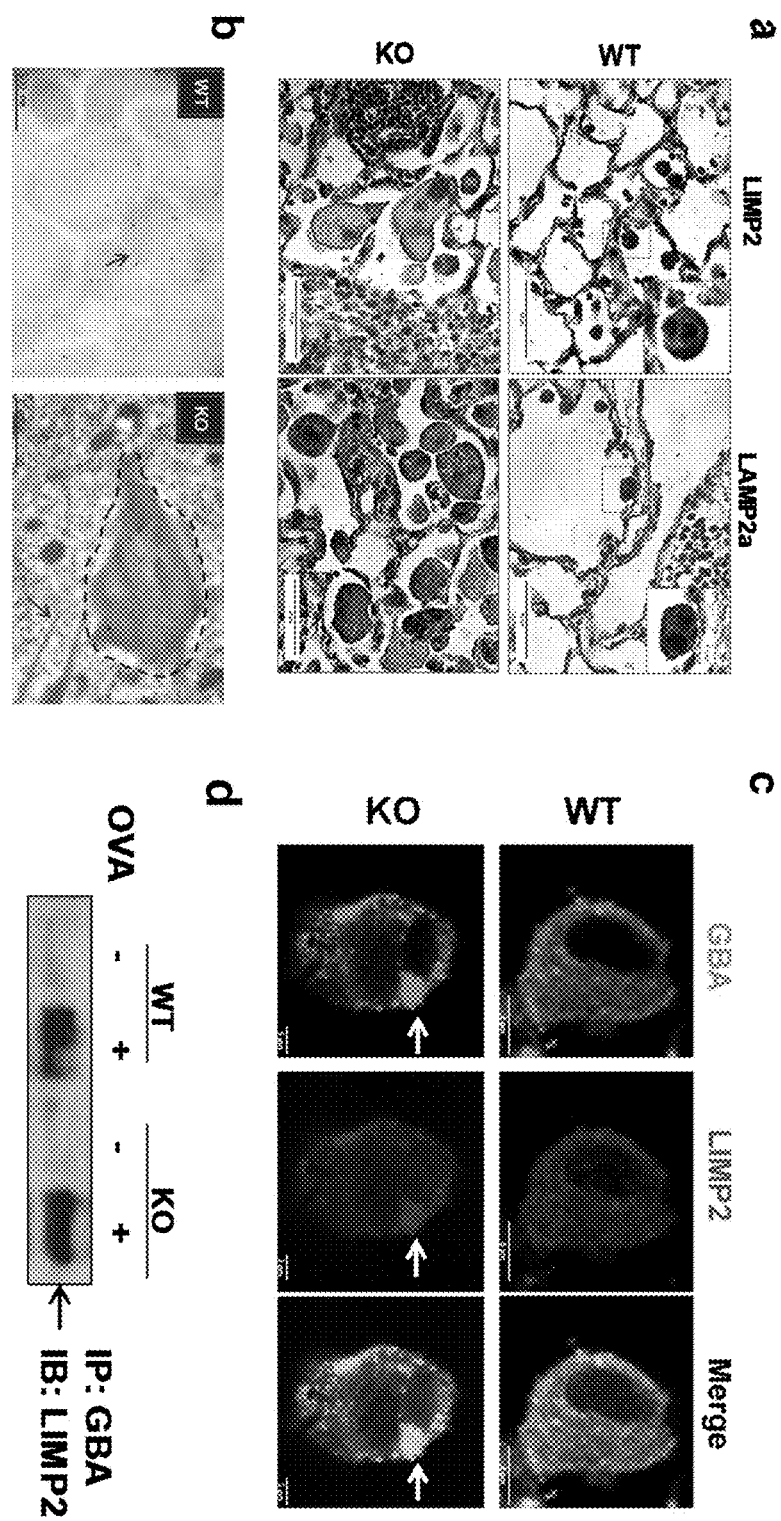
FIGS. 13A-13D. (A) Expression of LIMP2 and LAMP2 in macrophages from WT and PGRN KO mice. Paraffin-embedded lung slides from WT and PGRN KO mice were stained with LIMP2 and LAMP2 by immunohistochemistry. Aggregation of LIMP2 in PGRN KO macrophages was indicated with an arrow. (B) LIMP2 is not detectable in lysosome, and aggregated in the cytoplasm in PGRN null macrophage, assayed by immunogold labeling of lung tissue. LIMP2 is detectable in the lysosome, indicated with an arrow, of WT macrophage (left panel, 53,000×), whereas it is aggregated in the cytoplasm of PGRN-null macrophage and not observed in the tubular-like lysosome (right panel 31,000×). A aggregation region of denser immunogold labelling is circled with a dashed line. (C) Aggregated GBA and aggregated LIMP2 co-localize in PGRN KO macrophages. Frozen sections of lung tissues of WT and PGRN KO mice were stained with GBA and LIMP2 antibodies, the distribution of GBA and LIMP2 was assayed by immunofluorescence staining and imaged by confocal microscope. The aggregated region is indicated with an arrow. (D) GBA binds to LIMP2 in the absence of PGRN in vivo, assayed by co-immunoprecipitation (Co-IP). Lung tissue from both WT and PGRN KO mice were lysed and protein complexes were immunoprecipitated with anti-GBA antibody and detected with anti-LIMP2 antibody.

Lysosomal integral membrane protein 2 (LIMP2), a lysosomal marker, was reported to function as a GBA-binding receptor that mediated the delivery of GBA to lysosomes[31, 32]. Interestingly, we found that lysosomal delivery of LIMP2 was also defective in PGRN-deficient macrophages (FIG. 13A, 13B). However, cellular distribution of lysosomal associated membrane protein-2 (LAMP-2), another lysosomal marker, was not affected in PGRN null macrophages. Specifically, both LIMP2 and LAMP2 were distributed in the cytoplasm of WT macrophage; however the expression of LIMP2 was aggregated in the cytoplasm in PGRN null macrophages, while LAMP2 was distributed in PGRN KO macrophage (FIG. 13A). The aggregation of LIMP2 was further confirmed with immunogold TEM staining (FIG. 13B). In addition, both GBA and LIMP2 co-localized in the aggregate in PGRN KO macrophage (FIG. 13C) and still bound to each other in vivo (FIG. 13D). Collectively, lysosomal delivery of both GBA and its receptor LIMP2 was defective in PGRN deficient mice. LIMP2 deficiency has been reported to cause increased secretion of GBA[31], however, no significant difference in GBA secretion was observed between wildtype and PGRN-deficient cells, although PGRN deletion, similar to LIMP2 deficiency[31], also led to the absence of GBA in lysosomes.

Figure 14:
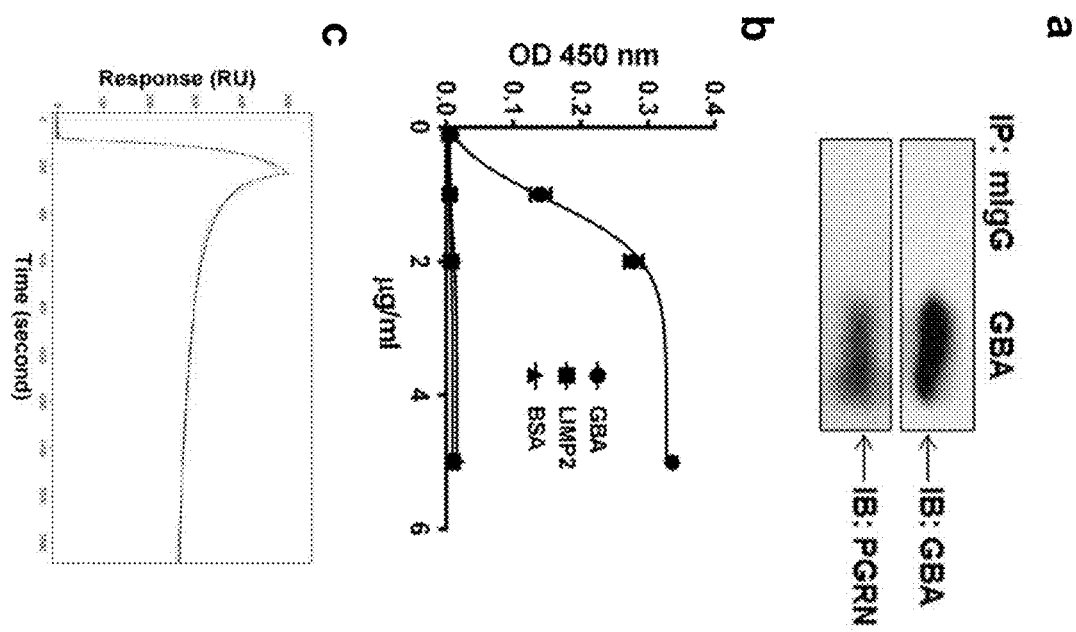
FIGS. 14A-14C. Molecular pathway by which PGRN mediates lysosomal delivery of GBA. (A) PGRN binds to GBA in vivo, assayed by co-immunoprecipitation (Co-IP). Lung tissue from WT mice were lysed and protein complexes were immunoprecipitated with anti-GBA antibody and detected with anti-PGRN antibody. (B) PGRN directly binds to GBA in vitro, assayed by solid phase binding assay. Various amounts of PGRN were coated, and biotin-labeled BSA and GBA were added, followed by HRP-labeled Streptavidin and its substrates. (C) PGRN binds to GBA with a high affinity $K_D$ of 0.71 nM, assayed by surface plasmon resonance (SPR) with COOH1 chips.

PGRN is an Essential Co-Chaperone of the HSP70 Chaperone Pathway that Mediates GBA/LIMP2 Lysosomal Delivery The finding that PGRN was required to target GBA to lysosome prompted us to determine whether PGRN associated with GBA. In vivo interaction between PGRN and GBA was demonstrated by co-immunoprecipitation by using GBA antibody to immunoprecipitate the protein complex and probing with PGRN antibody (FIG. 14A). We next determined whether PGRN directly binds to GBA using a solid-phase binding assay with recombinant PGRN and GBA. PGRN demonstrated dose-dependent binding and saturation to liquid-phase GBA (FIG. 14B), whereas no direct interaction between PGRN and LIMP2 was detected (FIG. 14B). The binding affinity between PGRN and GBA was then measured using surface plasmon resonance (SPR) with SensiQ Pioneer as described[13,14]. The results demonstrated that PGRN binds to GBA with a very high affinity ($K_D$=0.71 nM) (FIG. 14C), higher than PGRN's affinity to Sortilin ($K_D$=3.67 nM) (not shown), a known PGRN-binding lysosomal receptor[26].

Figure 31:
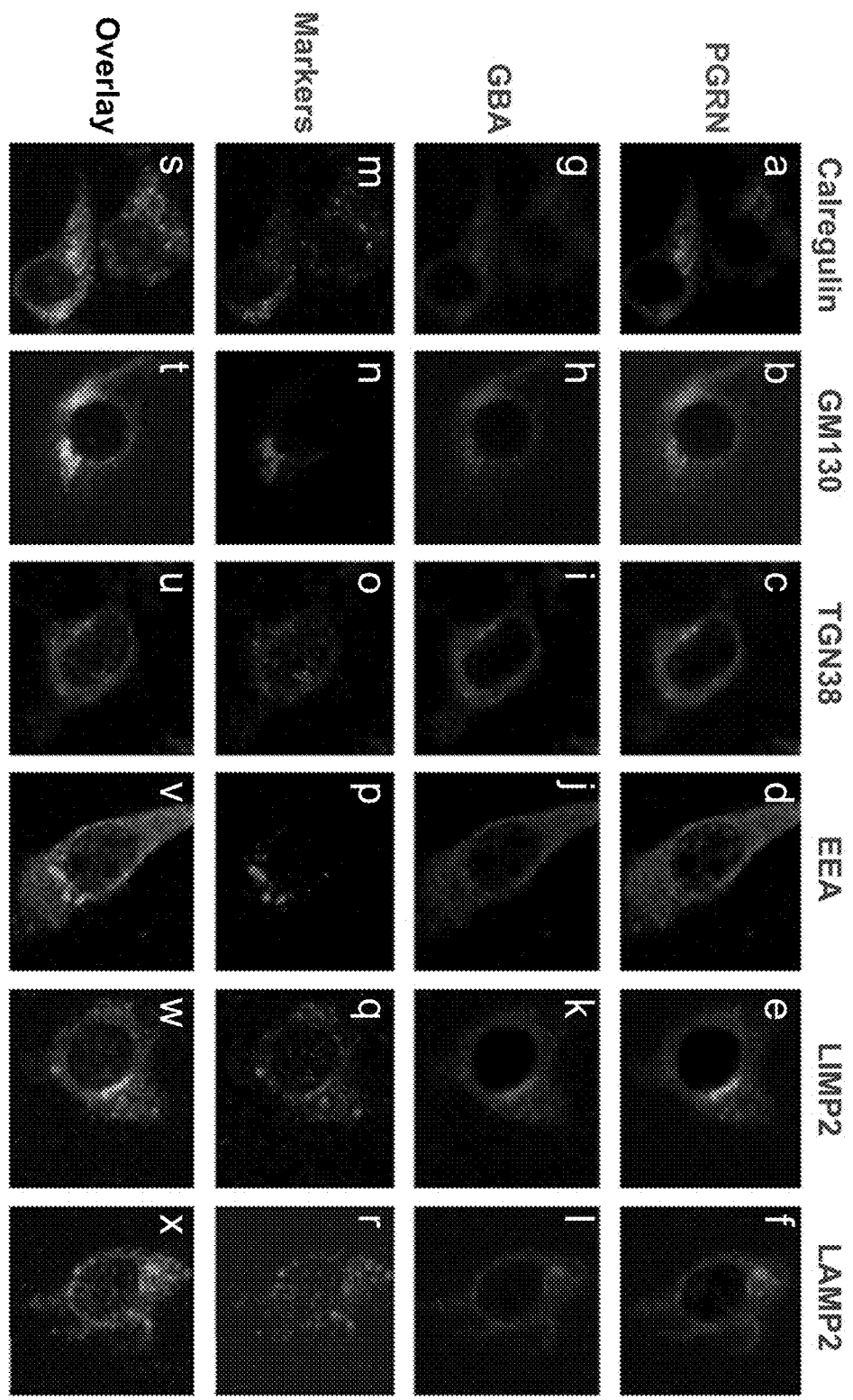
FIG. 31. Co-localization of GBA and PGRN in the intracellular trafficking compartments in macrophages. BMDMs from WT mice were fixed and the expressions of PGRN and GBA, as well as the markers for the trafficking compartments were detected with respective specific primary antibodies, followed by corresponding secondary antibodies labeled with different fluorescence dyes. PGRN was stained with sheep anti-mouse PGRN primary antibody and secondary antibody labeled with Alexa-488 (a-f), GBA was stained with rabbit anti-mouse primary antibody, followed by Cy3-labeled secondary antibody (g-l), and the markers for the trafficking compartments (Calregulin, GM130, TGN38, EEA1, LIMP2, and LAMP2) were stained with corresponding mouse-originated primary antibodies, and followed by Alexa-647 labeled secondary antibodies (m-r). Panels s-x are the merged images of 4-color staining. The nucleus was stained with DAPI (blue).
Figure 32:
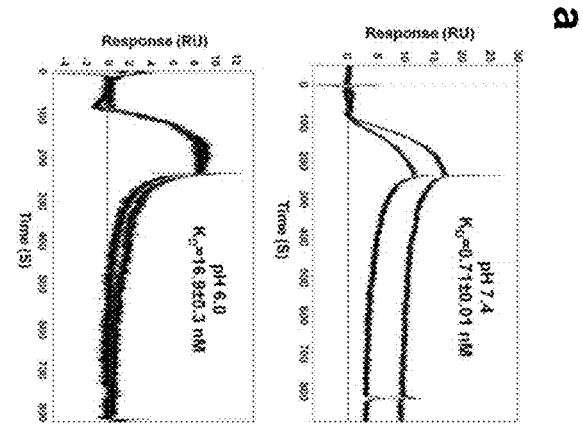
FIG. 32. Effects of pH on the binding of GBA to PGRN. (a) The direct interactions between GBA and PGRN at various pH, as indicated, were detected by SPR at SensiQ Technologies Inc. by using COOHV1 chip. (b) Effect of Assay pH on Kinetic Binding Values.
Figure 32:
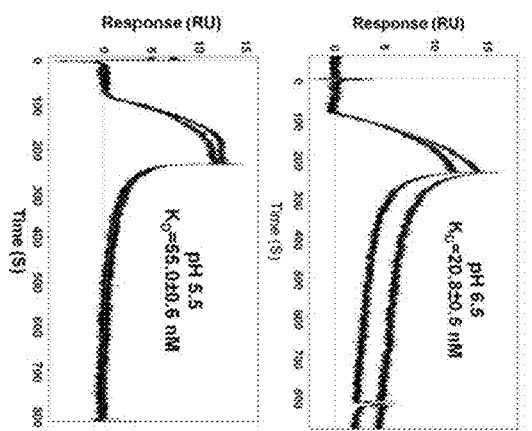
Figure 32:
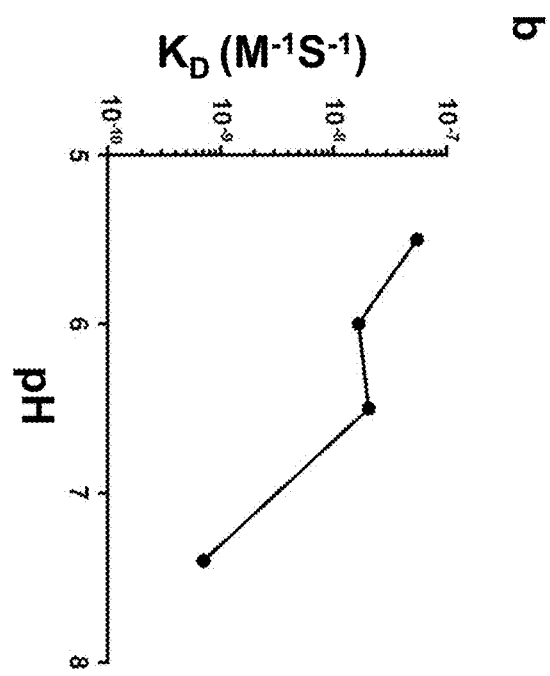

Four-color immunofluorescence staining revealed that GBA and PGRN co-localize in the intracellular traffic compartments of macrophages, including endoplasmic reticulum (ER), Golgi, and trans-Golgi network (TGN) (FIG. 31). GBA/PGRN passes through intracellular compartments of varying pH en route from ER to lysosomes[31]. The direct binding affinity of GBA to PGRN over a range of pH values was also tested using SensiQ Pioneer (FIG. 32A). Similar to the interaction between GBA and LIMP2[31], binding of GBA to PGRN was favored at neutral pH, and there was a trend toward decreased affinity with decreasing pH (FIG. 32B). Taken together, these results suggested that the probable points of GBA and PGRN association are prelysosomal, possibly beginning in compartments as early as the ER and Golgi apparatus.

Figure 15:
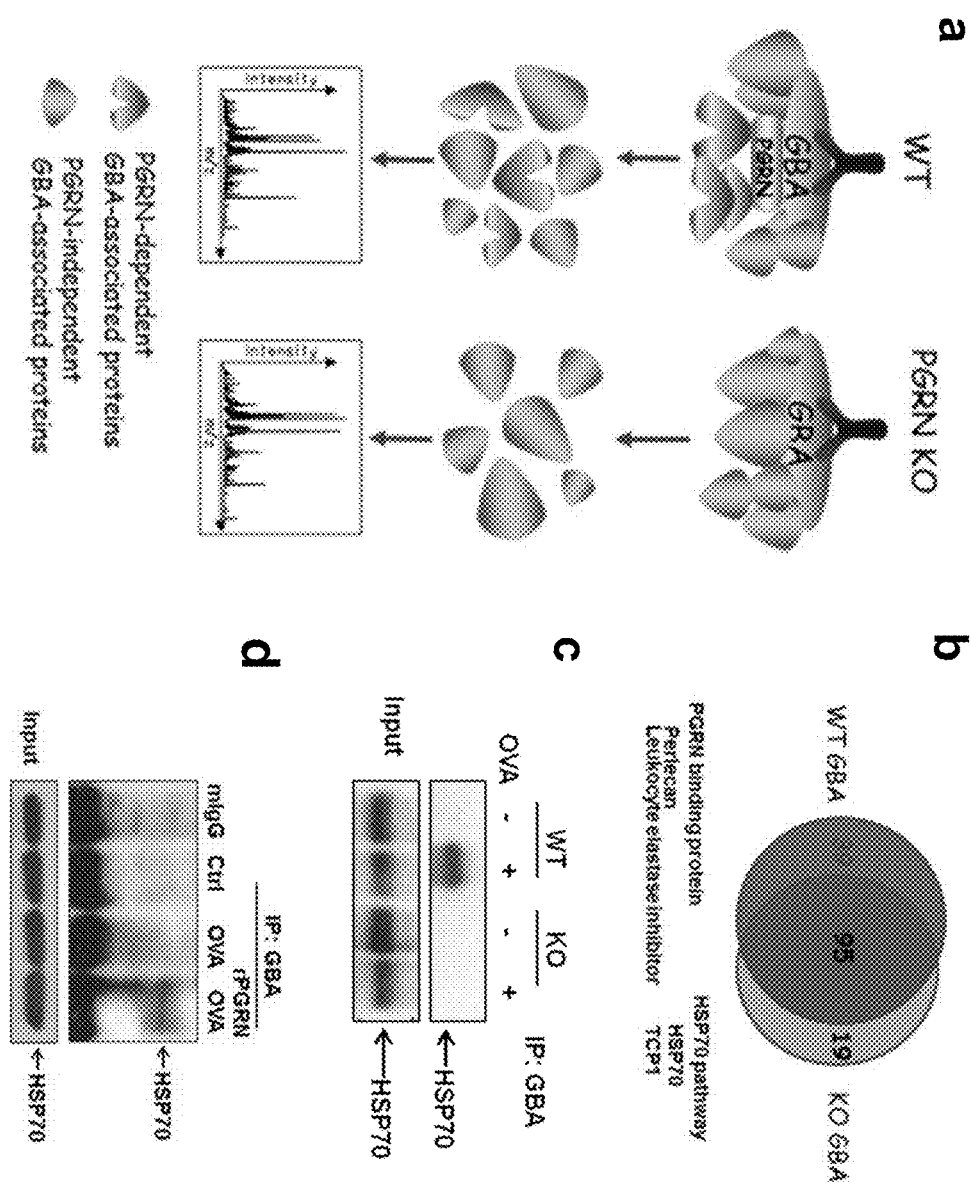
FIGS. 15A-15D. (A) The scheme of the method used to identify potential molecules involved in PGRN-mediated delivery of GBA to lysosomes, i.e. PGRN-dependent GBA associated proteins. Immunoprecipitation was performed with GBA antibody from both WT and PGRN KO mice, followed by high-sensitivity mass spectrum. (B) Summary of the hits isolated from both WT and PGRN KO mice and the identification of HSP70-mediated trafficking as a PGRN-dependent GBA-associated pathway. (C) Binding of GBA to HSP70 is PGRN-dependent. Immunoprecipitation was conducted with anti-GBA antibody in WT and PGRN KO mice, and probed with HSP70 antibody. (D) rPGRN restores the interaction between GBA and HSP70 in PGRN deficient mice in vivo. Lung tissue lysate prepared from OVA-unchallenged (Ctrl), OVA-challenged PGRN KO mice treated with or without rPGRN was immunoprecipitated with anti-GBA antibody, and the presence of HSP70 in immunoprecipitated complex probed with HSP70 antibody.

We next sought to determine the molecular pathway by which PGRN regulates GBA. To isolate the molecules that are involved in PGRN regulation of GBA, immunoprecipitation was performed with GBA antibody from both WT and PGRN KO tissues, followed by high-sensitivity mass spectrometry (MS). Immunoprecipitation with GBA antibody pulled-down both PGRN-dependent and PGRN-independent GBA-associated proteins in WT tissues. When the same immunoprecipitation experiment was performed in PGRN KO tissues, only PGRN-independent GBA-associated proteins were immunoprecipitated. Hits from WT mice were subtracted by hits from PGRN KO, to yield PGRN-dependent GBA associated proteins, with the rationale that the molecules involved in PGRN-mediated GBA delivery would be among the hits only present in WT mice but not PGRN KO mice (FIG. 15A). 134 hits in WT mice and 114 hits in PGRN KO mice were identified. 95 of them were common in both groups, and 39 proteins were found to be specific for WT mice, suggesting these proteins would be PGRN-dependent GBA-associated proteins (FIG. 15B). Perlecan and Leukocyte elastase inhibitor, two known PGRN-binding proteins[7,33], were identified among the 39 hits, validating the technique. In addition, HSP70 and its co-chaperone protein TCP1, as well as cytoskeleton, vesicle-traffic related proteins, and an energy producing enzyme, were among the 39 hits.

TABLE 3

GENES THAT MAY BE PGRN-DEPENDENT GBA ASSOCIATED PROTEINS

Perlecan (Heparan sulfate proteoglycan 2) OS = Mus musculus GN = Hspg2 PE = 4 SV = 1 – [B1B0C7_MOUSE] *1
Moesin OS = Mus musculus GN = Msn PE = 1 SV = 3 – [MOES_MOUSE]
T-complex protein 1 subunit zeta OS = Mus musculus GN = Cct6a PE = 1 SV = 3 – [TCPZ_MOUSE] *2
Heat shock 70 kDa protein 12B OS = Mus musculus GN = Hspa12b PE = 1 SV = 1 – [HS12B_MOUSE] *2
Uncharacterized protein OS = Mus musculus GN = Gm8991 PE = 4 SV = 1 – [E9Q7H5_MOUSE]
EH domain-containing protein 4 OS = Mus musculus GN = Ehd4 PE = 1 SV = 1 – [EHD4_MOUSE]
Polymeric immunoglobulin receptor OS = Mus musculus GN = Pigr PE = 1 SV = 1 – [PIGR_MOUSE]
Leukocyte elastase inhibitor A OS = Mus musculus GN = Serpinb1a PE = 1 SV = 1 – [ILEUA_MOUSE] *1
Uncharacterized protein (Fragment) OS = Mus musculus GN = Fus PE = 4 SV = 1 – [G3UXT7_MOUSE]
Alpha-1-antitrypsin 1-2 OS = Mus musculus GN = Serpina1b PE = 1 SV = 2 – [A1AT2_MOUSE]
Protein S100-A9 OS = Mus musculus GN = S100a9 PE = 1 SV = 3 – [S10A9_MOUSE]
Vinculin OS = Mus musculus GN = Vcl PE = 1 SV = 4 – [VINC_MOUSE]
Clusterin OS = Mus musculus GN = Clu PE = 1 SV = 1 – [CLUS_MOUSE]
Putative ATP-dependent RNA helicase Pl10 OS = Mus musculus GN = D1Pas1 PE = 1 SV = 1 – [DDX3L_MOUSE]
Niban-like protein 1 OS = Mus musculus GN = Fam129b PE = 1 SV = 2 – [NIBL1_MOUSE]
Serotransferrin OS = Mus musculus GN = Tf PE = 1 SV = 1 – [TRFE_MOUSE]
Annexin A11 OS = Mus musculus GN = Anxa11 PE = 1 SV = 2 – [ANX11_MOUSE]
Ankycorbin OS = Mus musculus GN = Rai14 PE = 1 SV = 1 – [RAI14_MOUSE]
Ehd2 protein OS = Mus musculus GN = Ehd2 PE = 2 SV = 1 – [Q8R2X0_MOUSE]
Peroxiredoxin 1 (Fragment) OS = Mus musculus GN = Prdx1 PE = 4 SV = 1 – [B1AXW5_MOUSE]
LIM and SH3 protein 1 (Fragment) OS = Mus musculus GN = Lasp1 PE = 4 SV = 1 – [A2A6G9_MOUSE]
Ribonuclease inhibitor OS = Mus musculus GN = Rnh1 PE = 1 SV = 1 – [RINI_MOUSE]
Heterogeneous nuclear ribonucleoprotein U, isoform CRA_b OS = Mus musculus GN = Hnrnpu PE = 4 SV = 1 – [G3XA10_MOUSE]
Fibrinogen beta chain OS = Mus musculus GN = Fgb PE = 2 SV = 1 – [FIBB_MOUSE]
NK13 OS = Mus musculus GN = Serpinb6b PE = 2 SV = 2 – [O08804_MOUSE]
Chloride intracellular channel protein 4 OS = Mus musculus GN = Clic4 PE = 1 SV = 3 – [CLIC4_MOUSE]
Dimethylaniline monooxygenase [N-oxide-forming] 2 OS = Mus musculus GN = Fmo2 PE = 1 SV = 3 – [FMO2_MOUSE]
Ceruloplasmin, isoform CRA_f OS = Mus musculus GN = Cp PE = 4 SV = 1 – [G3X9T8_MOUSE]
Myosin light polypeptide 6 OS = Mus musculus GN = Myl6 PE = 1 SV = 3 – [MYL6_MOUSE]
Fibrinogen, alpha polypeptide OS = Mus musculus GN = Fga PE = 2 SV = 1 – [Q99K47_MOUSE]
Alcohol dehydrogenase 1 OS = Mus musculus GN = Adh1 PE = 2 SV = 2 – [ADH1_MOUSE]
Isoform 4 of Myosin-XVIIIa OS = Mus musculus GN = Myo18a – [MY18A_MOUSE]
Copine-3 OS = Mus musculus GN = Cpne3 PE = 1 SV = 2 – [CPNE3_MOUSE]
Pulmonary surfactant-associated protein D OS = Mus musculus GN = Sftpd PE = 2 SV = 1 – [SFTPD_MOUSE]
Actin-related protein 2/3 complex subunit 1B OS = Mus musculus GN = Arpc1b PE = 1 SV = 4 – [ARC1B_MOUSE]
F-actin-capping protein subunit alpha-1 OS = Mus musculus GN = Capza1 PE = 1 SV = 4 – [CAZA1_MOUSE]
Integrin beta OS = Mus musculus GN = Itgb2 PE = 2 SV = 1 – [Q54218_MOUSE]
Fibrinogen gamma chain OS = Mus musculus GN = Fgg PE = 2 SV = 1 – [FIBG_MOUSE]

TABLE 3-continued

GENES THAT MAY BE PGRN-DEPENDENT GBA ASSOCIATED PROTEINS

Long-chain specific acyl-CoA dehydrogenase, mitochondrial OS = Mus musculus GN = Acadl PE = 2 SV = 2 – [ACADL_MOUSE]

Note:
*1 known PGRN binding proteins,
*2 HSP70 and its co-chaperones

Figure 16:
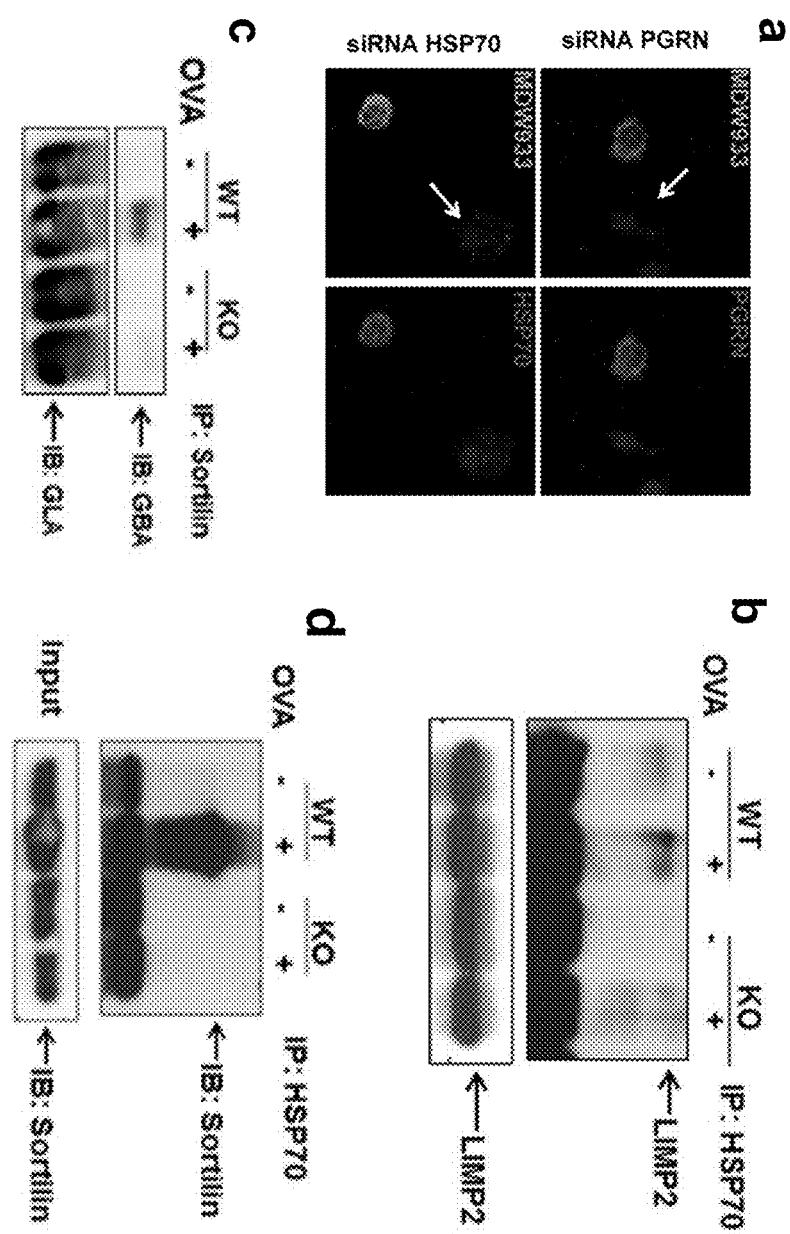
FIGS. 16A-16D. (A) Suppression of PGRN and HSP70 via a siRNA approach markedly reduces the lysosomal GBA in macrophage. RAW264.7 macrophages were transfected with siRNA specifically against PGRN or HSP70, and the cells pre-stimulated with lipid mixture were labelled with MDW933 probe for 2 hours, and the expression levels of PGRN and HSP70 measured by immunofluorescence staining. The cell transfected with corresponding siRNA is indicated with an arrow. (B) Binding of LIMP2 to HSP70 is also PGRN-dependent. Immunoprecipitation was conducted with anti-HSP70 antibody in WT and PGRN KO mice, and probed with LIMP2 antibody. (C) Binding of GBA, but not GLA, to Sortilin is PGRN-dependent. Immunoprecipitation was performed with anti-Sortilin antibody in WT and PGRN KO mice, and detected with either GBA or GLA antibody. (D) Binding of HSP70 to Sortilin is also PGRN-dependent. Immunoprecipitation was performed with anti-HSP70 antibody in WT and PGRN KO mice, and detected with Sortilin antibody.

These data were followed up with studies in HEK293EBAN cells stably transfected with an expression plasmid encoding His-tagged PGRN[13]. Two proteins were co-purified with His-tagged PGRN, and MS analysis revealed that these were HSP70 and TCP1 (not shown). To confirm the MS data, we conducted immunoprecipitation using a GBA antibody in WT and PGRN KO tissues, and probed with an antibody against HSP70. HSP70 bound to GBA in WT mice after OVA challenge, and this interaction was undetectable in PGRN KO mice (FIG. 15C). In addition, administration of rPGRN efficiently rescued the binding of GBA to HSP70 in PGRN KO mice (FIG. 15D). We next examined whether HSP70 is required for the lysosomal delivery of GBA, and HSP70 was suppressed using an siRNA approach. Similar to knockdown of PGRN (serving as a control), suppression of HSP70 led to undetectable lysosomal GBA, assayed with MDW933 labeling in living cells (FIG. 16A).

Previous reports that LIMP2 was the major GBA transport receptor[31,34,35], together with the finding that both GBA and LIMP2 were aggregated in PGRN deficient macrophages (FIG. 13), led us to determine whether HSP70 also interacted with LIMP2. Similar to GBA, LIMP2 also associated with HSP70 in WT but not in PGRN KO tissues (FIG. 16B). Sortilin was reported to be a receptor of PGRN and to mediate the delivery of PGRN to the endosome/lysosomal pathway in neurons[26]. We thus determined whether Sortilin forms a ternary complex with LIMP2/GBA/PGRN/HSP70 through PGRN as a linker protein and facilitates the delivery of LIMP2/GBA/PGRN/HSP70 along the endosome/lysosomal pathway. Here we found that this was the case. The interaction between Sortilin and GBA was identified in WT lungs after OVA challenge, which was completely lost in PGRN KO lungs, while the interaction between Sortilin and GLA[27] was not affected by deficiency of PGRN (FIG. 16C). In addition, Sortilin very weakly associated with HSP70 in untreated WT lungs, and this interaction was markedly enhanced by OVA challenge (FIG. 16D), while this interaction was also completely abolished in PGRN KO lungs (FIG. 16D). Collectively, Sortilin associates with LIMP2/GBA/PGRN/HSP70 complex through PGRN as an indispensible adaptor.

The finding that PGRN acts as a co-chaperone of HSP70 pathway required for GBA folding and trafficking, together with the facts that (1) chaperone-based treatments aiming to enhance GBA trafficking have proven to be an effective alternative to ERT (enzyme replacement treatment) for GD[36], and (2) recombinant HSP70 has been shown to effectively correct altered lysosomal stability seen in Niemann-Pick disease (NPD)[37], prompted us to examine whether PGRN would have therapeutic effects in GDs and other LSDs. Using the similar lysotracker approach[37], we examined the effects of rPGRN on fibroblasts from normal and 11 different patient fibroblasts of LSDs, including GDs. As expected, PGRN effectively reverted the altered lysosomes in fibroblasts from both Type I and II GD with or without lipid stimulation (FIG. 33A, 33B). We were excited to observe that PGRN also remarkably normalized the altered lysosomes in fibroblasts of Tay-Sachs disease, Farber disease, and Mucolipidosis III (FIG. 33A, 33B). In line with these findings, the accumulation of GAG and M2 ganglioside was also observed in the tissues from aged PGRN deficient mice (data not shown). In the case of type III GD, Mucopolysacharidosis III and VI, PGRN demonstrated beneficial effects in the presence of lipid stimulation (FIG. 34A, 34B). Although PGRN corrected the diseased lysosomes from LSDs aforementioned in the single patient disease sample fibroblasts we initially evaluated, significant improvements were not observed on fibroblasts in our samples from Niemann-Pick disease type B, Fabry disease and Mucolipidosis VI (FIG. 35A, 35B). However, in view of the small sample size, further studies are planned with additional samples to evaluate PGRN effects in these latter diseases, as a conclusion of no significant effects cannot yet be made. Taken together, these results implicate PGRN, as a co-chaperone of HSP70 trafficking pathway, as involved in the lysosomal delivery of other lysosome enzymes in addition to GBA.

Discussion

Figure 36:
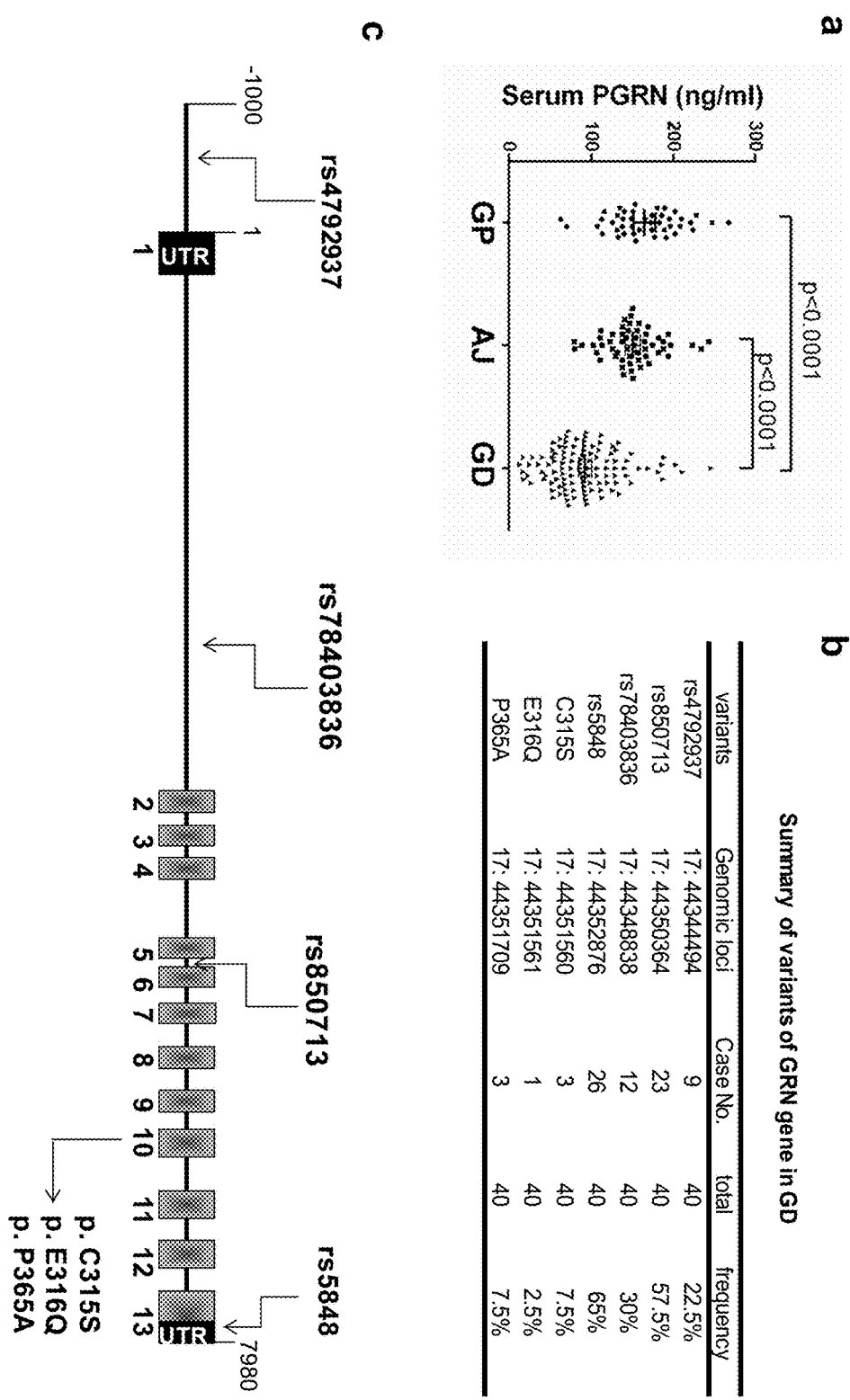
FIGS. 36A-36C. GD patients have decreased serum level of PGRN and GRN variants were identified in GD patients. (A) Serum levels of PGRN is significantly lower in GD patients. Serum levels of PGRN from 115 GD patients, 44 healthy controls from general population (GP), and 55 healthy control from Ashkenazi Jews (AJ) were measured by ELISA. GD patients have significant lower levels of PGRN (96.65±53.45 ng/ml) compared to healthy controls of GP (164.99±43.16 ng/ml), and healthy controls of AJ (150.64±33.9 ng/ml). The significance was tested by using one-way ANOVA, ($p<0.0001$). (B) Summary of GRN gene variants in 40 GD patients. Genomic DNA of 40 GD patients were used to amplify a 9-kb GRN gene DNA fragment covering 1-kb promoter region and 8-kb full-length GRN gene by high-fidelity PCR. DNA sequencing was performed by PacBio RS II Sequencing System at Genomic facility at Yale University. 4 SNP sites and 3 point mutations were identified in GD patients. (C) A diagram showing the positions of GRN variants identified in GRN gene.

PGRN-deficient mice were reported to exhibit accelerated lipofuscinosis and ubiquitination[11,12]. Here we report that PGRN null mice developed Gaucher-like disease, a finding that further supports the notion that PGRN may be a key regulator of lysosomes[26,38]. Both OVA-challenged adult and aged PGRN null mice demonstrated Gaucher-like cells and a typical tubular-like lysosomal appearance, which therefore presents a novel mouse model that closely mimics the signs of human GD[39]. This novel GD animal model not only helps us to better understand the pathogenesis of GD, but could also facilitate the testing and development of new drugs for treating GD. Neurons of the PGRN-deficient mice have been shown to accumulate lipofuscin and subunit c of mitochondrial ATP synthase (SCMAS) which are commonly regarded as neuronal ceroid lipofuscinosis (NCL) biochemical signatures[11,12]. The findings that PGRN deficient mice display both GD and NCL indicate the overlapping features of the phenotypes. We also observed the accumulation of lipofuscin and SCMAS in the brain of our mice models. Thus, the discrepancy among PGRN deficient mice models reported is probably resulted from the differences in the cell populations studied (Macrophages in GD vs Neurons in NCL). The unexpected development of GD-like in PGRN deficient mice models led us to examine whether PGRN level was also associated with human patients with GD. Indeed, serum PGRN levels of GD patients were significantly lower than both general healthy controls and also Ashkenazi Jewish controls, and several GRN gene variants were also identified in GD patients through whole GRN gene sequencing (FIG. 36).

Figure 33:
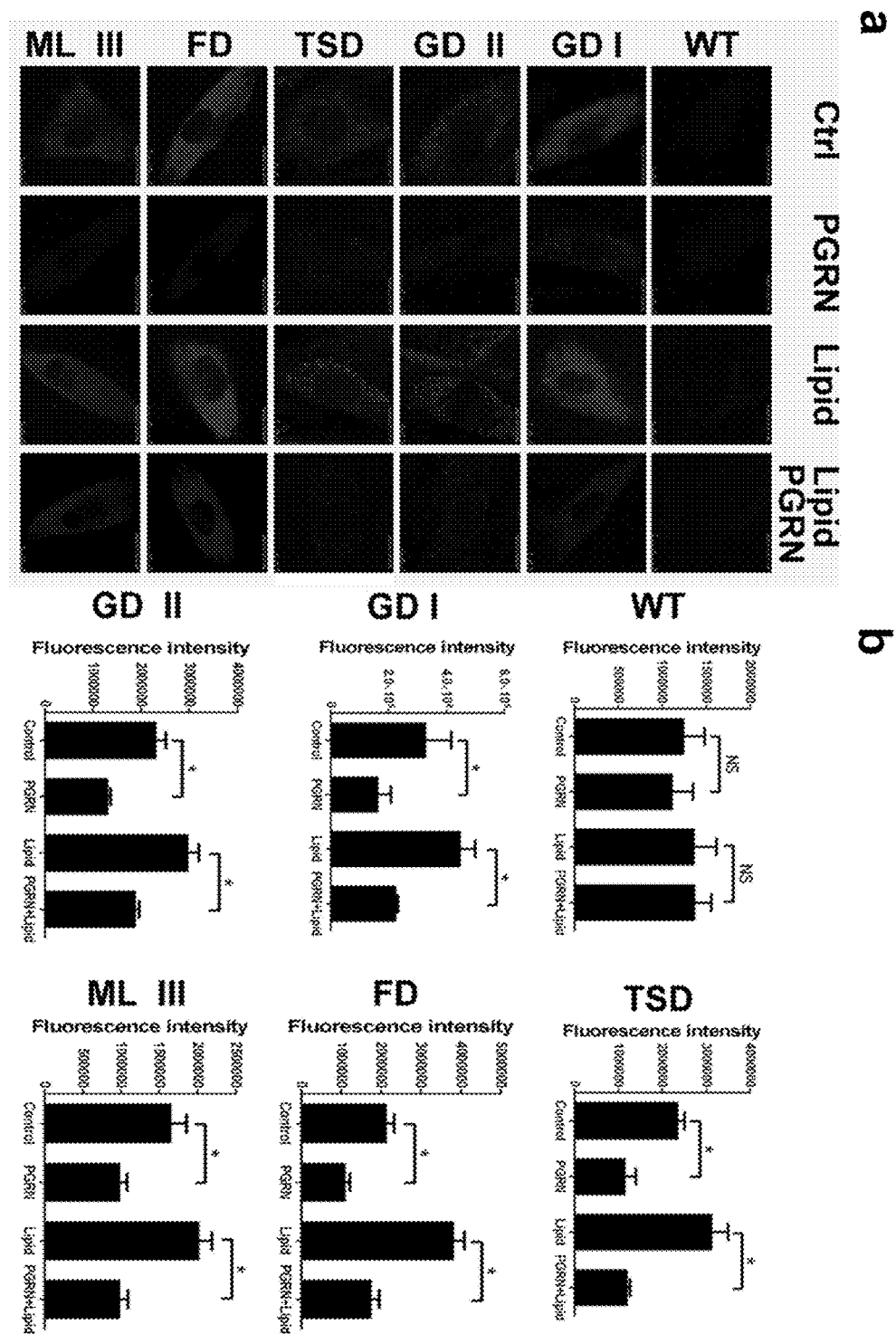
FIGS. 33A-33B. The effects of rPGRN on the diseased lysosomes in fibroblasts from various kinds of LSDs. Fibroblasts from healthy control and different LSDs were treated rPGRN protein (0.4 µg/ml), with or without lipid stimulation. The lysosomes were visualized by Lysotracker (A). (B) PGRN significantly corrects altered lysosomes in type I and II GD, Tay-Sachs disease, Farber disease, and Mucolipidosis type III with or without lipid stimulation.
Figure 34:
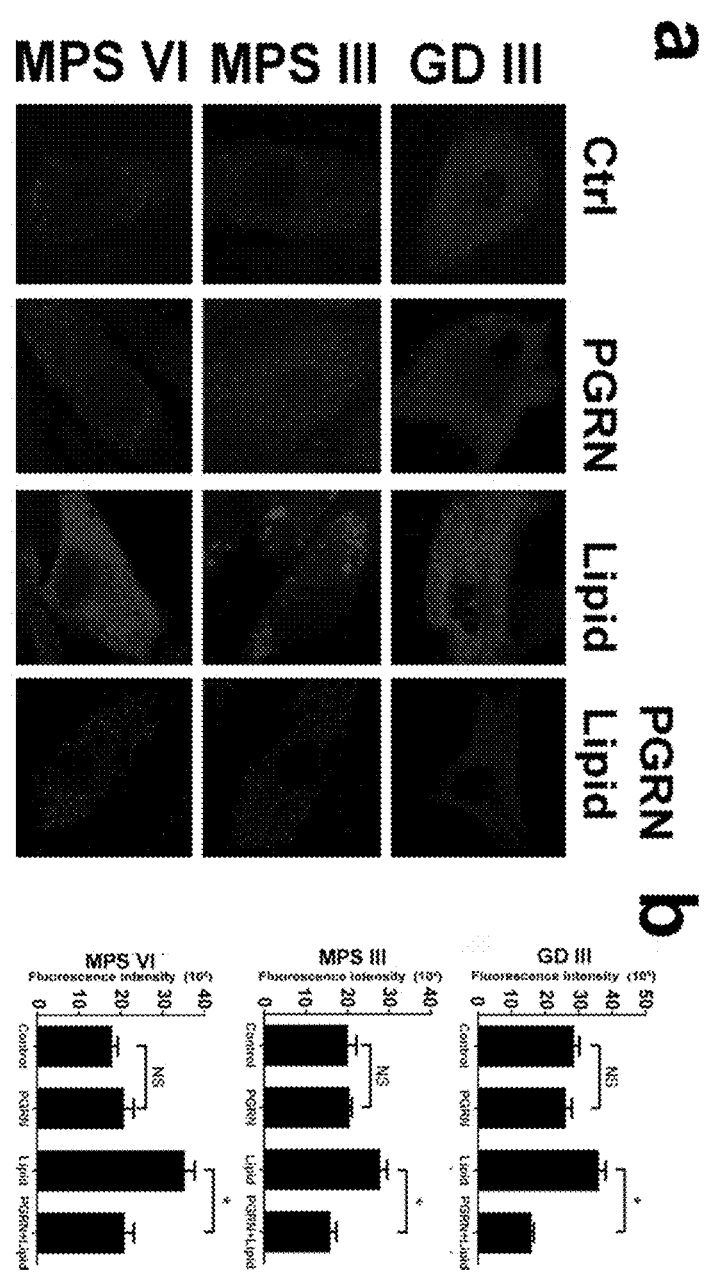
FIGS. 34A-34B. PGRN normalizes diseased lysosomes in type III GD, type III and VI mucopolysaccharidosis (MPS) only in the presence of lipid stimulation.
Figure 35:
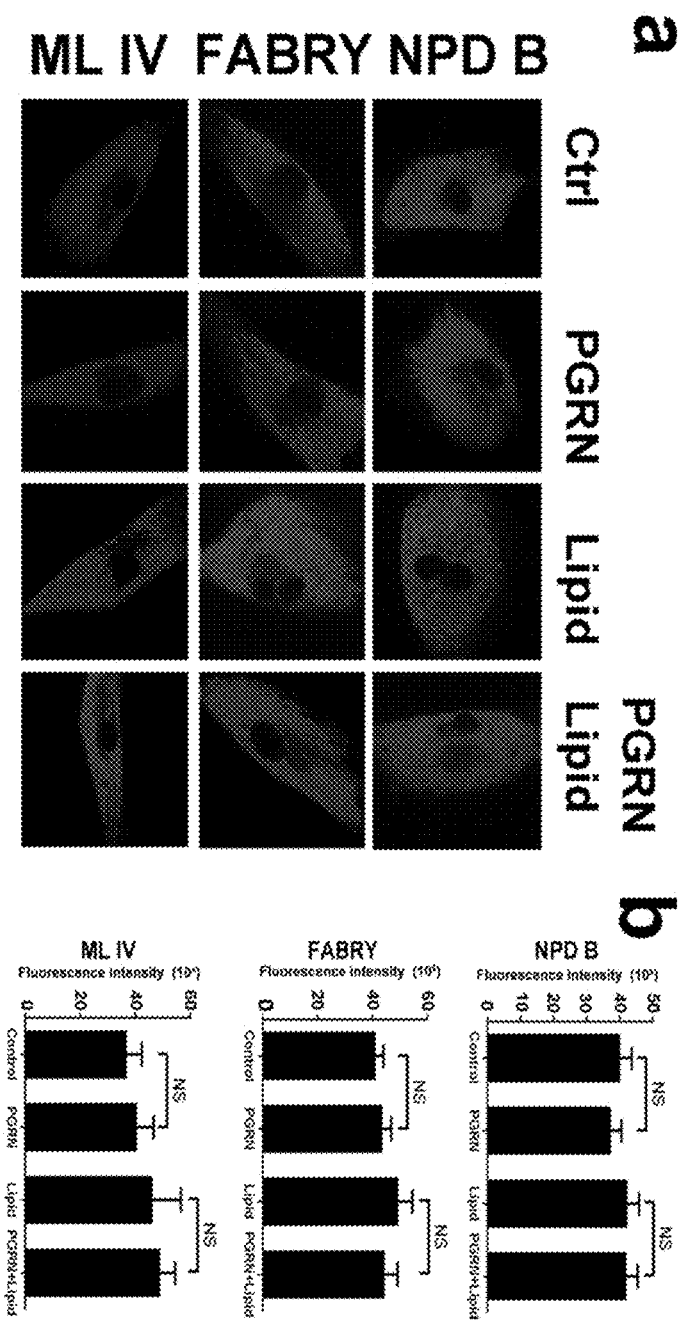
FIGS. 35A-35B. PGRN fails to revert lysosomes in Niemann-Pick disease type B (NPD B), Fabry disease, and type IV Mucolipidosis (ML) with or without lipid stimulation. Ten cells were randomly selected from every sample, and the fluorescence intensity of each cells were quantified by Image J software. Data are presented as mean values obtained from three independent experiments. The significance was tested by using one-way ANOVA (*$p<0.05$, **$p<0.01$, two sided).

HSP70 was isolated as one of numerous GBA-associated proteins dependent on the presence of PGRN in our unbiased screen. Interestingly, the associations of GBA with HSP70 as well as their involvements in GD were reported previously[36,40,41], although the nature of their association was unclear. In addition, the binding of PGRN to HSP70 was also recently reported[42]. Our approach identified PGRN as an essential component of GBA/PGRN/HSP70 ternary complex that mediates lysosomal delivery of GBA. Importantly, PGRN, acting as an essential co-chaperone for linking GBA to the HSP70-mediated folding and trafficking pathway, effectively normalized the altered lysosomes in the fibroblasts from GD patients. In addition, chaperone-based treatment aiming to facilitate GBA folding and trafficking has proven to be a promising approach for treating GD[36,43]. More importantly, current ERT is only effective for one LSD correspondingly, PGRN may be an alternative treatment for various kinds of LSDs in addition to GDs, as PGRN also significantly corrected diseased lysosomes of additional LSDs (FIGS. 33, 34, 35).

Figure 17:
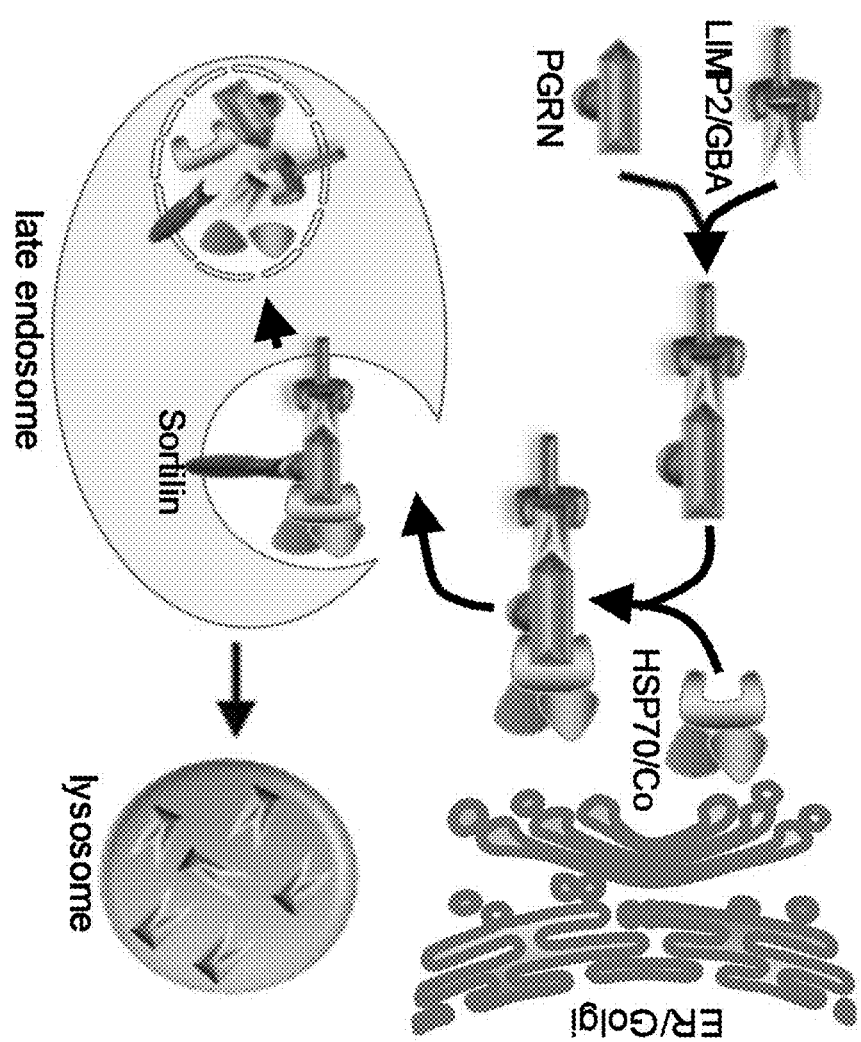
FIG. 17 depicts a proposed model explaining the role of PGRN in mediating the lysosomal delivery of GBA/LIMP2 through HSP70 chaperone pathway. Co stands for Co-chaperones.

LIMP2, the known GBA transport receptor[31,34,35], was also aggregated in PGRN deficient cells, and GBA-LIMP2 ligand-receptor constituted a ternary complex with PGRN and HSP70 chaperone, which requires PGRN as an adaptor. In addition, Sortilin, a PGRN-binding lysosomal receptor known to participate in the delivery of several proteins to the lysosome[26,27], also associated with this ternary complex through direct binding to PGRN. A proposed model for explaining the role of PGRN in mediating the folding and lysosomal delivery of LSD enzymes, exemplified with GBA/LIMP2, through an HSP70 chaperone pathway is shown in FIG. 17. GBA/LIMP2 associate with HSP70/co-chaperones in the ER/Golgi through PGRN as an essential adaptor, and transport simultaneously to lysosome. Other lysosomal receptors, such as Sortilin, may also facilitate the delivery of the complex to the endosome/lysosome. Additionally, the association with PGRN/HSP70 pathway may be also important for the folding of GBA and LIMP2. Collectively, PGRN acts as an indispensable component of GBA/LIMP2 lysosomal transport machinery via mediating the folding and trafficking of GBA/LIMP2 complex.

Although the mechanism by which OVA enhances the GD-like phenotype of PGRN KO macrophages is unclear, some known functions of PGRN may contribute to understand the unexpected observations in OVA-challenged PGRN KO mice. For instance, PGRN associates with TNF receptors and possesses the ability to suppress inflammation in various kinds of conditions[7,13,13-16], the lack of PGRN may thus lead to the abnormal response of macrophages to OVA-induced inflammation. In addition, inflammation is known to be involved in multiple sphingolipid LSDs and anti-inflammatory drugs have benefits in treading LSDs used alone or combined with other treatments[2]. Furthermore, PGRN was reported to associate with ER-stress related unfolded protein response[16], which was suggested to play a key role in cell death in GD[44]. The loss of PGRN leads to the abnormal ER stress responses and the aggregation of various proteins, such as TDP-43[9,45] and GBA/LIMP2 (this example), which in turn induce the increased ubiquitination for degrading aggregated proteins in the cytoplasm and nucleus, whereas in the lysosome PGRN deficiency causes the defect in the lysosomal delivery of GBA and in turn the accumulation of β-GlcCer. OVA stimulation may accelerates this process. Recently, it was reported that RIPK3, a component of the TNFR1 signaling complex that mediates necroptosis, was also involved in the pathology of GD and inhibiting RIPK3 might be a novel therapeutic approach for GD[46]. Thus, PGRN's anti-TNF and anti-cell death activities may also contribute to its therapeutic effects in GD and other LSDs.

Mutation of GRN gene are associated with front-temporal dementia[9,10]. Insufficiency of PGRN has been associated with neuron degenerative diseases[47]. Homozygous mutation of GRN was also linked to NCL[11,12]. The finding that PGRN is an indispensable component of HSP70 pathways mediating the lysosomal delivery of GBA/LIMP2 may be also associated with neurodegenerative diseases. Mutation of the GRN gene may directly affect the HSP70 trafficking pathway and in turn lead to defects in the clearance of proteins such as TDP-43, and α-synuclein[48], or indirectly affect the function of lysosomes resulting from the impairment of GBA delivery and consequent accumulation of glucosylceramide[49]. Thus, the identification of PGRN as a co-chaperone of HSP70 may also help us to better understand the putative molecular mechanisms underlying GRN mutations-associated disorders. In addition, PGRN physically binds to GBA whose mutations also associate with Parkinson's Disease (PD)[50], indicate that there may exist a functional and a genetically linkage between GRN and GBA genes, and their homozygous or heterozygous mutations may render some carriers vulnerable to rare (GD) and/or common (PD) diseases.

In summary, this study identifies PGRN as a previously-unrecognized molecule associated with and capable of causing GD, thus providing a solid foundation for future discoveries relating to this critical factor in GD and other lysosomal storage diseases. In addition, it also isolates PGRN as a novel co-chaperone of the prominent HSP70-mediated folding/trafficking pathway, thus uncovering a unique strategy to target this cardinal pathway of metabolic diseases. With the consideration that HSP70 folding and trafficking pathway is involved in a plethora of disease processes, the identification and manipulation of this new co-chaperone of the HSP70 pathway may lead to innovative therapeutics for treating LSDs, especially GD, and other metabolic pathologies and conditions.

Methods Summary

In Vivo Assays for Defining the Essential Role of PGRN in the Lysosomal Delivery of GBA Using Various Animal Models:

Comparison of OVA-challenged wild type and PGRN-deficient mice; Comparison of 1-year old wild type and PGRN-deficient mice; Administration of imiglucerase or recombinant human PGRN (rPGRN) into OVA-challenged PGRN-deficient mice that develop Gaucher-like diseases.

In Vitro Cell-Based Assays for Examining the β-GlcCer Clearance by Recombinant PGRN:

Comparison of lipid-challenged wild type and PGRN null bone marrow derived macrophages (BMDMs) in the presence or absence of rPGRN; Comparison of PGRN correction of altered lysosomes in fibroblasts of various LSDs with or without lipid stimulation.

Assays for Characterizing Gaucher-Like Diseases and for Visualizing Gaucher-Like Cells:

Histological analysis; Immunohistochemistry; Lipid composition analysis; GBA enzyme activity; Transmission Electron microscopy (TEM); Immunogold labeling TEM; Immunofluorescence staining and confocal microscope; Flow cytometry; Labeling of active lysosomal GBA in living cells using MDW933 inhibody green probe.

Mass Spectrometry and Protein/Protein Interaction Assays for Identifying and Characterizing the Associations Among PGRN, GBA, HSP70 and Sortilin:

Co-immunoprecipitation; Solid-phase binding; Analytical Surface Plasmon Resonance with SensiQ Pioneer, Sensitive and conventional Mass Spectrometry.

Materials and Methods

Materials:

Fibroblasts from type I, II and III GD, Tay-Sachs disease, Farber disease, type IV and IV mucolipidosis (ML), type III and VI mucopolysaccharidosis (MPS), Niemann-Pick disease type B, and Fabry disease were purchased from Coriell Cell Repositories (Camden, N.J.), and normal fibroblasts were purchased from Gibico. All fibroblasts were cultured in DMEM medium containing 10% FBS. Antibodies against GBA (sc-100544, sc-30844, and sc-32883), PGRN (SC-28928), Sortilin (sc-376576), α-GLA (sc-25823), HSP70 (sc-373867), Calregulin (sc-373863), TGN38 (sc-271624), EEA1 (sc-365652) LIMP2 (sc-55571), and LAMP2 (sc-18822), were purchased from Santa Cruz Biotechnology (Dallas, Tex.). β-GlcCer antibody (Cat. No. RAS_0010) was purchased from Glycobiotech GmbH (Germany). Donkey anti-Mouse IgG labeled with Alexa Fluor® 488, Alexa Fluor 647, or Cyanine cy3, and donkey anti-Rabbit labeled with Alexa Fluor® 488, or Cyanine cy3, and Donkey anti-sheep IgG labeled with Alexa Fluor 488, or Cyanine cy3 were purchased from Jackson ImmunoResearch Laboratories, Inc. (West Grove, Pa.). Recombinant His-tag PGRN protein was purified from 293T stable cell lines as described previously[13,14]. Recombinant GBA (Cat. No. 7410-GH-010), sortilin (Cat. No. 3154-ST-050), and LIMP2 (Cat. No. 1966-LM-050) proteins and sheep anti-mouse PGRN antibody (AF2557) were purchased from R&D Systems (Minneapolis, Minn.). Human PGRN ELISA kit was purchased from AdipoGen (San Diego, Calif.). ERK inhibitor PD98059, PI3K inhibitor Wortmannin and mTOR inhibitor rapamycin were purchased from Life Technologies. Imiglucerase was provided by Dr. Pastores.

Chronic Lung Inflammation Model:

C57B/L6 WT and PGRN KO mice were hosted in the animal facility of New York University as previously described[13,55]. 8 weeks-old mice were induced chronic lung inflammation by I.P. injection of OVA-Alum challenged at Day 1 and Day 15, followed by followed by intranasal challenge of 1% OVA beginning at Day 29 three times a week for four weeks[51]. In PGRN rescue experiments frequency of intranasal challenge of OVA was increased to three times a week. The mice were sacrificed, and spleen, liver, leg, lung and bronchoalveolar lavage (BAL) were collected. In the PGRN rescue experiments, 4 mg/kg of recombinant PGRN or 60 u/kg imiglucerase were I.P injected every week when intranasal challenge started.

In another experiment, WT and PGRN KO mice were hosted in animal facility of New York University until 1 year-old. Aged mice were sacrificed directly, and lung, spleen, liver, femur, and spine were collected for histology and micro-CT analysis.

Histology and Analysis:

After mice were sacrificed, one lobe of lung was cut without perfusion for future proteins and lipid analysis, the remaining part of lung was perfused with 4% paraformaldehyde (PFA). Spleen, liver, and femur were also collected and fixed with 4% PFA. All these tissues were embedded in paraffin, cut into slides, and stained with H&E and PAS by Mass Histology Service (Worcester, Mass.). Quantification of Gaucher-like cells number, and measurement of area of Gaucher-like cells were analyzed by Image J software.

The femurs from indicated groups of mice were cleaned off soft tissue. Following routine fixation, decalcification, and paraffin embedding, tissue sections were prepared and stained with hematoxylin and eosin. We measured the bone volume in a standard zone, situated at least 0.5 mm from the growth plate, excluding the primary spongiosa and trabeculae connected to the cortical bone, and enumerated the osteoclasts and trabecular area in the same zone as that used for assessing bone volume (10×original magnification), using BioQuant software.

Lipid Composition Analysis:

Lung from WT and PGRN KO mice with or without OVA challenge was collected, and homogenized with RIPA lysis buffer containing proteinase inhibitors cocktail. In addition, lung and spleen from PGRN KO mice at different ages, and fibroblasts from health control and GD patients were also processed using the same method. 1 mg total protein from each samples was used to measure the lipid composition by Lipidomics Core at Medical University of South Carolina. Levels of Ceramide, DAG, sphingomyelin, β-GlcCer, and glucosylsphingosine (GlcSph) were measured by the high-performance liquid chromatography/mass spectrometry (LC-MS/MS) methodology as previously described[21]. Plasma from healthy control and GD patients, as well as from WT and PGRN KO mice were collected, and the levels of β-GlcCer and GlcSph were measured. Analytical results of lipids were expressed as: lipid level/total cellular protein: pmol/mg protein, or pmol/ml plasma.

GBA Enzyme Activity:

Lung from WT and PGRN KO mice were lysed and 20 μg total protein were used to measure GBA activity as reported previously[52]. Briefly GBA activity was quantified by cleavage artificial substrate 4-methylumbelliferyl-β-D-glucopyranoside (4 MUGP) into 4-methylumbelliferone at pH5.9 solutions (50 mM citrate phosphate buffer containing 0.15% Triton X-100 and 0.125% sodium taurocholate). The amount of 4-methylumbelliferone was measured at 360 nm excitation and 460 nm emission filters. GBA activity was expressed as nM/mg total protein/h.

Transmission Electron Microscope (TEM):

WT and PGRN KO mice after OVA treatment, as well as aged PGRN KO mouse, were anesthetized and the lung was perfuse fixed with fixative containing 2.5% Glutaraldehyde and 2% paraformaldehyde in 0.1M sodium cacodylate buffer (pH 7.2) for 2 hours. After washing, the samples were fixed in 1% OsO4 for 1 hour, block staining with 1% uranyl acetate for 1 hour, dehydration and embedded in Embed 812 (Electron Microscopy Sciences, Hatfield, Pa.). 60 nm sections were cut, and stained with uranyl acetate and lead citrate by standard methods. Stained grids were examined under Philips CM-12 electron microscope (FEI; Eindhoven, The Netherlands) and photographed with a Gatan (4 k×2.7 k) digital camera (Gatan, Inc., Pleasanton, Calif.).

For immunoelectron microscopy, mice were perfused and fixed with 4% PFA in 0.1M phosphate buffer (pH7.4), and the lung was dissected and continuously fixed in the freshly made 3% PFA in 0.1M phosphate buffer containing 0.1% glutaraldehyde and 4% sucrose (pH 7.4). After washing and dehydration, the tissue were embedded in Lowicryl K4M (Polysciences, Inc., Warrington, Pa.) and LR White (Electron Microscopy Sciences, Hatfield, Pa.). Polymerized will be under UV light (360 nm) at −35° C. for LK4M and −10° C. for LR White. Ultrathin sections were cut, mounted on Formvar-Carbon coated nickel grids. After incubation with primary antibodies at 4° C. overnight, gold conjugated secondary antibodies (15 nm Protein A Gold, Cell Microscopy Center, University Medical Center Utrecht, 35584 CX Utrecht, The Netherlands; 18 nm Colloidal Gold-AffiniPure Goat Anti-Rabbit IgG (H+L), Jackson ImmunoReasearch Laboratories, Inc., West Grove, Pa.) were applied. The grids were stained with uranyl acetate and lead citrate by standard methods, and examined under Philips CM-12 electron microscope (FEI; Eindhoven, The Netherlands) and photographed with a Gatan (4 k×2.7 k) digital camera (Gatan, Inc., Pleasanton, Calif.).

Immunofluorescence Staining and Confocal Microscope:

Frozen lung sections, or cover-slip cultured BMDM, were fixed with 4% formaldehydrate for 5 min and washed twice with PBS. The cells were permeabilized by 0.1% Triton-100 PBS for 5 min and then wash with PBS. The tissues were blocked with 1:50 dilution of normal donkey serum for 30 min. Primary antibodies were probed on the slides at 4° C. degree overnight. The next day slides were washed with PBS, fluorescence-labeled secondary antibodies (Alexa Fluor® 488-labeled donkey anti-mouse combined with Cyanine cy3-labeled donkey anti-rabbit antibody, or in some experiments different fluorescence were used) were added for 1 hour and wash with PBS. The tissues or BMDM cells were mounted on anti-fade medium containing DAPI. The images were taken by Leica TCS SP5 con-focal system.

Flow Cytometry:

BAL was collected when mice were sacrificed, and centrifuged at 1200 rpm for 5 min to collect cells. The cells were suspended and washed in ice-cold PBS containing 0.1% FBS for two times. The cells were stained with FITC-labeled CD11b antibody (eBioscience San Diego, Calif.) for 1 hour and analyzed by BD FACScan, and data were analyzed by FlowJo software.

Measurement of Bone Mineral Density (BMD):

We assessed the BMD (gm/cm2) of the whole skeletons of aged WT and PGRN-deficient mice, using a PIXImus bone densitometer (Lunar, Madison, Wis.). The instrument was calibrated before each scanning session, using a phantom with known BMD, according to the manufacturer's guidelines. Mice were anesthetized by intraperitoneal injection of ketamine (90 μg/g of body weight) and xylazine (10 μg/g of body weight) and then were placed in the prone position on the specimen tray to allow scanning of the entire skeleton.

Micro-CT:

The trabecular volume in the distal femoral metaphysis was measured using a Scanco μCT40 scanner (Scanco Medical AG, Basserdorf, Switzerland). A threshold of 300 was used for evaluation of all scans. 30 slices were analyzed, starting with the first slice in which condyles and primary spongiosa were no longer visible.

Immunoprecipitation:

Lung tissue from OVA-challenged or -unchallenged WT and PGRN KO mice with or without with or without rPGRN treatment were lysed by RIPA lysis buffer containing protease inhibitors. 12000 rpm centrifuge 10 min to pellet the debris. The supernatant were transferred to a new tube and 10 seconds supersonic pulse were used to further release membrane proteins. Same amount of proteins from each group of mouse were mixed together to represent the protein profile of each group. 400 μg protein from mixed samples were used for immunoprecipitation. 2 μg/ml normal mouse and rabbit antibodies and 20 μl protein A/G agarose-beads were added, and incubated 1 hour at 4° C. Centrifuge at 3000 rpm for 5 min to pellet the beads. The supernatant were transferred to a new tube and 2 μg/ml primary antibodies were added and incubated 1 hour at 4° C., then 20 μl protein A/G agarose-beads were added and incubated overnight. The beads were washed with RIPA lysis buffer 6-8 times, the samples were run on SDS-PAGE, and targeted proteins were probed with antibody and visualized by western-blot. In some experiments, the samples after immunoprecipitation were sent to NYU core facility to do Mass Spectrometry.

Immunohistochemistry:

Paraffin-embedded lung slides from WT and PGRN KO mice de-paraffined by xylene and gradient ethanol. Antigen was retrieved by using 0.1% trypsin (diluted from 0.5% trypsin by 0.1% $CaCl_2$) at 37° C. for 30 min. Endogenous hydrogen peroxidase was inactivated by 3% $H_2O_2$ in PBS for 10 minutes. The slides were blocked with 3% BSA and 20% goat serum for 30 minutes. Primary antibodies were diluted at 1:20-50 with 2% goat serum, primed on the slides at 4° C. overnight. The next day slides were washed with PBS and secondary antibody were added (1:200 biotin-labeled goat-anti rabbit antibody or goat-anti mouse antibody) for 1 hour. The staining was visualized by Vector ABC peroxidase kit, followed by DAB substrates.

Mass Spectrum:

1) Gel Separation and Digestion. Samples were reduced with DTT at 57° C. for 1 hour and were alkylated with Iodoacetamide at RT in the dark for 45 minutes. Each sample was loaded onto a NuPAGE® 4-12% Bis-Tris Gel 1.0 mm The gel was stained using GelCode Blue Stain Reagent (Thermo Scientific) and Coomassie stained gel bands were excised as indicated on the gel image. Excised gel pieces were destained with a 50:50 v/v solution of methanol and 100 mM ammonium bicarbonate. The gel pieces were partially dehydrated with an acetonitrile rinse and further dried in a SpeedVac concentrator for 20 minutes. 300 ng of sequencing grade modified trypsin (Promega) were added to each gel sample. After the trypsin was absorbed 100 µl of 100 mM ammonium bicarbonate was added to cover the gel pieces. Digestion proceeded overnight on a shaker at RT.

(2) Protein Extraction. A slurry of R2 20 µm Poros beads (Life Technologies Corporation) in 5% formic acid and 0.2% trifluoroacetic acid (TFA) was added to each sample at an volume equal to that of the ammonium bicarbonate added for digestion. The samples shook at 4° C. for 2 hours. The beads were loaded onto equilibrated C18 ziptips (Millipore) using a microcentrifuge for 30 seconds at 6000 rpm. Gel pieces were rinsed three times with 0.1% TFA and each rinse was added to its corresponding ziptip followed by microcentrifugation. The extracted porors beads were further washed with 0.5% acetic acid Peptides were eluted by the addition of 40% acetonitrile in 0.5% acetic acid followed by the addition of 80% acetonitrile in 0.5% acetic acid. The organic solvent was removed using a Speed Vac concentrator and the sample reconstituted in 0.5% acetic acid.

MS Analysis.

⅕th of each sample was analyzed individually with the mIgG analyzed first, then the KO GBA, and finally the WT GBA. Samples were injected for on-line LC-MS using the autosampler of a EASY-nLC 1000 (Thermo Scientific). Peptides were gradient eluted from the column directly to Q Exactive mass spectrometer (Thermo Scientific) using a 1 hour gradient Solvent A: 5% acetonitrile, 0.5% acetic acid Solvent B: 95% acetonitrile, 0.5% acetic acid.

MS Method.

High resolution full MS spectra were acquired with a resolution of 70,000, an AGC target of 1e6, with a maximum ion time of 120 ms, and scan range of 300 to 1500 m/z. Following each full MS twenty data-dependent high resolution HCD MS/MS spectra were acquired. All MS/MS spectra were collected using the following instrument parameters: resolution of 17,000, AGC target of 2e5, maximum ion time of 250 ms, one microscan, 2 m/z isolation window, fixed first mass of 150 m/z, and NCE of 27. MS/MS spectra were searched against a uniprot mouse database using Sequest within Proteome Discoverer.

Surface Plasmon Resonance (SPR):

All SPR experiments were done by SensiQ Technologies Inc. (Oklahoma City, Okla.) by using SensiQ Pioneer at a controlled analysis temperature of 25° C., and samples in the instrument sample racks were maintained at 18° C. The running buffer throughout the immobilization and the assay consisted of 10 mM HEPES, 150 mM NaCl, 0.005% Tween 20. Buffer pH was adjusted to pH 7.4, 6.5, 6.0 or 5.5 for individual runs, and for each pH the running buffer was used to prepare PGRN samples and sucrose diffusion standards.

A COOH1 chip was installed and conditioned via 10 second injections (2× each) of 10 mM HCl, 50 mM NaOH, and 0.1% SDS. Channel 3 was activated via a five minute injection of 4 mM EDC and 1 mM NHS in water at a 20 uL/min flow rate. GBA (25 ug/mL in 10 mM sodium acetate pH 5.5) was then injected for ~two minutes at a 10 uL/min flow rate. Channels 1 and 2 were then activated with 4 mM EDC and 1 mM NHS in water for five minutes. Sortilin (10 ug/mL in sodium acetate pH 4.0) was immobilized on channel 1 via a five minute injection at a 10 uL/min flow rate. BSA (10 ug/mL in sodium acetate pH 4.3) was immobilized on the reference channel to reduce non-specific binding. All channels were capped with a four minute injection of 1M Ethanolamine pH8.0.

The assay of PGRN was performed with a total of five buffer blank injections and two replicates of 200 nM PGRN, all of which were given a 1 hour dissociation time. The OneStep™ injection was used for this assay to determine kinetic rate constants and the equilibrium dissociation constant from a single gradient inject. Two injections of 3% sucrose in running buffer were performed to serve as a diffusion standard.

Data was analyzed using the QDat Analysis Software (SensiQ Technologies and BioLogic Software). All data were double referenced to a reference channel (channel 2) and buffer blanks. The average signal of the buffer blanks was used to subtract injection artifacts. Referenced SPR data from the analysis channels were model fit to ascertain ka, kd, and $K_D$ for the interactions.

Solid Phase Binding:

0.1, 1, 2, and 5 µg/ml PGRN proteins were coated in 96-wells with triplicate wells in PBS for overnight. The plate was washed with 0.1% tween/PBS five times and then blocked with 2% BSA/PBS solution. Two µg BSA, LIMP2 and GBA protein were labeled with biotin followed the protocol of EZ-Link Sulfo-NHS-LC-Biotin and Biotinylation Kits (Thermo Scientific). Biotin-labeled LIMP2, GBA or BSA were added in the plate and incubate for 2 hours. Wash with 0.1% tween/PBS, and coated with streptavidin-HRP (1:2000 dilution) solution for 1 hour. After washing add the substrate and stop the reaction with 100 µl 2M $H_2SO_4$. Read result at UV 450 nm in plate reader.

BMDM Differentiation and In Vitro GD Model:

Differentiation of BMDMs was performed by following protocol reported previously[25,53]. Briefly monocytes were isolated from WT and KO bone marrow and cultured in RPMI1640, supplemented with L929 condition medium for 5 days to differentiation into macrophages. To mimic development of Gaucher cells in vitro, 50 µg/ml brain lysates (1 g of mouse brain tissues were homogenized in 10 ml of DMEM medium by Bio-Gen PRO200 Homogenizer from 1 min at highest speed) containing various kinds of lipids, including sphingolipid, were added in the cell culture supernatant for 10 days. In the case of the in vitro rescue experiments, 0.1 and 0.4 µg/ml PGRN were added at the same time with lipid. Cell culture mediums were replenished every three days. The levels of β-GlcCer were stained by immunofluorescence staining.

Fluorescence Labeling of Active Form of Lysosomal GBA:

MDW933, a specific sensitive fluorescence dye for labeling active lysosomal GBA[28,30], was generously provided by Dr. Hermen E. Overkleeft at University of Leiden. BMDMs were cultured on cover glass, and MDW933 (50 nM) were added in culture medium for 2 hours to label lysosomal GBA. Cells were then fixed with 3% (v/v) paraformaldehyde in PBS for 15 min, and permeabilized by 0.1 mM $NH_4Cl$ in PBS for 10 min. BMDMs were mounted with DAPI-medium, and fluorescence were visualized under confocal microscope.

Knockdown of PGRN and HSP70 by siRNA Approach:

siRNAs against mouse PGRN and HSP70 were purchased from Life Technology. RAW264.7 cells were transfected with 20 pmol of corresponding siRNA using Lipofectamine 2000. The cells were then treated with lipid mixture (50 µg/ml) for 24 hours and the level of active form of GBA were measured by MDW933 dye, and the knockdown efficiency of PGRN or HSP70 was examined by immunofluorescence staining using their specific antibodies.

Lysosome Staining in LSD Fibroblasts:

Fibroblasts from different LSDs and healthy control were cultured on coverslip in 24-well plates in the absence or presence of recombinant PGRN protein (0.4 µg/ml), lipid lysis (50 µg/ml), and PGRN plus lipid lysis for 24 hours. The next day fresh medium containing 100 nM LysoTracker® Red was added for 1 hour. The cells were washed with PBS and fixed in 2% PFA. The coverslips were mounted on slides and the staining of lysosomes was imaged by confocal microscopy. Ten images were randomly taken from each sample, and fluorescence intensities were measured by Image J software.

Human Study Participants:

115 GD samples were collected from New York University School of Medicine by Dr. Pastores. 44 healthy controls from the general population and 55 healthy controls of Ashkenazi Jewish were provided by Dr. Saunders-Pullman from Beth Israel Medical Center. Each of the patients signed a consent form. This study was approved by Institutional Review Boards of New York University School of Medicine and Beth Israel Medical Center.

Serum Levels of PGRN in GD Patients:

Serum levels of PGRN were measured by ELISA kit from Adipogen (San Diego, Calif.). Briefly, the ELISA plated were blocked with 300 µl blocking buffer for 30 min. Serum was diluted 200 fold by PBS. After blocking, load 100 µl samples and standards for 2 hours. Wash the plates with PBS/tween for 5 times and add 100 µl Detection Antibody for 1 hour. Wash the plates again and add 100 µl Detector for another hour. Rinse the plates and add 100 µl TMB Substrate Solution, and the reaction was terminated by Stop solution. The results were recorded at 450 nm by plate reader. The concentrations of PGRN were calculated based on the standard curve.

Sequencing GRN Gene:

Genomic DNAs from 40 GD patients were used as templates to amplify full-length GRN gene, including 1 kb promoter region and 8 kb full-length GRN gene, by Phusion® High-Fidelity DNA Polymerases (NEB Inc, Ipswich, Mass.). All PCR products were mixed at equal molar ratio into one tube. The final sample was sent to Genomic facility of Yale University for gene sequencing by a novel technology, PacBio RS II Sequencing System[54]. The sequence of each patient was sorted out by their barcode sequence, and full-length GRN sequence was aligned using basic local alignment with successive refinement (blasr) from Pacific BioSciences (github, Pacific Biosciences; Chaisson, M J and Tesler, G (2012) BMC Bioinformatics 13:238), and then SAMtools (samtools sourceforge) were used to detect the variants in the patients samples.

Statistical Analysis:

For comparison of treatment groups, we performed unpaired t-tests, and one-way or two-way ANOVA (where appropriate). All statistical analysis was performed using SPSS Software. Statistical significance was two-sided and was achieved when at $p<0.05$.

REFERENCES

1 Brady, R. O., Kanfer, J. N. & Shapiro, D. Metabolism of Glucocerebrosides. Ii. Evidence of an Enzymatic Deficiency in Gaucher's Disease. *Biochemical and biophysical research communications* 18, 221-225 (1965).

2 Platt, F. M. Sphingolipid lysosomal storage disorders. *Nature* 510, 68-75, doi:10.1038/nature13476 (2014).

3 Beutler, E. Gaucher's disease. *The New England journal of medicine* 325, 1354-1360, doi:10.1056/NEJM199111073251906 (1991).

4 Hrabal, R., Chen, Z., James, S., Bennett, H. P. & Ni, F. The hairpin stack fold, a novel protein architecture for a new family of protein growth factors. *Nat Struct Biol* 3, 747-752 (1996).

5 Bateman, A. & Bennett, H. P. The granulin gene family: from cancer to dementia. *BioEssays: news and reviews in molecular, cellular and developmental biology* 31, 1245-1254, doi:10.1002/bies.200900086 (2009).

6 He, Z., Ong, C. H., Halper, J. & Bateman, A. Progranulin is a mediator of the wound response. *Nat Med* 9, 225-229, doi:10.1038/nm816 (2003).

7 Zhu, J. et al. Conversion of proepithelin to epithelins: roles of SLPI and elastase in host defense and wound repair. *Cell* 111, 867-878 (2002).

8 Jian, J., Konopka, J. & Liu, C. Insights into the role of progranulin in immunity, infection, and inflammation. *Journal of leukocyte biology* 93, 199-208, doi:10.1189/jlb.0812429 (2013).

9 Baker, M. et al. Mutations in progranulin cause tau-negative frontotemporal dementia linked to chromosome 17. *Nature* 442, 916-919, doi:10.1038/nature05016 (2006).

10 Cruts, M. et al. Null mutations in progranulin cause ubiquitin-positive frontotemporal dementia linked to chromosome 17q21. *Nature* 442, 920-924, doi:10.1038/nature05017 (2006).

11 Ahmed, Z. et al. Accelerated lipofuscinosis and ubiquitination in granulin knockout mice suggest a role for progranulin in successful aging. *The American journal of pathology* 177, 311-324, doi:10.2353/ajpath.2010.090915 (2010).

12 Gotzl, J. K. et al. Common pathobiochemical hallmarks of progranulin-associated frontotemporal lobar degeneration and neuronal ceroid lipofuscinosis. *Acta Neuropathol*, doi:10.1007/s00401-014-1262-6 (2014).

13 Tang, W. et al. The growth factor progranulin binds to TNF receptors and is therapeutic against inflammatory arthritis in mice. *Science* 332, 478-484, doi:10.1126/science.1199214 (2011).

14 Jian, J. et al. Progranulin directly binds to the CRD2 and CRD3 of TNFR extracellular domains. *FEBS letters*, doi:10.1016/j.febslet.2013.0.09.024 (2013).

15 Liu, C., Li, X. X., Gao, W., Liu, W. & Liu, D. S. Progranulin-Derived Atsttrin Directly Binds to TNFRSF25 (DR3) and Inhibits TNF-Like Ligand 1A (TL1A) Activity. *PloS one* 9, e92743, doi:10.1371/journal.pone.0092743 (2014).

16 Li, M. et al. Progranulin is required for proper ER stress response and inhibits ER stress-mediated apoptosis through TNFR2. *Cell Signal* 26, 1539-1548, doi:10.1016/j.cellsig.2014.03.026 (2014).

17 Thurner, L. et al. Progranulin antibodies entertain a proinflammatory environment in a subgroup of patients with psoriatic arthritis. *Arthritis research & therapy* 15, R211, doi:10.1186/ar4406 (2013).

18 Thurner, L. et al. Proinflammatory Progranulin Antibodies in Inflammatory Bowel Diseases. *Digestive diseases and sciences*, doi:10.1007/s10620-014-3089-3 (2014).

19 Rothman, J. E. & Schekman, R. Molecular mechanism of protein folding in the cell. *Cell* 146, 851-854, doi:10.1016/j.cell.2011.08.041 (2011).

20 Grabowski, G. A. Gaucher disease and other storage disorders. *Hematology/the Education Program of the American Society of Hematology. American Society of Hematology. Education Program* 2012, 13-18, doi:10.1182/asheducation-2012.1.13 (2012).

21 Mazzulli, J. R. et al. Gaucher disease glucocerebrosidase and alpha-synuclein form a bidirectional pathogenic loop in synucleinopathies. *Cell* 146, 37-52, doi:10.1016/j.cell.2011.06.001 (2011).

22 Aerts, J. M. et al. Glucocerebrosidase, a lysosomal enzyme that does not undergo oligosaccharide phosphorylation. *Biochimica et biophysica acta* 964, 303-308 (1988).

23 Van Weely, S. et al. Function of oligosaccharide modification in glucocerebrosidase, a membrane-associated lysosomal hydrolase. *European journal of biochemistry/FEBS* 191, 669-677 (1990).

24 Xu, Y. H., Sun, Y., Barnes, S. & Grabowski, G. A. Comparative therapeutic effects of velaglucerase alfa and imiglucerase in a Gaucher disease mouse model. *PloS one* 5, e10750, doi:10.1371/journal.pone.0010750 (2010).

25 Hu, X. et al. IFN-gamma suppresses IL-10 production and synergizes with TLR2 by regulating GSK3 and CREB/AP-1 proteins. *Immunity* 24, 563-574, doi:10.1016/j.immuni.2006.02.014 (2006).

26 Hu, F. et al. Sortilin-mediated endocytosis determines levels of the frontotemporal dementia protein, progranulin. *Neuron* 68, 654-667, doi:10.1016/j.neuron.2010.09.034 (2010).

27 Prabakaran, T. et al. Mannose 6-phosphate receptor and sortilin mediated endocytosis of alpha-galactosidase A in kidney endothelial cells. *PloS one* 7, e39975, doi:10.1371/journal.pone.0039975 (2012).

28 Witte, M. D. et al. Ultrasensitive in situ visualization of active glucocerebrosidase molecules. *Nature chemical biology* 6, 907-913, doi:10.1038/nchembio.466 (2010).

29 Aerts, J. M. et al. Biomarkers in the diagnosis of lysosomal storage disorders: proteins, lipids, and inhibodies. *Journal of inherited metabolic disease* 34, 605-619, doi:10.1007/s10545-011-9308-6 (2011).

30 Gaspar, P. et al. Action myoclonus-renal failure syndrome: diagnostic applications of activity-based probes and lipid analysis. *Journal of lipid research* 55, 138-145, doi:10.1194/jlr.M043802 (2014).

31 Reczek, D. et al. LIMP-2 is a receptor for lysosomal mannose-6-phosphate-independent targeting of beta-glucocerebrosidase. *Cell* 131, 770-783, doi:10.1016/j.cell.2007.10.018 (2007).

32 Neculai, D. et al. Structure of LIMP-2 provides functional insights with implications for SR-BI and CD36. *Nature* 504, 172-176, doi:10.1038/nature12684 (2013).

33 Gonzalez, E. M., Mongiat, M., Slater, S. J., Baffa, R. & Iozzo, R. V. A novel interaction between perlecan protein core and progranulin: potential effects on tumor growth. *J Biol Chem* 278, 38113-38116 (2003).

34 Saftig, P. & Klumperman, J. Lysosome biogenesis and lysosomal membrane proteins: trafficking meets function. *Nature reviews. Molecular cell biology* 10, 623-635, doi:10.1038/nrm2745 (2009).

35 Blanz, J. et al. Disease-causing mutations within the lysosomal integral membrane protein type 2 (LIMP-2) reveal the nature of binding to its ligand beta-glucocerebrosidase. *Human molecular genetics* 19, 563-572, doi:10.1093/hmg/ddp523 (2010).

36 Yang, C. et al. Celastrol increases glucocerebrosidase activity in Gaucher disease by modulating molecular chaperones. *Proceedings of the National Academy of Sciences of the United States of America* 111, 249-254, doi:10.1073/pnas.1321341111 (2014).

37 Kirkegaard, T. et al. Hsp70 stabilizes lysosomes and reverts Niemann-Pick disease-associated lysosomal pathology. *Nature* 463, 549-553, doi:10.1038/nature08710 (2010).

38 Tanaka, Y., Matsuwaki, T., Yamanouchi, K. & Nishihara, M. Increased lysosomal biogenesis in activated microglia and exacerbated neuronal damage after traumatic brain injury in progranulin-deficient mice. *Neuroscience* 250, 8-19, doi:10.1016/j.neuroscience.2013.06.049 (2013).

39 Farfel-Becker, T., Vitner, E. B. & Futerman, A. H. Animal models for Gaucher disease research. *Disease models & mechanisms* 4, 746-752, doi:10.1242/dmm.008185 (2011).

40 Lu, J. et al. Histone deacetylase inhibitors prevent the degradation and restore the activity of glucocerebrosidase in Gaucher disease. *Proceedings of the National Academy of Sciences of the United States of America* 108, 21200-21205, doi:10.1073/pnas.1119181109 (2011).

41 Ingemann, L. & Kirkegaard, T. Lysosomal Storage Diseases and the Heat Shock Response: Convergences and Therapeutic Opportunities. *Journal of lipid research*, doi:10.1194/jlr.R048090 (2014).

42 Almeida, S., Zhou, L. & Gao, F. B. Progranulin, a glycoprotein deficient in frontotemporal dementia, is a novel substrate of several protein disulfide isomerase family proteins. *PloS one* 6, e26454, doi:10.1371/journal.pone.0026454 (2011).

43 Mu, T. W. et al. Chemical and biological approaches synergize to ameliorate protein-folding diseases. *Cell* 134, 769-781, doi:10.1016/j.cell.2008.06.037 (2008).

44 Wei, H. et al. ER and oxidative stresses are common mediators of apoptosis in both neurodegenerative and non-neurodegenerative lysosomal storage disorders and are alleviated by chemical chaperones. *Human molecular genetics* 17, 469-477, doi:10.1093/hmg/ddm324 (2008).

45 Tanaka, Y., Chambers, J. K., Matsuwaki, T., Yamanouchi, K. & Nishihara, M. Possible involvement of lysosomal dysfunction in pathological changes of the brain in aged progranulin-deficient mice. *Acta neuropathologica communications* 2, 78, doi:10.1186/PREACCEPT-4589926441299369 (2014).

46 Vitner, E. B. et al. RIPK3 as a potential therapeutic target for Gaucher's disease. *Nat Med* 20, 204-208, doi:10.1038/nm.3449 (2014).

47 Petkau, T. L. & Leavitt, B. R. Progranulin in neurodegenerative disease. *Trends in neurosciences*, doi:10.1016/j.tins.2014.04.003 (2014).

48 Leverenz, J. B. et al. A novel progranulin mutation associated with variable clinical presentation and tau, TDP43 and alpha-synuclein pathology. *Brain: a journal of neurology* 130, 1360-1374, doi:10.1093/brain/awm069 (2007).

49 Platt, F. M., Boland, B. & van der Spoel, A. C. The cell biology of disease: lysosomal storage disorders: the cellular impact of lysosomal dysfunction. *The Journal of cell biology* 199, 723-734, doi:10.1083/jcb.201208152 (2012).

50 Eblan, M. J., Walker, J. M. & Sidransky, E. The glucocerebrosidase gene and Parkinson's disease in Ashkenazi Jews. *The New England journal of medicine* 352, 728-731; author reply 728-731, doi:10.1056/NEJM200502173520719 (2005).

51 Daley, E. et al. Pulmonary arterial remodeling induced by a Th2 immune response. *J Exp Med* 205, 361-372, doi: 10.1084/jem.20071008 (2008).

52 Fabrega, S. et al. Human glucocerebrosidase: heterologous expression of active site mutants in murine null cells. *Glycobiology* 10, 1217-1224 (2000).

53 Weischenfeldt, J. & Porse, B. Bone Marrow-Derived Macrophages (BMM): Isolation and Applications. *CSH protocols* 2008, pdb prot5080, doi:10.1101/pdb.prot5080 (2008).

54 Eid, J. et al. Real-time DNA sequencing from single polymerase molecules. *Science* 323, 133-138, doi: 10.1126/science.1162986 (2009).

55 Yin, F. et al. Exaggerated inflammation, impaired host defense, and neuropathology in progranulin-deficient mice. *J Exp Med* 207(1):117-128 (2010).

Example 2

PGRN Derivative Peptide Atsttrin

PGRN peptides, particularly including the PGRN derivative peptide denoted Atsttrin, have been evaluated and identified as having overlapping PGRN activity and, in some instances enhanced activity versus wild-type or full length PGRN. The PGRN derivative peptide Atsttrin is active as a modulator of TNF/TNFR activity and signaling, inhibiting or blocking TNF-mediated signaling or response, including TNF-α-induced inflammatory arthritis (Tang W et al (2011) Science 332:478-484; WO 2010120374). Atsttrin is a PGRN-derived engineered protein (Antagonist of TNF/TNFR Signaling via Targeting TNF Receptors), comprising combinations of half units of PGRN units A, C and F in combination with linker units P3, P4 and P5 (U.S. Pat. No. 8,362,218; WO 2010120374). Atsttrin provides a PGRN-derived active peptide having overlapping activity and capability with the full length PGRN molecule.

Figure 39:
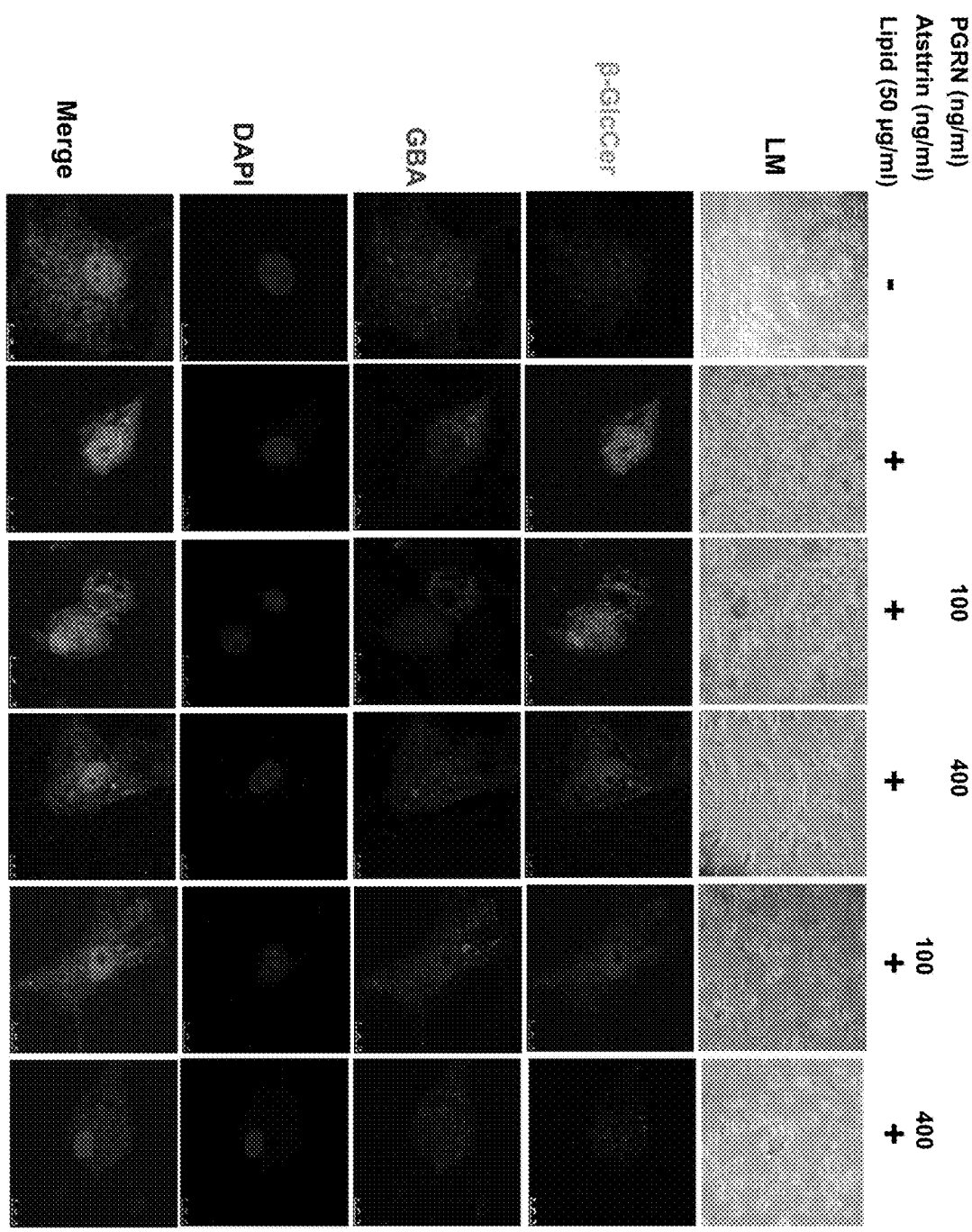
FIG. 39 depicts that PGRN and Atsttrin, the PGRN-derived engineered protein, rescue β-GlcCer accumulation in PGRN KO macrophages. BMDM from PGRN KO mice were administered 50 µg/ml lipid for 10 days, with or without various amounts of PGRN or Atsttrin, as indicated (100 ng/ml and 400 ng/ml PGRN or Atsttrin). Under light microscopy (LM), BMDM become mess-like after lipid treatment, and this morphological change was partially rescued by both PGRN and Atsttrin in dose-dependent manner (upper panel). β-GlcCer is accumulated with lipid treatment, and the accumulation is blocked by addition of recombinant PGRN or Atsttrin in a dose-dependent manner.

PGRN deriative peptide Atsttrin was evaluated for activity and effects like PGRN in LSDs, including in the PGRN KO induced Gaucher's disease. Both PGRN and Atsttrin, the PGRN-derived engineered protein, were found to rescue β-GlcCer accumulation in PGRN KO macrophages. BMDM from PGRN KO mice were treated with 50 μg/ml lipid for 10 days, with or without various amounts of PGRN or Atsttrin (100 ng/ml or 400 ng/ml) and assessed (FIG. 39). Under a light microscope, BMDM looks messy and the cells become disorganized after lipid treatment, and these morphological changes was partially rescued by either of PGRN and Atsttrin in a dose-dependent manner (upper panel) (FIG. 39 first set of panels (LM)). β-GlcCer is accumulated with lipid treatment, and the accumulation is prevented by addition of either recombinant PGRN and Atsttrin in a dose-dependent manner (FIG. 39).

Figure 40:
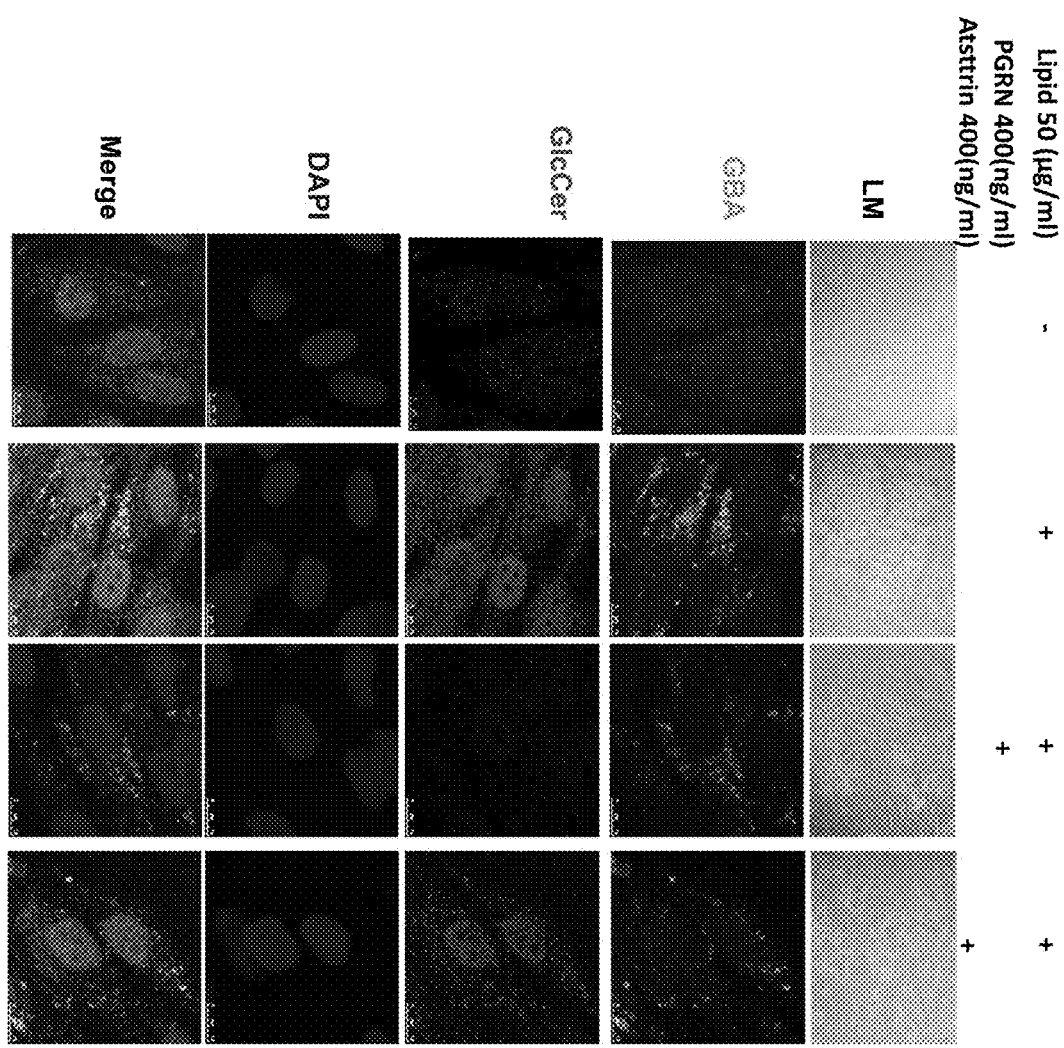
FIG. 40 shows that PGRN and Atsttrin rescue β-GlcCer accumulation in fibroblasts from GD patients. Fibroblasts were isolated from Type II GD patients and treated with 50 µg/ml lipid mixture for 2 days. Expression of GBA and β-GlcCer were measured by immunofluorescence staining, and images were acquired by co-focal microscope. The lipid treatment significantly induced GBA aggregation and β-GlcCer accumulation in GD fibroblasts. 400 ng/ml PGRN treatment almost completely prevents the GBA aggregation and β-GlcCer storage. Atsttrin show some effect but less than PGRN.

PGRN and Atsttrin were found to rescue β-GlcCer accumulation in fibroblasts from GD patients. Fibroblasts were isolated from Type II GD patients and evaluated with no treatment, lipid mixture alone, or the lipid mixture combined with treatment with either PGRN (400 ng/ml) or Atsttrin (400 ng/ml). The fibroblasts were treated with 50 μg/ml lipid mixture, with or without added PGRN or Atsttrin for 2 days. The expression of GBA and β-GlcCer were then measured by immunofluorescence staining, and images were acquired by confocal microscopy. The results (FIG. 40) show that lipid treatment significantly induced GBA aggregation and β-GlcCer accumulation in GD fibroblasts, and that 400 ng/ml PGRN treatment almost completely prevented the GBA aggregation and β-GlcCer storage. Unlike in BMDM from PGRN KO mice, Atsttrin exhibited less efficiency versus PGRN in rescuing the accumulation phenotype.

We found that both PGRN and Atsttrin works well in BMDM from PGRN KO mice, however, Atstrrin shows a somewhat lower efficacy at the same dose in GD fibroblast cells. It suggests that PGRN can get into fibroblasts successfully, while Atsttrin enters fibroblasts with less efficiency. The endocytosis of PGRN is mediated by Sortilin, and PGRN binds Sortilin with its last three C-terminal amino acids, while Atsttrin does not have this motif. We hypothesize that Atsttrin may not enter fibroblasts via a Sortilin-dependent entodytosis pathway. It is notable that increased concentrations of Attstrin (see below) are effective to rescue β-GlcCer accumulation in GD fibroblasts. In contrast, both PGRN and Atsttrin can be taken up by macrophages, so both proteins are equally effective in macrophages.

Figure 41:
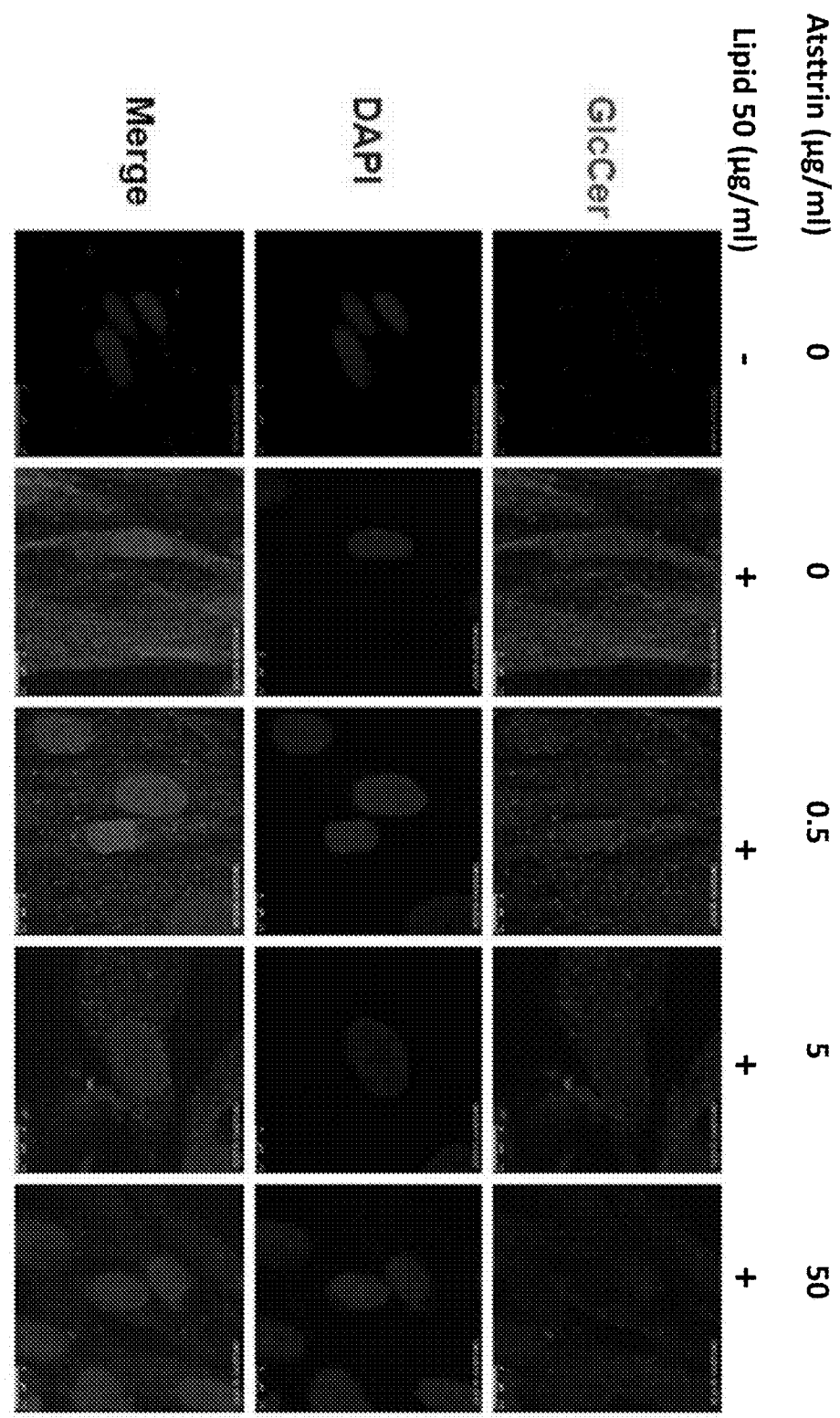
FIG. 41 shows that Atsttrin rescues β-GlcCer accumulation in a dosage-dependent manner in fibroblasts from GD patients treated with lipid. Fibroblasts from GD patients were treated with 50 µg/ml lipid mixture, together with various amounts of Atsttrin, as indicated (0, 0.5, 5 and 50 µg/ml Atsttrin). Immunofluorescence staining for β-GlcCer is shown. Atsttrin rescues β-GlcCer accumulation in a dose-dependent manner, particularly effective at 50 µg/ml.

Further studies showed that Atsttrin rescues β-GlcCer accumulation in a dosage-dependent manner, particularly at higher doses. Fibroblasts from GD patients were treated with 50 μg/ml lipid mixture (as described above), together with various amounts of Atsttrin (0.5 μg/ml, 5 μg/ml, and 50 μg/ml). β-GlcCer level was evaluated and viewed by immunofluorescence staining (FIG. 41). Atsttrin rescues β-GlcCer accumulation in a dose-dependent manner, and especially at 50 μg/ml.

Figure 42:
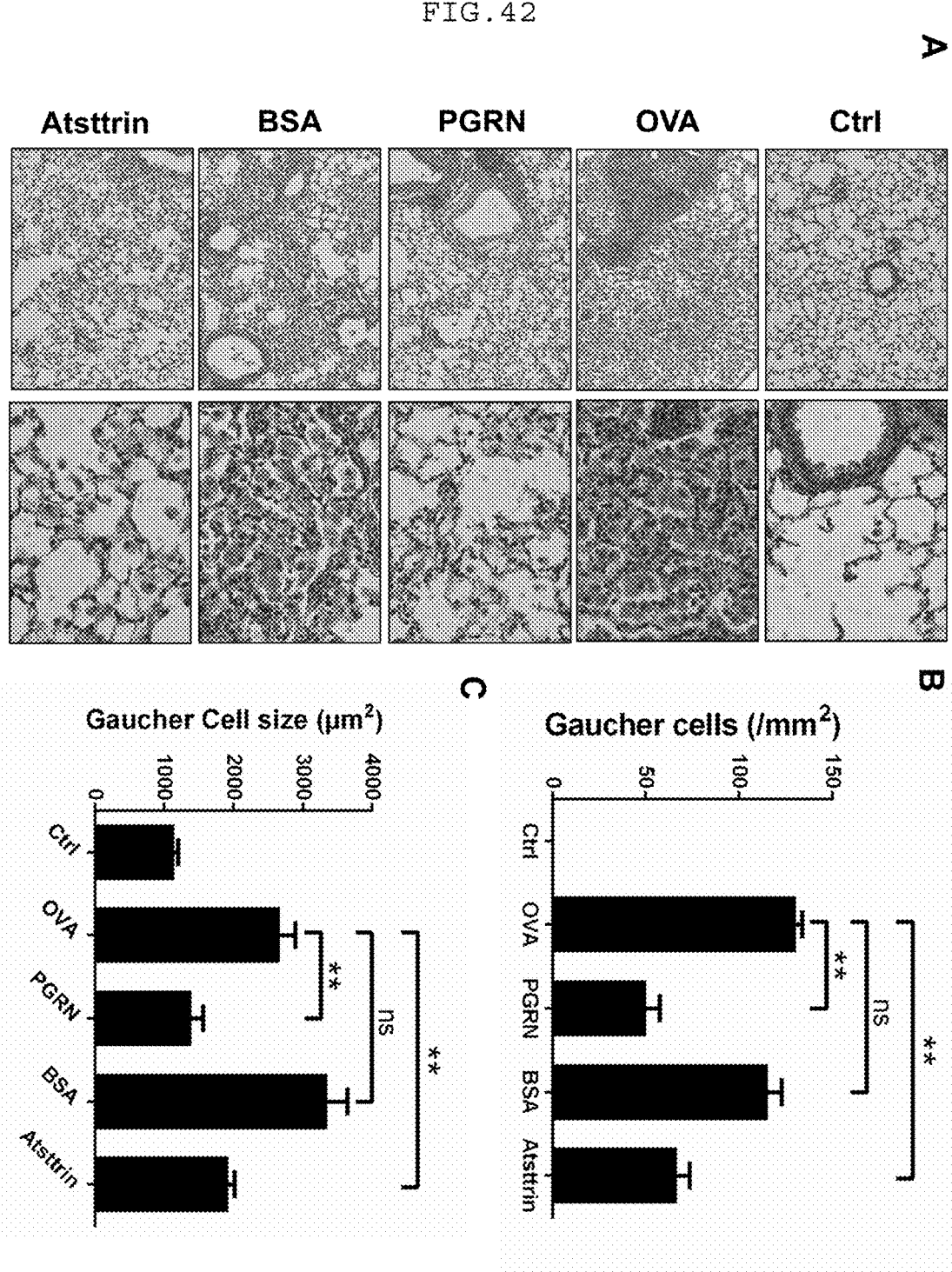
FIG. 42. PGRN and Atsttrin have therapeutic effect to treat Gaucher's disease. 8 week-old PGRN KO mice were induced Gaucher's disease by challenging with OVA as described previously. Some groups of mice were I.P injected with recombinant PGRN protein, BSA, and Atsttrin (4 mg/kg/week) for four weeks (n=8 per group). (A) The histology changes of lung tissues were examined by H&E staining. (B) Quantifications of Gaucher cell numbers. (C) Quantification of Gaucher cell sizes. (**$p<0.01$)

Atsttrin was then evaluated versus PGRN in PGRN KO mice. PGRN KO mice were induced Gaucher's disease by challenging with OVA as described above. KO mice were injected (i.p.) with either recombinant PGRN protein, BSA, or Atsttrin (4 mg/kg/week) for four weeks. Then, lung tissues changes were examined histologically, Gaucher cell numbers quantified and Gaucher cell sizes determined. The results are provided in FIG. 42. Animals treated with either PGRN or Atsttrin showed similar histology and the Gaucher cell number and cell size were reduced with either of PGRN or PGRN derivative peptide Atsttrin treatment. The degree of significance with either PGRN or Atsttrin was similar.

Example 3

Figure 43:
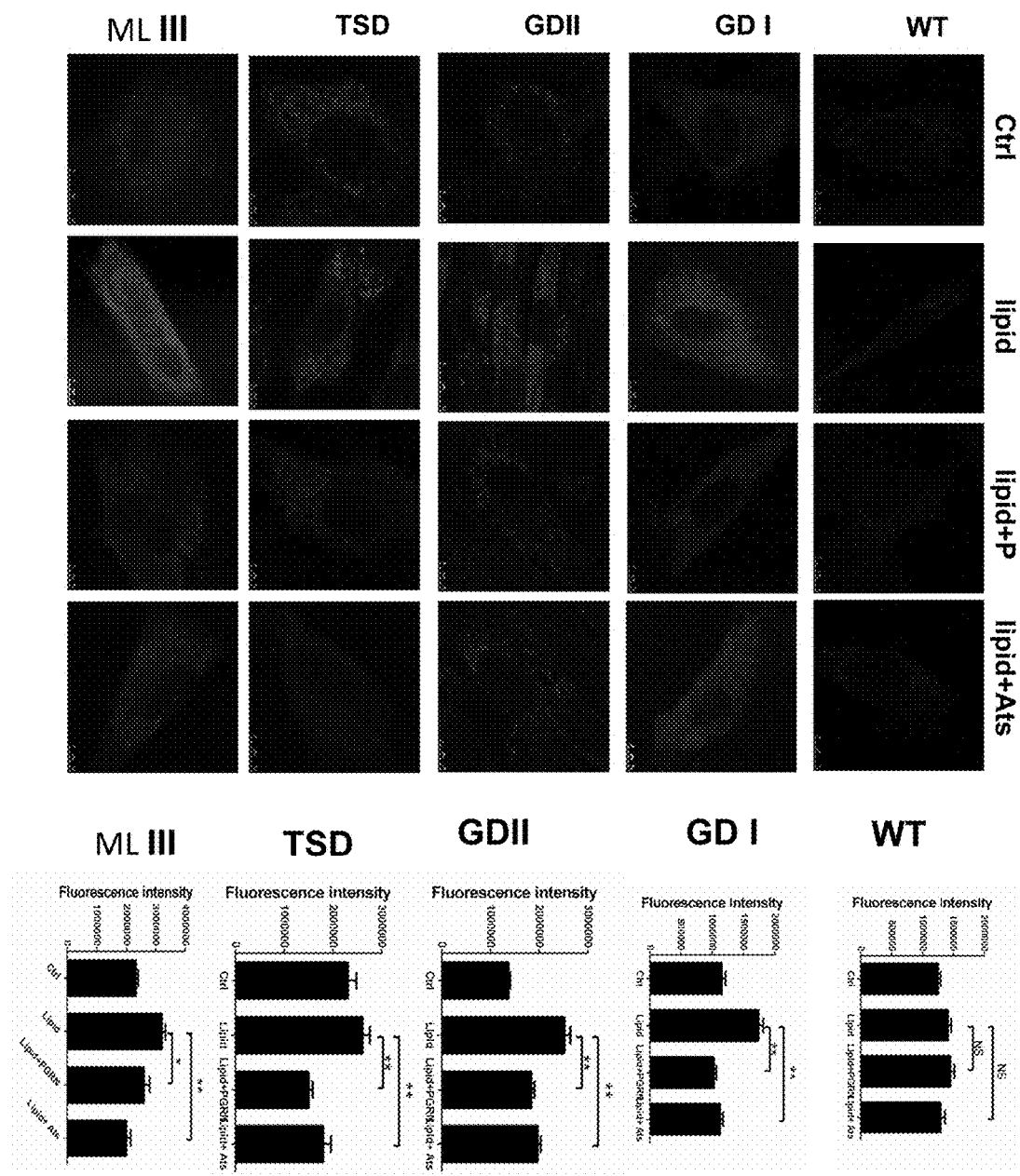
FIG. 43. LSD fibroblasts that can be treated by both PGRN and Atsttrin. LSD fibroblasts were challenged with lipid alone or with recombinant PGRN or Atsttrin (0.4 µg/ml), respectively for 24 hours. The lysosome was stained with lysotracker-red. Ten images for each sample were randomly taken under co-focal microscope, and lysosome storage were quantified based on fluorescence intensity by image J software. GDI, GDII: Gaucher's disease I and II; TSD: Tay-sachs disease; MLIII: mucolipidosis III. (**p<0.01)
Figure 44:
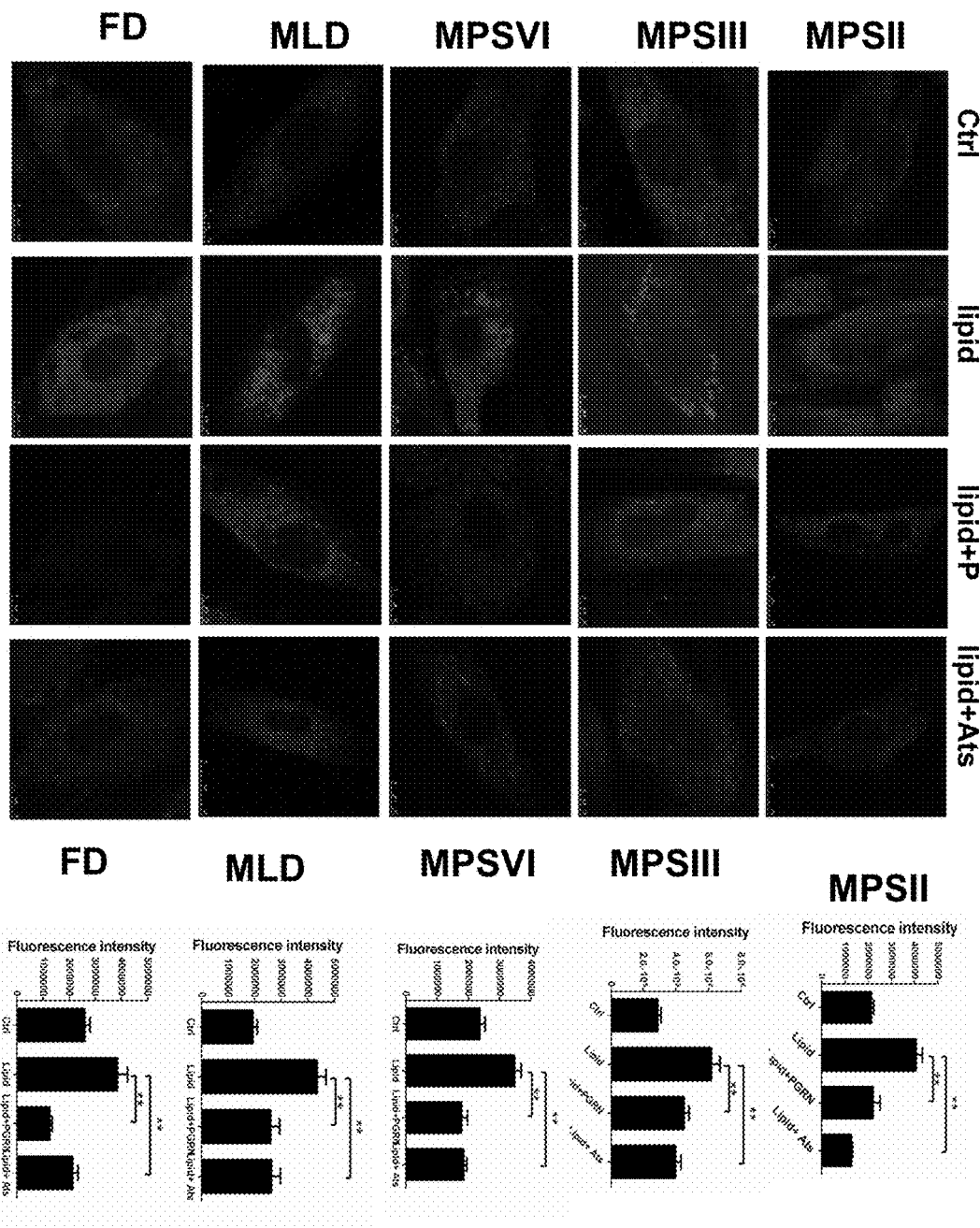
FIG. 44. LSD fibroblasts that can be treated by both PGRN and Atsttrin. LSD fibroblasts were challenged with lipid alone or with recombinant PGRN or Atsttrin (0.4 µg/ml), respectively for 24 hours. The lysosome was stained with lysotracker-red. Ten images for each sample were randomly taken under co-focal microscope, and lysosome storage were quantified based on fluorescence intensity by image J software. MPSII, MPSIII, MPSVI: Mucopolysaccharidosis Type II, III, VI; MLD: metachromatic leukodystrophy; FD: Farber disease. (**p<0.01)

PGRN Derivative Peptide Atsttrin Effectiveness in Various Lysosomal Storage Diseases Next, fibroblasts from LSD patients were obtained and treated with either PGRN or Atsttrin. Fibroblasts were evaluated from patients with various lysosomal storage diseases, including Gaucher's disease (GD); Tay-sachs disease (TSD); mucolipidosis (ML); mucopolysaccharidosis (MPS); metachromatic leukodystrophy (MLD); and Farber disease (FD). For each set of LSD disease fibroblasts, LSD fibroblasts were challenged with lipid alone or in combination with recombinant PGRN or Atsttrin (0.4 μg/ml), respectively for 24 hours. The lysosome was stained with lysotracker-red. Ten images for each sample were randomly taken under confocal microscope, and lysosome storage were quantified based on fluorescence intensity by image J software. The results are depicted in FIG. 43 and FIG. 44. As shown in the results, both Atsttrin and PGRN were effective and lysosome storage was significantly reduced in all LSD disease fibroblasts for Gaucher's disease Type I and II (GDI and GDII), Tay-sachs disease (TSD); mucolipidosis III (MLIII), mucopolysaccharidosis II, III and VI (MPSII, MPSIII, MPSVI), metachromatic leukodystrophy (MLD), and Farber disease (FD).

Figure 45:
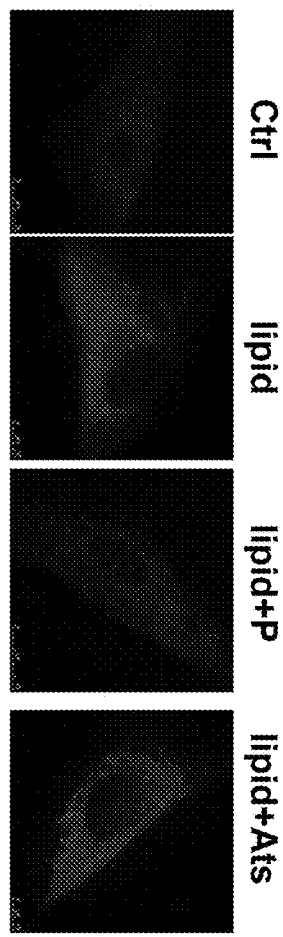
FIG. 45. PGRN, but not Atsttrin rescues lysosome storage in GD III after lipid challenge. fibroblasts from GD III were challenged with lipid alone or with recombinant PGRN or Atsttrin (0.4 µg/ml), respectively for 24 hours. The lysosome was stained with lysotracker-red. Ten images for each sample were randomly taken under co-focal microscope, and lysosome storage were quantified based on fluorescence intensity by image J software. (**p<0.01)
Figure 45:
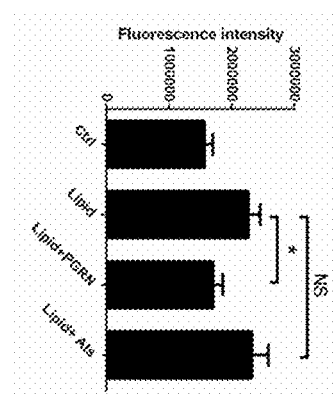

Fibroblasts from the chronic neuropathic form Gaucher's disease type III (GDIII) were evaluated. Fibroblasts from GD III patients were challenged with lipid alone or with recombinant PGRN or Atsttrin (0.4 µg/ml), respectively for 24 hours. The lysosome was stained with lysotracker-red and ten images for each sample were randomly taken and lysosome storage quantified based on fluorescence intensity. In this study, PGRN was significantly effective, however lysosome storage, as evaluated by fluorescence intensity, was not significantly reduced with Atsttrin treatment (FIG. 45).

Figure 46:
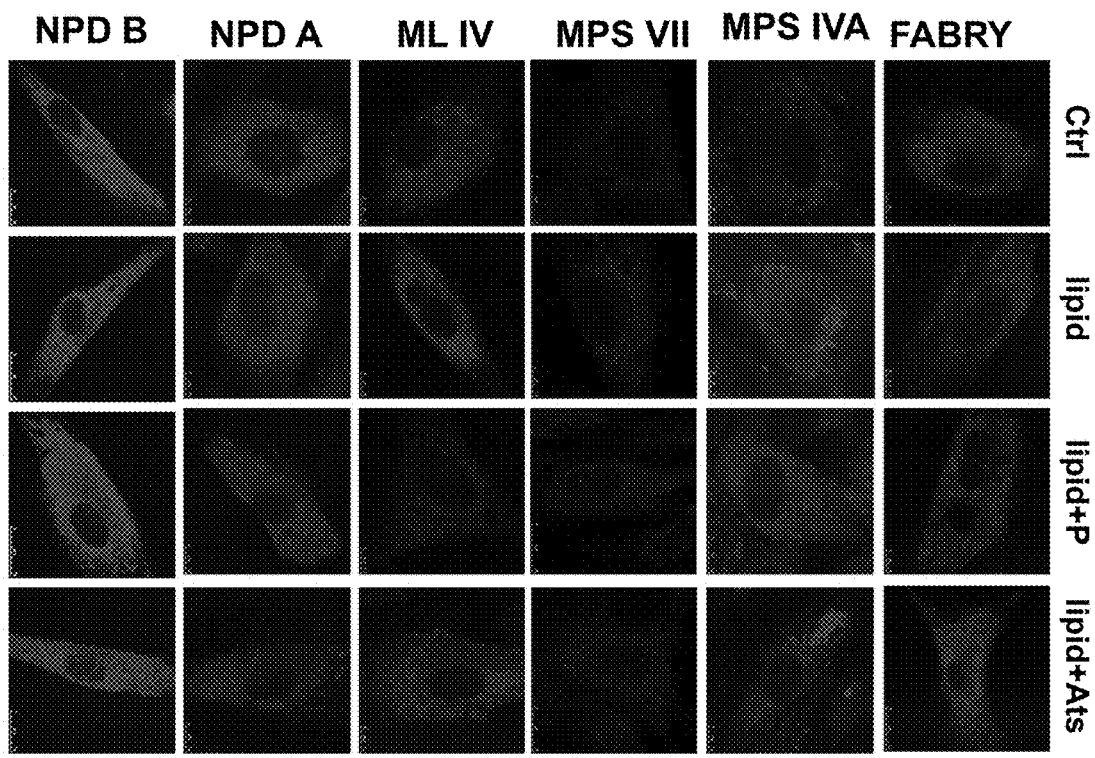
FIG. 46. LSD fibroblasts that both PGRN and Atsttrin show minimal effect to reduce lysosome storages. LSD fibroblasts were challenged with lipid alone or with recombinant PGRN or Atsttrin (0.4 µg/ml), respectively for 24 hours. The lysosome was stained with lysotracker-red. Ten images for each sample were randomly taken under co-focal microscope, and lysosome storage were quantified based on fluorescence intensity by image J software. ML: mucolipidosis; MPS: mucopolysaccharidosis NPD: Niemann-Pick disease.
Figure 46:
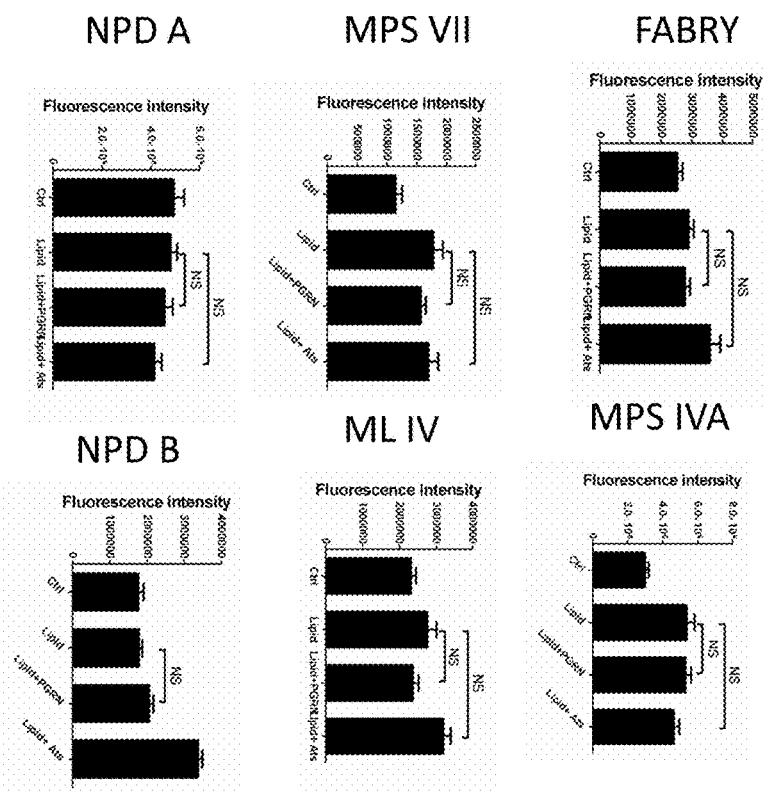

In LSD fibroblast studies, some diseased fibroblasts showed more minimal effects of PGRN or Atsttrin to reduce lysosome storage. These are only a single set of experiments, however. Using the same approach as noted above, LSD fibroblasts from each of Fabry disease (FABRY) mucolipidosis IV (MLIV); mucopolysaccharidosis IVA and VII (MPSIVA and MPSVII) and Niemann-Pick disease A and B (NPDA and NPDB) were evaluated by challenging the LSD fibroblasts with lipid alone or recombinant PGRN or Atsttrin (0.4 µg/ml) (FIG. 46). In each of these specific LSD fibroblasts, effects of neither PGRN or Atsttrin were found to be significant.

Figure 47:
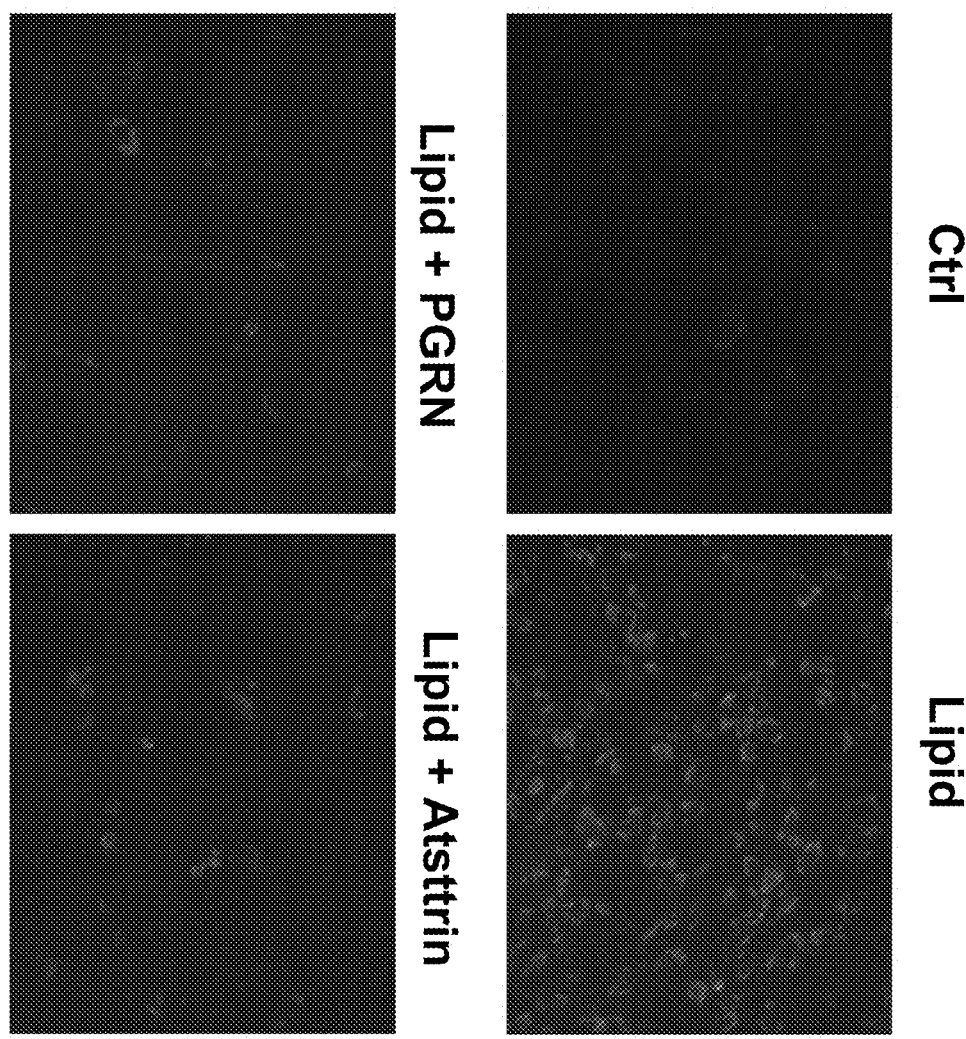
FIG. 47. PGRN and Atsttrin rescue lysosome storage in Krabbe Disease. Fibroblasts from Krabbe Disease were challenged with lipid alone or with recombinant PGRN or Atsttrin (0.4 µg/ml), respectively for 24 hours. The lysosome was stained with lysotracker-red, and ten images were taken under co-focal microscope.

LSD fibroblasts from Krabbe Disease patients were similarly evaluated (FIG. 47). Both PGRN and Atsttrin were effective to significantly reduce lysosome lipid storage in Krabbe Disease patient fibroblasts.

Taken together, these studies demonstrate remarkable effectiveness of both progranulin PGRN and progranulin derivative peptides, as exemplified by PGRN peptide Atsttrin, in reducing lysosomal storage in various recognized lysosomal storage diseases. Both PGRN and Atsttrin significantly reduce lipid buildup in lysosomes in cells derived from patients with LSDs including Gaucher's disease, Tay-Sachs disease, metachromatic leukodystrophy, Farber disease, Krabbe disease and in forms of mucolipidosis and mucopolysaccharidosis.

Example 4

Evaluations of Progranulin in the Lysososomal Storage Disease Tay-Sachs Disease

Tay-Sachs disease (also known as GM2 gangliosidosis or hexosaminidase A deficiency) is a rare autosomal recessive inherited disorder that progressively destroys nerve cells in the brain and spinal cord. Tay-Sachs disease results when an enzyme ($\beta$-hexosaminidase A) (FIG. 1) that helps break down fatty substances is absent and the disease occurs when harmful quantities of gangliosides accumulate in the brain's nerve cells, eventually leading to the premature death of the cells. A ganglioside is a form of sphingolipid, thus Tay-Sachs disease a member of the sphingolipidoses.

Tay-Sachs can become apparent in infancy (infantile Tay-Sachs disease), where infants lose motor skills such as turning over, sitting and crawling after age 3-6 months. As the disease progresses, the child's body loses function, leading to blindness, deafness, paralysis and death. Later-onset forms of Tay-Sachs disease also occur but are very rare, initially seen in ages 2-10 (juvenile Tay-Sachs disease) or a later rare form seen in adults aged 30s or 40s (adult/late-onset Tay-Sachs disease). Characteristic features include muscle weakness, loss of muscle coordination (ataxia), spasticity, and other movement problems, speech problems, cognitive decline, and mental illness. Mutations in the HEXA gene encoding the alpha subunit of the enzyme $\beta$-hexosaminidase A cause Tay-Sachs disease. $\beta$-hexosaminidase A enzyme is located in lysosomes and helps break down GM2 ganglioside. GM2 gangliosiode accumulates in lysosomes to toxic levels. Patients with and carriers of Tay-Sachs can be identified by a blood test that measures hexosaminidase A activity or by evaluating for mutations in the HEXA gene. Tay-Sachs disease is noted as increased in prevalence in Ashkenazi Jewish people. A four base pair insertion in exon 11 (1278insTATC) resulting in an altered reading frame for the HEXA gene has been identified as the most prevalent HEXA mutation in the Ashkenazi population. This mutation is also found in Cajun people in Louisiana. Two other unrelated mutations have been identified in French Canadians and associated with Tay-Sachs.

There is currently no cure or treatment for Tay-Sachs disease. Even with the best care, children with infantile Tay-Sachs disease die by the age of 4. Patients receive supportive care to ease the symptoms or extend life. In late-onset Tay-Sachs, medication (e.g., lithium for depression) can sometimes control psychiatric symptoms and seizures. Recently, researchers discovered that Pyrimethamine can increase $\beta$-hexosaminidase activity, thus potentially slowing down the progression of Late-Onset Tay-Sachs disease (Clarke J T, et al (2004) *Molecular Genetics and Metabolism* 102 (1): 6-12; Osher E, et al (2011) *Mol. Genet. Metab.* (Molecular Genetics and Metabolism) 102 (3): 356-63).

The above example studies and FIG. 33 evaluated lysosomes in fibroblasts from LSD patients, including Tay-Sachs disease patients. Fibroblasts from healthy control and different LSDs including Tay-Sachs disease were treated with progranulin (PGRN) with and without lipid stimulation. PGRN significantly corrected lysosomes in Tay-Sachs disease patient fibroblasts. The following studies were undertaken to additionally evaluate the role of PGRN in Tay-Sachs disease and as a modulator.

Figure 37:
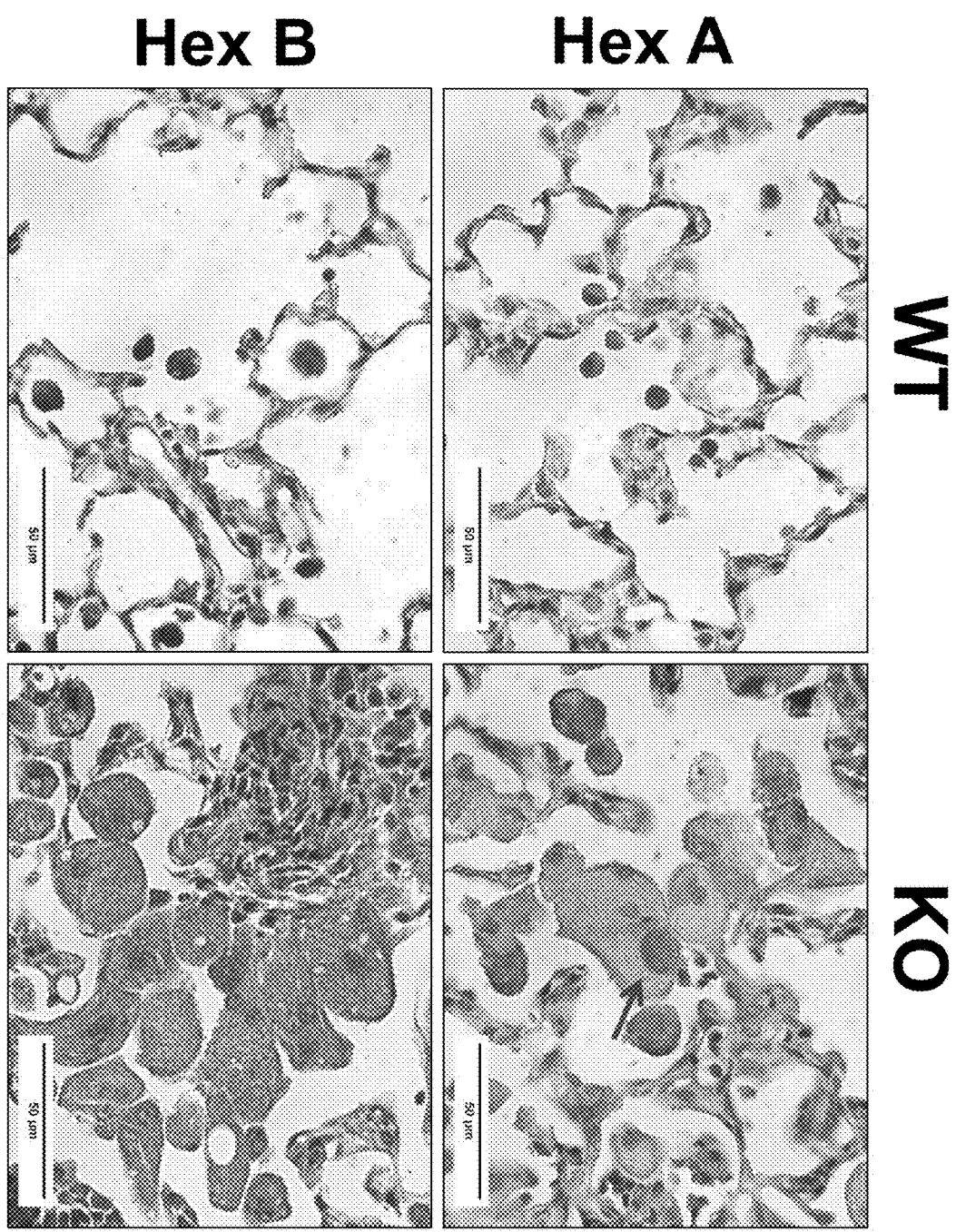
FIG. 37. HexA, but not HexB were aggregated in PGRN KO mice after OVA challenge. Lung tissues from WT and PGRN KO mice after OVA challenge were stained with HexA and HexB by immunohistochemistry. The results show that HexA, but not HexB is aggregated in PGRN KO mice.

First, levels of the HexA protein and also HexB (which encodes the beta subunit of the enzyme ($\beta$-hexosaminidase A) were evaluated in PGRN KO mice. Lung tissues from WT and PGRN KO mice after OVA challenge (described above in earlier examples) were stained for HexA and HexB by immunohistochemistry (HexA antibody sc-376777, and HexB antibody sc-134581 are from Santa Cruz). The results are depicted in FIG. 37 and demonstrate that HexA but not HexB is aggregated in PGRN KO mice.

Figure 38:
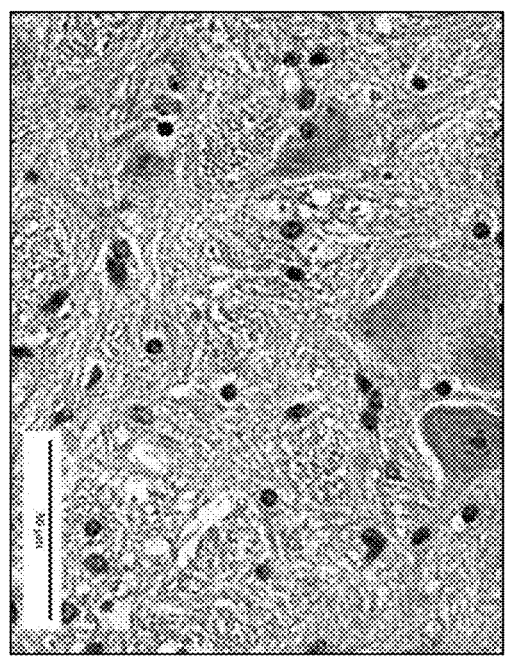
FIG. 38. Aged PGRN KO mice have elevated expression of GM2 in brain. Brain tissue from aged WT and PGRN KO mice were stained with GM2 antibody by immunohistochemistry.
Figure 38:
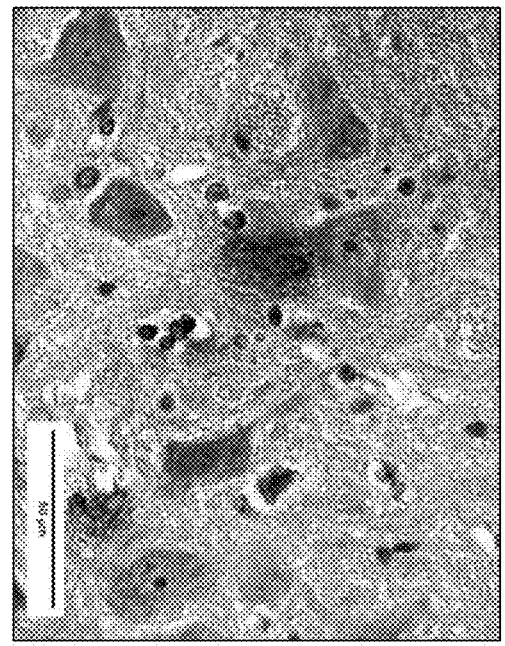

Also, aged PGRN KO mice were evaluated for GM2 ganglioside in their brains. Brain tissue from aged PGRN KO mice was stained with a GM2 antibody by immunohistochemistry and compared to WT mice (GM2 antibody, Cat. No. 345759, EMD Millipore). FIG. 38 shows elevated GM2 in the brain of aged PGRN KO mice. Thus we conclude that with PGRN knockout, HexA is aggregated and GM2 accumulated in the brain. Absence of PGRN results in accumulation of GM2 ganglioside and altered HexA, which are both indicators of Tay-Sachs disease, further indicating a role of PGRN in Tay-Sachs disease and providing further reasoning for PGRN effects in Tay-Sachs disease patients and patient cells.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method for facilitating lysosomal delivery of glucocerebrisidase (GBA) and of β-hexosaminidase A (HexA) in an animal comprising administering to said animal isolated full length mammalian progranulin (PGRN).

2. The method of claim 1 for facilitating delivery of glucocerebrisidase (GBA) in a patient with Gaucher's Disease comprising administering to said patient isolated PGRN wherein said PGRN comprises an amino acid sequence as set out in SEQ ID NO: 2 or 3.

3. A method for treating or alleviating a lysosomal storage disease in an animal comprising administering to said animal isolated full length mammalian PGRN, wherein the lysosomal storage disease is selected from Gaucher's Disease (GD) Type I, II or III, Farber disease, mucolipidosis (ML) III, mucopolysaccharidosis (MPS) II, III VI, metachromatic leukodystrophy (MLD) and Krabbe disease (KD).

4. The method of claim 3 comprising additionally administering one or more lysosomal enzyme which is reduced, absent, mutated or altered in the lysosomal storage disease.

5. The method of claim 3 comprising additionally administering the lysosmal enzyme glucocerebrisidase (GBA) or an active fragment or recombinant form thereof for treating or alleviating Gaucher's Disease.

6. The method of claim 4 wherein the lysosomal enzyme is selected from one or more of a glucocerebrosidase, α-galactosidase, β-galactosidase, and sphingomyelinase.

7. The method of claim 3 wherein said PGRN comprises an amino acid sequence as set out in SEQ ID NO: 2 or 3.

8. A method for treating or alleviating a lysosomal storage disease in an animal comprising administering to said animal atsttrin, wherein the lysosomal storage disease is selected from Gaucher's Disease (GD) I or II, Tay-Sachs disease, Farber disease, mucolipidosis (ML) III, mucopolysaccharidosis (MPS) II, III, VI, metachromatic leukodystrophy (MLD) and Krabbe disease (KD).

9. The method of claim 8 comprising additionally administering one or more lysosomal enzyme which is reduced, absent, mutated or altered in the lysosomal storage disease.

10. The method of claim 8 comprising additionally administering the lysosmal enzyme glucocerebrisidase (GBA) or an active fragment or recombinant form thereof for treating or alleviating Gaucher's Disease.

11. The method of claim 8 comprising additionally administering the lysosmal enzyme β-hexosaminidase A (HexA) or an active fragment or recombinant form thereof for treating or alleviating Tay-Sachs disease.

12. The method of claim 9 wherein the lysosomal enzyme is selected from one or more of a glucocerebrosidase, α-galactosidase, β-galactosidase, β-hexosaminidase and sphingomyelinase.

13. The method of claim 8 wherein said atsttrin comprises an amino acid sequence as set out in SEQ ID NO: 4.

14. The method of claim 1 wherein the animal is a human.

15. The method of claim 3 wherein the animal is a human.
16. The method of claim 8 wherein the animal is a human.

* * * * *

UNITED STATES PATENT AND TRADEMARK OFFICE
CERTIFICATE OF CORRECTION

PATENT NO. : 10,357,542 B2
APPLICATION NO. : 15/116122
DATED : July 23, 2019
INVENTOR(S) : Chuanju Liu et al.

It is certified that error appears in the above-identified patent and that said Letters Patent is hereby corrected as shown below:

In the Specification

At Column 1, Line 18, below the Cross Reference to Related Applications paragraph and before the Field of the Invention paragraph, the paragraph should read:
--GOVERNMENTAL SUPPORT
This invention was made with government support under grant numbers R01 AR061484 and R01 AR062207 awarded by The National Institutes of Health. The government has certain rights in the invention.--

Signed and Sealed this
Twentieth Day of December, 2022

Katherine Kelly Vidal
*Director of the United States Patent and Trademark Office*

SEQUENCE LISTING

<160> NUMBER OF SEQ ID NOS: 24

<210> SEQ ID NO 1
<211> LENGTH: 53
<212> TYPE: PRT
<213> ORGANISM: Artificial sequence
<220> FEATURE:
<223> OTHER INFORMATION: consensus
<220> FEATURE:
<221> NAME/KEY: VARIANT
<222> LOCATION: (2)..(2)
<223> OTHER INFORMATION: X is any amino acid
<220> FEATURE:
<221> NAME/KEY: VARIANT
<222> LOCATION: (3)..(3)
<223> OTHER INFORMATION: X is any amino acid
<220> FEATURE:
<221> NAME/KEY: VARIANT
<222> LOCATION: (4)..(4)
<223> OTHER INFORMATION: X is any amino acid
<220> FEATURE:
<221> NAME/KEY: VARIANT
<222> LOCATION: (5)..(5)
<223> OTHER INFORMATION: X is any amino acid
<220> FEATURE:
<221> NAME/KEY: VARIANT
<222> LOCATION: (6)..(6)
<223> OTHER INFORMATION: X is any amino acid
<220> FEATURE:
<221> NAME/KEY: VARIANT
<222> LOCATION: (7)..(7)
<223> OTHER INFORMATION: X is any amino acid or none
<220> FEATURE:
<221> NAME/KEY: VARIANT
<222> LOCATION: (9)..(9)
<223> OTHER INFORMATION: X is any amino acid
<220> FEATURE:
<221> NAME/KEY: VARIANT
<222> LOCATION: (10)..(10)
<223> OTHER INFORMATION: X is any amino acid
<220> FEATURE:
<221> NAME/KEY: VARIANT
<222> LOCATION: (11)..(11)
<223> OTHER INFORMATION: X is any amino acid
<220> FEATURE:
<221> NAME/KEY: VARIANT
<222> LOCATION: (12)..(12)
<223> OTHER INFORMATION: X is any amino acid
<220> FEATURE:
<221> NAME/KEY: VARIANT
<222> LOCATION: (13)..(13)
<223> OTHER INFORMATION: X is any amino acid
<220> FEATURE:
<221> NAME/KEY: VARIANT
<222> LOCATION: (16)..(16)
<223> OTHER INFORMATION: X is any amino acid
<220> FEATURE:
<221> NAME/KEY: VARIANT
<222> LOCATION: (17)..(17)
<223> OTHER INFORMATION: X is any amino acid
<220> FEATURE:
<221> NAME/KEY: VARIANT
<222> LOCATION: (18)..(18)
<223> OTHER INFORMATION: X is any amino acid
<220> FEATURE:
<221> NAME/KEY: VARIANT
<222> LOCATION: (19)..(19)
<223> OTHER INFORMATION: X is any amino acid
<220> FEATURE:
<221> NAME/KEY: VARIANT
<222> LOCATION: (20)..(20)
<223> OTHER INFORMATION: X is any amino acid
<220> FEATURE:
<221> NAME/KEY: VARIANT
<222> LOCATION: (21)..(21)
<223> OTHER INFORMATION: X is any amino acid
<220> FEATURE:
<221> NAME/KEY: VARIANT -continued

```
<222> LOCATION: (22)..(22)
<223> OTHER INFORMATION: X is any amino acid
<220> FEATURE:
<221> NAME/KEY: VARIANT
<222> LOCATION: (23)..(23)
<223> OTHER INFORMATION: X is any amino acid
<220> FEATURE:
<221> NAME/KEY: VARIANT
<222> LOCATION: (26)..(26)
<223> OTHER INFORMATION: X is any amino acid
<220> FEATURE:
<221> NAME/KEY: VARIANT
<222> LOCATION: (27)..(27)
<223> OTHER INFORMATION: X is any amino acid
<220> FEATURE:
<221> NAME/KEY: VARIANT
<222> LOCATION: (28)..(28)
<223> OTHER INFORMATION: X is any amino acid
<220> FEATURE:
<221> NAME/KEY: VARIANT
<222> LOCATION: (29)..(29)
<223> OTHER INFORMATION: X is any amino acid
<220> FEATURE:
<221> NAME/KEY: VARIANT
<222> LOCATION: (30)..(30)
<223> OTHER INFORMATION: X is any amino acid
<220> FEATURE:
<221> NAME/KEY: VARIANT
<222> LOCATION: (31)..(31)
<223> OTHER INFORMATION: X is any amino acid
<220> FEATURE:
<221> NAME/KEY: VARIANT
<222> LOCATION: (34)..(34)
<223> OTHER INFORMATION: X is any amino acid
<220> FEATURE:
<221> NAME/KEY: VARIANT
<222> LOCATION: (36)..(36)
<223> OTHER INFORMATION: X is any amino acid
<220> FEATURE:
<221> NAME/KEY: VARIANT
<222> LOCATION: (37)..(37)
<223> OTHER INFORMATION: X is any amino acid
<220> FEATURE:
<221> NAME/KEY: VARIANT
<222> LOCATION: (42)..(42)
<223> OTHER INFORMATION: X is any amino acid
<220> FEATURE:
<221> NAME/KEY: VARIANT
<222> LOCATION: (43)..(43)
<223> OTHER INFORMATION: X is any amino acid
<220> FEATURE:
<221> NAME/KEY: VARIANT
<222> LOCATION: (44)..(44)
<223> OTHER INFORMATION: X is any amino acid
<220> FEATURE:
<221> NAME/KEY: VARIANT
<222> LOCATION: (45)..(45)
<223> OTHER INFORMATION: X is any amino acid
<220> FEATURE:
<221> NAME/KEY: VARIANT
<222> LOCATION: (47)..(47)
<223> OTHER INFORMATION: X is any amino acid
<220> FEATURE:
<221> NAME/KEY: VARIANT
<222> LOCATION: (48)..(48)
<223> OTHER INFORMATION: X is any amino acid
<220> FEATURE:
<221> NAME/KEY: VARIANT
<222> LOCATION: (49)..(49)
<223> OTHER INFORMATION: X is any amino acid
<220> FEATURE:
<221> NAME/KEY: VARIANT
<222> LOCATION: (50)..(50)
<223> OTHER INFORMATION: X is any amino acid
<220> FEATURE:
<221> NAME/KEY: VARIANT
<222> LOCATION: (51)..(51)
<223> OTHER INFORMATION: X is any amino acid
<220> FEATURE:
```

```
<221> NAME/KEY: VARIANT
<222> LOCATION: (52)..(52)
<223> OTHER INFORMATION: X is any amino acid or none

<400> SEQUENCE: 1

Cys Xaa Xaa Xaa Xaa Xaa Cys Xaa Xaa Xaa Xaa Cys Cys Xaa
1               5                   10                  15

Xaa Xaa Xaa Xaa Xaa Xaa Cys Cys Xaa Xaa Xaa Xaa Xaa Cys
            20                  25                  30

Cys Xaa Asp Xaa Xaa His Cys Cys Pro Xaa Xaa Xaa Cys Xaa Xaa
        35                  40                  45

Xaa Xaa Xaa Xaa Cys
    50

<210> SEQ ID NO 2
<211> LENGTH: 593
<212> TYPE: PRT
<213> ORGANISM: Homo sapiens

<400> SEQUENCE: 2

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Pro Cys Gln Val Asp
    50                  55                  60

Ala His Cys Ser Ala Gly His Ser Cys Ile Phe Thr Val Ser Gly Thr
65              70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
            165                 170                 175

Arg Cys Ile Thr Pro Thr Gly Thr His Pro Leu Ala Lys Lys Leu Pro
        180                 185                 190

Ala Gln Arg Thr Asn Arg Ala Val Ala Leu Ser Ser Val Met Cys
    195                 200                 205

Pro Asp Ala Arg Ser Arg Cys Pro Asp Gly Ser Thr Cys Cys Glu Leu
210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
            245                 250                 255

Gln Ser Lys Cys Leu Ser Lys Glu Asn Ala Thr Thr Asp Leu Leu Thr
        260                 265                 270

Lys Leu Pro Ala His Thr Val Gly Asp Val Lys Cys Asp Met Glu Val
    275                 280                 285
```

Ser Cys Pro Asp Gly Tyr Thr Cys Cys Arg Leu Gln Ser Gly Ala Trp
290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
        435                 440                 445

Ser Cys Pro Val Gly Gln Thr Cys Cys Pro Ser Leu Gly Gly Ser Trp
450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
        515                 520                 525

Asp Asn Gln Thr Cys Cys Arg Asp Asn Arg Gln Gly Trp Ala Cys Cys
530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu

<210> SEQ ID NO 3
<211> LENGTH: 588
<212> TYPE: PRT
<213> ORGANISM: Mus musculus

<400> SEQUENCE: 3

Met Trp Ile Leu Val Ser Trp Leu Ala Leu Ala Arg Leu Val Ala
1               5                   10                  15

Gly Thr Gln Cys Pro Asp Gly Gln Phe Cys Pro Val Ala Cys Cys Leu
            20                  25                  30

Asp Gln Gly Gly Ala Asn Tyr Ser Cys Cys Asn Pro Leu Leu Asp Thr
        35                  40                  45

Trp Pro Ile Ile Thr Ser Arg Arg Leu Asp Gly Ser Cys Gln Ile Arg
    50                  55                  60

```
Asp His Cys Pro Asp Gly Tyr Ser Cys Leu Leu Thr Val Ser Gly Thr
 65                  70                  75                  80

Ser Ser Cys Cys Pro Phe Ser Glu Gly Val Ser Cys Asp Asp Gly Gln
                 85                  90                  95

His Cys Cys Pro Arg Gly Phe His Cys Ser Ala Asp Gly Lys Ser Cys
            100                 105                 110

Ser Gln Ile Ser Asp Ser Leu Leu Gly Ala Val Gln Cys Pro Gly Ser
        115                 120                 125

Gln Phe Glu Cys Pro Asp Ser Ala Thr Cys Cys Ile Met Ile Asp Gly
    130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                165                 170                 175

Cys Ile Ser Pro Thr Gly Thr His Pro Leu Leu Lys Lys Phe Pro Ala
            180                 185                 190

Gln Arg Thr Asn Arg Ala Val Ala Ser Phe Ser Val Val Cys Pro Asp
        195                 200                 205

Ala Lys Thr Gln Cys Pro Asp Asp Ser Thr Cys Cys Glu Leu Pro Thr
210                 215                 220

Gly Lys Tyr Gly Cys Cys Pro Met Pro Asn Ala Ile Cys Cys Ser Asp
225                 230                 235                 240

His Leu His Cys Cys Pro Gln Asp Thr Val Cys Asp Leu Ile Gln Ser
                245                 250                 255

Lys Cys Ile Ser Lys Asp Tyr Thr Thr Asp Leu Met Thr Lys Leu Pro
            260                 265                 270

Gly Tyr Pro Val Asn Glu Val Lys Cys Asp Leu Glu Val Ser Cys Pro
        275                 280                 285

Asp Gly Tyr Thr Cys Cys Arg Leu Asn Thr Gly Ala Trp Gly Cys Cys
    290                 295                 300

Pro Phe Thr Lys Ala Val Cys Cys Glu Asp His Ile His Cys Cys Pro
305                 310                 315                 320

Ala Gly Phe Gln Cys His Thr Glu Thr Gly Thr Cys Glu Leu Gly Val
                325                 330                 335

Leu Gln Val Pro Trp Met Lys Lys Val Thr Ala Ser Leu Ser Leu Pro
            340                 345                 350

Asp Pro Gln Ile Leu Lys Asn Asp Val Pro Cys Asp Asp Phe Ser Ser
        355                 360                 365

Cys Pro Ser Asn Asn Thr Cys Cys Arg Leu Ser Ser Gly Asp Trp Gly
    370                 375                 380

Cys Cys Pro Met Pro Glu Ala Val Cys Cys Leu Asp His Gln His Cys
385                 390                 395                 400

Cys Pro Gln Gly Phe Lys Cys Met Asp Glu Gly Tyr Cys Gln Lys Gly
                405                 410                 415

Asp Arg Met Val Ala Gly Leu Glu Lys Met Pro Val Arg Gln Thr Thr
            420                 425                 430

Leu Leu Gln His Gly Asp Ile Gly Cys Asp Gln His Thr Ser Cys Pro
        435                 440                 445

Val Gly Gln Thr Cys Cys Pro Ser Leu Lys Gly Ser Trp Ala Cys Cys
    450                 455                 460

Gln Leu Pro His Ala Val Cys Cys Glu Asp Arg Gln His Cys Cys Pro
465                 470                 475                 480
```

```
Ala Gly Tyr Thr Cys Asn Val Lys Ala Arg Thr Cys Glu Lys Asp Ala
                485                 490                 495

Gly Ser Val Gln Pro Ser Met Asp Leu Thr Phe Gly Ser Lys Val Gly
            500                 505                 510

Asn Val Glu Cys Gly Ala Gly His Phe Cys His Asp Asn Gln Ser Cys
            515                 520                 525

Cys Lys Asp Ser Gln Gly Gly Trp Ala Cys Cys Pro Tyr Val Lys Gly
            530                 535                 540

Val Cys Cys Arg Asp Arg His Cys Cys Pro Ile Gly Phe His Cys
545                 550                 555                 560

Ser Ala Lys Gly Thr Lys Cys Leu Arg Lys Lys Thr Pro Arg Trp Asp
                565                 570                 575

Ile Leu Leu Arg Asp Pro Ala Pro Arg Pro Leu Leu
                580                 585

<210> SEQ ID NO 4
<211> LENGTH: 158
<212> TYPE: PRT
<213> ORGANISM: Homo sapiens

<400> SEQUENCE: 4

Pro Gln Ala Ser Cys Cys Glu Asp Arg Val His Cys Cys Pro His Gly
1               5                   10                  15

Ala Phe Cys Asp Leu Val His Thr Arg Cys Ile Thr Pro Thr Gly Thr
            20                  25                  30

His Pro Leu Ala Lys Lys Leu Pro Ala Gln Arg Thr Asn Arg Ala Val
        35                  40                  45

Ala Leu Ser Ser Ser Ala Ser Ser Lys Glu Asn Ala Thr Thr Asp Leu
    50                  55                  60

Leu Thr Lys Leu Pro Ala His Thr Val Gly Asp Val Lys Cys Asp Met
65                  70                  75                  80

Glu Val Ser Cys Pro Asp Gly Tyr Thr Cys Cys Arg Leu Gln Ser Gly
                85                  90                  95

Ala Trp Pro Trp Cys Glu Gln Gly Pro His Gln Val Pro Trp Met Glu
            100                 105                 110

Lys Ala Pro Ala His Leu Ser Leu Pro Asp Pro Gln Ala Leu Lys Arg
        115                 120                 125

Asp Val Pro Cys Asp Asn Val Ser Ser Cys Pro Ser Ser Asp Thr Cys
    130                 135                 140

Cys Gln Leu Thr Ser Gly Glu Trp Gly Cys Cys Pro Ile Pro
145                 150                 155

<210> SEQ ID NO 5
<211> LENGTH: 63
<212> TYPE: PRT
<213> ORGANISM: Homo sapiens

<400> SEQUENCE: 5

Ile Gln Cys Pro Asp Ser Gln Phe Glu Cys Pro Asp Phe Ser Thr Cys
1               5                   10                  15

Cys Val Met Val Asp Gly Ser Trp Gly Cys Cys Pro Met Pro Gln Ala
            20                  25                  30

Ser Cys Cys Glu Asp Arg Val His Cys Cys Pro His Gly Ala Phe Cys
        35                  40                  45

Asp Leu Val His Thr Arg Cys Ile Thr Pro Thr Gly Thr His Pro
    50                  55                  60
```

<210> SEQ ID NO 6
<211> LENGTH: 75
<212> TYPE: PRT
<213> ORGANISM: Homo sapiens

<400> SEQUENCE: 6

Ser Lys Glu Asn Ala Thr Thr Asp Leu Leu Thr Lys Leu Pro Ala His
1               5                   10                  15

Thr Val Gly Asp Val Lys Cys Asp Met Glu Val Ser Cys Pro Asp Gly
            20                  25                  30

Tyr Thr Cys Cys Arg Leu Gln Ser Gly Ala Trp Gly Cys Cys Pro Phe
        35                  40                  45

Thr Gln Ala Val Cys Cys Glu Asp His Ile His Cys Cys Pro Ala Gly
    50                  55                  60

Phe Thr Cys Asp Thr Gln Lys Gly Thr Cys Glu
65                  70                  75

<210> SEQ ID NO 7
<211> LENGTH: 81
<212> TYPE: PRT
<213> ORGANISM: Homo sapiens

<400> SEQUENCE: 7

Gln Gly Pro His Gln Val Pro Trp Met Glu Lys Ala Pro Ala His Leu
1               5                   10                  15

Ser Leu Pro Asp Pro Gln Ala Leu Lys Arg Asp Val Pro Cys Asp Asn
            20                  25                  30

Val Ser Ser Cys Pro Ser Ser Asp Thr Cys Cys Gln Leu Thr Ser Gly
        35                  40                  45

Glu Trp Gly Cys Cys Pro Ile Pro Glu Ala Val Cys Cys Ser Asp His
    50                  55                  60

Gln His Cys Cys Pro Gln Gly Tyr Thr Cys Val Ala Glu Gly Gln Cys
65                  70                  75                  80

Gln

<210> SEQ ID NO 8
<211> LENGTH: 98
<212> TYPE: PRT
<213> ORGANISM: Homo sapiens

<400> SEQUENCE: 8

Pro Gln Ala Ser Cys Cys Glu Asp Arg Val His Cys Cys Pro His Gly
1               5                   10                  15

Ala Phe Cys Asp Leu Val His Thr Arg Cys Ile Thr Pro Thr Gly Thr
            20                  25                  30

His Pro Leu Ala Lys Lys Leu Pro Ala Gln Arg Thr Asn Arg Ala Val
        35                  40                  45

Ala Leu Ser Ser Ser Ala Ser Ser Lys Glu Asn Ala Thr Thr Asp Leu
    50                  55                  60

Leu Thr Lys Leu Pro Ala His Thr Val Gly Asp Val Lys Cys Asp Met
65                  70                  75                  80

Glu Val Ser Cys Pro Asp Gly Tyr Thr Cys Cys Arg Leu Gln Ser Gly
                85                  90                  95

Ala Trp

<210> SEQ ID NO 9
<211> LENGTH: 103

<212> TYPE: PRT
<213> ORGANISM: Homo sapiens

<400> SEQUENCE: 9

```
Ser Lys Glu Asn Ala Thr Thr Asp Leu Leu Thr Lys Leu Pro Ala His
1               5                   10                  15

Thr Val Gly Asp Val Lys Cys Asp Met Glu Val Ser Cys Pro Asp Gly
            20                  25                  30

Tyr Thr Cys Cys Arg Leu Gln Ser Gly Ala Trp Pro Trp Cys Glu Gln
        35                  40                  45

Gly Pro His Gln Val Pro Trp Met Glu Lys Ala Pro Ala His Leu Ser
    50                  55                  60

Leu Pro Asp Pro Gln Ala Leu Lys Arg Asp Val Pro Cys Asp Asn Val
65                  70                  75                  80

Ser Ser Cys Pro Ser Ser Asp Thr Cys Cys Gln Leu Thr Ser Gly Glu
                85                  90                  95

Trp Gly Cys Cys Pro Ile Pro
            100
```

<210> SEQ ID NO 10
<211> LENGTH: 8980
<212> TYPE: DNA
<213> ORGANISM: Homo sapiens

<400> SEQUENCE: 10

```
cacctgccag ttaaaatctt cccagactca gctcaaggag atgctcctaa ggtggaatga      60
aatctcttct tccccacctg agacaatct  acttcctctc cctacacctg caactggcg      120
cacaaccttg tatcttaaat tagattcagc ctgagactgt ctcccaccaa tccctgctcc     180
ctgtcctgct gagcaccttg aggaaagggc tttgggctg  tttatctttg tcctggaaac     240
catccttcaa ctcactctgg ggcctgccta gcatgtcaac cgagtttgga gaatagggca     300
gaatagggca ggacaggaca ggacaagaca gggcaggata ggataggagc gagccagctc     360
agtagctcac atttgtaatc ccagcgcctt gggggctgc  ggtaggagaa tcgctttggg     420
agcaggagtt gcaggccgca gtgagctatg atcagcttgg gcgactgagc gagaccctgt     480
ctctaaaaca aacacacaag tccgggcgcg gtggctcatg cctgtaatct tagcactttg     540
ggaggccgag gtgggcggat cacgaggtca agaaatcgag accatcctgg ccaacatggt     600
gaaaccccgt ctctactaaa aatacaaaaa ttagctgggc gtggtggtgc gcgcctgtag     660
tcccagctac tcgggaggct gaggcaggag aatcgcttga acccgggagg cagaggttgc     720
agtgagccga gatcgtgcca ctgcactcca gcctggcgac agagtgagac tccgtctcag     780
aacaaacaaa caaaggata  gaaggcgag  cacaaatatt cccaattcat aacactccct     840
cgcactgtca atgccccaga cacgcgctat catctctagc aaactccccc aggcgcctgc     900
aggatgggtt aaggaaggcg acgagcacca gctgccctgc tgaggctgtc ccgacgtcac     960
atgattctcc aatcacatga tccctagaaa tggggtgtgg ggcgagagga agcagggagg    1020
agagtgattt gagtagaaaa gaaacacagc attccaggct ggccccacct ctatattgat    1080
aagtagccaa tgggagcggg tagccctgat ccctggccaa tggaaactga ggtaggcggg    1140
tcatcgcgct ggggtctgta gtctgagcgc taccggttg  ctgctgccca aggaccgcgg    1200
agtcggacgc aggtaggaga gcggccgcgc agacctctcg cctgctcctg cccaggggcc    1260
cgccagggcc atgtgagctt gaggttcccc tggagtctca gccggagaca acagaagaac    1320
cgcttactga aactccttgg gggttctgat acactagggg gagttttatg ggaaagagga    1380
```

```
agcagtaatt gcagtgacgc cccgttagaa ggggctttct acctccccag cattccccca   1440
aagcagggac cacaccattc ttgacccagc tccacccctg tcggtaggtg ctggcttctt   1500
cccctctcct ggtggtggtg ggtggttccc gcggcggcct ggagccggag gggcgcgcga   1560
ccctgggctg ggagctccga gggcctggga acgagacctg agaccttggc ttctcgaagg   1620
tagtagggac ttgggagtgg tgactgaacc tggtctggct cctccttact tcctcttgtt   1680
gcgggtggga cgagctagct tccgcctctc ccagccactt tttcctgctc atttgcagct   1740
aggttggctc cccttttggg aatttcctct cccccttggca ctcggagttg ggggtgcca   1800 cctagtggaa gataacggag ctagggtctt gaagaggctg ctgtcccctc tggctgtttt   1860
ggcggtgtag ggtggcatga gagactgcga ctcgcctcct catccctgtt tctgtatgcg   1920
agtgcttgta ttcagtagaa gcatacacta tactccctca atttagggta aacaggaggg   1980
gccacatgca caggtaattc accagggagc cgaacactcc tgtgcagaca gactccccTT   2040
cccagcaagc catggcagcg gacagcctgc tgagaacacc caggaagcag gcggtgccag   2100
ctgcaggtgc tttgcctggg agctgtgggg ctgaggagag ggtccactgt ccaggaccag   2160
tgaacttcat ccttatctgt ccaggaggtg gcctcttggg gatgctgagt taggggaggg   2220
gcacttgagg aaagccaggt ggagcagaga ggatgtgagt gactgggtgg gtgagatttc   2280
ctgcccctcc ccccgcagtg gtatccacac ctagactcgt ggggtaactg aggcacagac   2340
agagagcaac ttctcaggcc ctcacagttg gcaattctag gattaggacc caagtgcgat   2400
tttcaggcag tccctgtacc ctgtttctgt tgtacctgtt gcaccattcc caggcactgc   2460
ccatcgtgcc actagtgata tgaacccagg tccaatacgc tctggggcca tcaaagcctg   2520
acgtcaccat gacctgatgt gtgacgtgtt ataggtgtcc cttggtatct tcacggaact   2580
ggttccagga ccccaaaatc tgtgggtgct caagcccctg agataaaatg gtgtaatatt   2640
tgcatataac ctatacatac tttaaatcat ttctagatta cttataccta atacaatgga   2700
aatgacatgt cggctgggcg tggtggctca tgcctgtaat cccaccactt tgggaggccg   2760
tggcaggtgg atcacctgag gtctggagtt tgagaccagc ctgaccaaca tggtgaaacc   2820
cccatctcta ctaaaaatac aaaaattagc caggtgtggt agcgcacacc tataatccca   2880
cctacttggg aggctgaggc aggagaattg cttgaacctg ggaggcggag ttcgcagtaa   2940
gctgagatcg cgccactgta ctacagcctg ggtgacagag caggactcca tctcaaaaaa   3000
aaaagagaaa aagaaaaaga aatgccatgt aaatagttgt gatcctgaat tgtttaggga   3060
ataataagaa agaactatct gtagatgttc agtatagatg cacccatcgt aagcctaact   3120
acattgtata actcagcaac gatgtaacat tttcaggggt ttttttgttt tgttttttga   3180
gacagaatct cagtctcact ctgtcaccca ggctggagta tgttggcgtg atctctgctc   3240
actgcaacct ccacctcctg ggctcaagcg attctcctgc ctcagcctct tgagtagctg   3300
ggattgcagg tgtgcgctac cacgcatggc taatttttgt attttaata gagatgggg   3360 tttaccacgt tggtcaggct ggtcttgaac tcctgacctt gggatccgcc cacctgggcc   3420
tcccaaagtg ctgggattac aggcgttagc caccgcgccc aatatatttt gatccctggt   3480
tggatatgga gggctgactg tacttaacat ctctaagctt cagtttcctc ctttaaaata   3540
aaggtgtggc tgggtgtggt ggttcaagcc tgtaatccca gcacttaggg aggctgaggt   3600
gggtggatca gctgaggtca ggagttcaag accagcctga ccaatatggt gaaacccct   3660 ctctgctaaa aatacaaaaa ttagccaggc gtggtggcga gcgcctgtag tcccagctac   3720
```

```
ttgcttgaac ttgggaggca gaggttgcag tgagctgaga tcgtgccact gaactcgagc    3780
atgggcaaca gagcaagact gtctcaaaaa aaaaaaaaaa aagggggtga gcagacgtgg    3840
tggcacgctc ccacagtccc agctacttag taggaggcca aggttggagg attgcttgat    3900
cccaggagtc tgagtccagc ctgggcaaca tggcaatacc tcatctctaa aaataaaata    3960
aaagtaaagg tattaattac tactttggat ggttgttgca aagaaatata tataaaataa    4020
tggagagtct tgtaactggc tcccaagagg ctcaacagac attactgttt ttgcttcttc    4080
attatgagtt acctctctgg ccaccccact gaactagctg ggctagctga gcctgggaga    4140
agagttgttt aggaagtgag aggctgctct ccacagagac tcaaggctca gttcctcctg    4200
gtgactcaga tgggcagccc agtgggcaca cgtggtctct ctccacatgt ggctgagttt    4260
cacttccaga atagatggag aggcaagggc agggtttagc atgcttgagg aatctcagag    4320
ggccctggtg gtgtggggga ccctcagaac acaggtgtct caagggctga cccagcttct    4380
gtgtcctttt ctctgggtga ggaggggaca ttcatgggca gatggtgacc tctggggaag    4440
gcagcccaga ctccactggc caccatattt cctttttcac aactttctca ccctgtggt    4500 ttcccatgtc atcatgtggc cgcttccgc aaggccttag cggggtgcag gtatgaacat    4560
agtgtcaggc aaggaggcat ctggagggga accctggctt ttcctggggg gactccctcc    4620 ctgcaccta gccctgtcct ctcccatggc tactgatgcc ttcccctcac cccagaggtg    4680
gcccacatct gcacagatca gacccacaaa aatcacgtct tcctgactct cataagcctg    4740
cccagtgagg cccaggcatt aggccatgtg ctggggactc agacccacac atatacgcat    4800
gtcagcattc atgcttacag gtccgcacat gctggggcaa gtgtcacaca cggggcgctg    4860
taggaagctg actctcagcc cctgcagatt tctgcctgcc tggacaggga ggtgttgaga    4920
aggctcaggc agtcctgggc caggaccttg gcctggggct agggtactga gtgaccctag    4980
aatcaagggt ggcgtgggct taagcagttg ccagacgttc cttggtactt tgcaggcaga    5040
ccatgtggac cctggtgagc tgggtggcct taacagcagg gctggtggct ggaacgcggt    5100
gcccagatgg tcagttctgc cctgtggcct gctgcctgga ccccggagga gccagctaca    5160
gctgctgccg tccccttctg gtgagtgccc ctcagcctag gcaagagctg gcagcctggg    5220
ttttcccaaa gggtcatctt ggattggcca gaggaggacg ccaggcacaa gtctgtggtt    5280
tatcattttc cctgtctttc taggacaaat ggcccacaac actgagcagg catctgggtg    5340
gcccctgcca ggttgatgcc cactgctctg ccggccactc ctgcatcttt accgtctcag    5400
ggacttccag ttgctgcccc ttcccagagg tgagcgtgcc atcagcccag tggagggggct    5460 taggtctgca tttatgcttt tcctgcactc taccacctgc agataaaagg gccctgccaa    5520
tgcaggtttc tctgtgttcc acaggccgtg gcatgcgggg atggccatca ctgctgccca    5580
cggggcttcc actgcagtgc agacgggcga tcctgcttcc aaagatcagg tgcagctggg    5640
gtgtgggtgc agggcaggca gacgggcagc atgtggagtc tggaacccag gagcccagct    5700
ggcgggggca gccctgattc ctgcccttgt gccctcattc atgtggcatc tgtactaagc    5760
aacagccctg ctgtggacag aggggcagca ctggggatag gagggtgcgg gagaaagtgc    5820
aagactccag gtccaggcgt tgtgggggtg gggagaggtc gagctgggcc ggtctaatac    5880
caacccatgg tcagtgggtg cccctccc atgccatctt gctgagggag ggactggatt    5940
gtgaggaggg tgagttaggc ctgcctagga gatcactgag ccttagtgtc accctcaaac    6000
cccagtagct gggcttgcag gccctggtgc caccagctcc ttgtgtgatg ggggagtcac    6060
cttccctgag tgggctggta gtatcctggg tcatcttgtc cacaggtaac aactccgtgg    6120
```

```
gtgccatcca gtgccctgat agtcagttcg aatgcccgga cttctccacg tgctgtgtta    6180
tggtcgatgg ctcctggggg tgctgcccca tgcccaggt acaaatctgg gggagatggg      6240
ggtatgtgga gggaagtggg ggcagagttg ggggccaggg gcaggggtg aagacggagt      6300
caggaccatt ttttctcagg cttcctgctg tgaagacagg gtgcactgct gtccgcacgg     6360
tgccttctgc gacctggttc acaccgctg catcacaccc acgggcaccc accccctggc      6420
aaagaagctc cctgcccaga ggactaacag ggcaggtgag gaggtgggag agcatcaggc     6480
caggggctgg ggcggggcct cattgactcc aagtgtagga aaaagtttcc tccatcctgg     6540
ctgcccctca cgtttgctcc tcttccagtg gccttgtcca gctcggtcat gtgtccggac    6600
gcacggtccc ggtgccctga tggttctacc tgctgtgagc tgcccagtgg gaagtatggc     6660
tgctgcccaa tgcccaacgt gagtgagggg ctggagccag cttggctgtg tgcccccagc    6720
cacctggccc tgacacgcac cttacagggg ctctgtggca tggggctggc tggctgcttg    6780
ctgggagcct ggctgatgca gggttcatgc tacccctag tggggattg gggcagtgcc      6840
agccatcagc ctggctgctc cctgtgtgct actgagcctg gaagtgacaa agacccaccc    6900
ctgtccccac tcaggccacc tgctgctccg atcacctgca ctgctgcccc caagacactg    6960
tgtgtgacct gatccagagt aagtgcctct ccaaggagaa cgctaccacg gacctcctca    7020
ctaagctgcc tgcgcacaca ggtaccgag gcagggtgca gatacagggg tggggccccc      7080
tttcctccct tttaggcctg gccttaggat cactgcaagg tggtgtaagc ggtaccctcc    7140
atcttcaaca cctggttcca gctgtggagc cggcaaaggg ttgataccc tgagggtccc     7200
cagtgccact tctgacctgt cctctctgct tccctcacag tgggggatgt gaaatgtgac    7260
atggaggtga gctgcccaga tggctatacc tgctgccgtc tacagtcggg ggcctggggc    7320
tgctgccctt ttacccaggt acccaggggt ggcgggtggg tgggctgagc acagtgtggc    7380
aggcagccgg gccccagtgc ccacctgccc ttcttcatct gccctaggct gtgtgctgtg     7440
aggaccacat acactgctgt cccgcggggt ttacgtgtga cacgcagaag ggtacctgtg    7500
aacaggggcc ccaccaggtg ccctggatgg agaaggcccc agctcacctc agcctgccag    7560
acccacaagc cttgaagaga gatgtcccct gtgataatgt cagcagctgt ccctcctccg    7620
atacctgctg ccaactcacg tctggggagt ggggctgctg tccaatccca gaggtatatg    7680
ggagggaca gcatcttggc ctgggcaggt gggtggccaa gctcctattg ctttctgccc     7740
tccgcatagc ccataggtga tacccagctc tgacagattc gtccccagct ggaggtgctg   7800
taagcaggag aggcgggctg gagtaggtag gggctcggca ctgcgcccca catagtggct    7860
acctacaacg cccttttcctg cccaccccc aggctgtctg ctgctcggac caccagcact    7920
gctgcccccca gggctacacg tgtgtagctg aggggcagtg tcagcgagga agcgagatcg   7980
tggctggact ggagaagatg cctgcccgcc gggcttcctt atcccacccc agagacatcg    8040
gctgtgacca gcacaccagc tgcccggtgg ggcagacctg ctgcccgagc ctgggtggga    8100
gctgggcctg ctgccagttg cccatgtga gtgcctccct gcctgcccct ggatagggga   8160
gctaagccca gtgagggac aggaacataa tgccattctg tgctcccttc ccgccaggc    8220
tgtgtgctgc gaggatcgcc agcactgctg cccggctggc tacacctgca acgtgaaggc    8280
tcgatcctgc gagaaggaag tggtctctgc ccagcctgcc accttcctgg cccgtagccc     8340
tcacgtgggt gtgaaggacg tggagtgtgg ggaaggacac ttctgccatg ataaccgagac   8400
ctgctgccga gacaaccgac agggctgggc ctgctgtccc taccgccagg tcagtgccaa    8460
```

-continued

```
ccccatcct ggggctgggt atggccaggg accaggtccc acctcgtcca accctctcgc    8520
ccccctctga ccatccaggg cgtctgttgt gctgatcggc gccactgctg tcctgctggc    8580
ttccgctgcg cagccagggg taccaagtgt ttgcgcaggg aggccccgcg ctgggacgcc    8640
cctttgaggg acccagcctt gagacagctg ctgtgaggga cagtactgaa gactctgcag    8700
ccctcgggac cccactcgga gggtgccctc tgctcaggcc tccctagcac ctcccctaa    8760 ccaaattctc cctggacccc attctgagct cccatcacc atgggaggtg gggcctcaat    8820
ctaaggcctt ccctgtcaga aggggttgt ggcaaaagcc acattacaag ctgccatccc    8880
ctccccgttt cagtggaccc tgtggccagg tgcttttccc tatccacagg ggtgtttgtg    8940
tgtgtgcgcg tgtgcgtttc aataaagttt gtacactttc                         8980
```

<210> SEQ ID NO 11
<211> LENGTH: 20
<212> TYPE: DNA
<213> ORGANISM: Artificial sequence
<220> FEATURE:
<223> OTHER INFORMATION: forward primer

<400> SEQUENCE: 11
tgtcctggaa accatccttc                                               20

<210> SEQ ID NO 12
<211> LENGTH: 20
<212> TYPE: DNA
<213> ORGANISM: Artificial sequence
<220> FEATURE:
<223> OTHER INFORMATION: reverse primer

<400> SEQUENCE: 12
ctcccaaagc gattctccta                                               20

<210> SEQ ID NO 13
<211> LENGTH: 20
<212> TYPE: DNA
<213> ORGANISM: Artificial sequence
<220> FEATURE:
<223> OTHER INFORMATION: Taqman tag sequence
<220> FEATURE:
<221> NAME/KEY: variant
<222> LOCATION: (14)..(14)
<223> OTHER INFORMATION: n is a C or T

<400> SEQUENCE: 13
tcagtagctc acanttgtaa                                               20

<210> SEQ ID NO 14
<211> LENGTH: 21
<212> TYPE: DNA
<213> ORGANISM: Artificial sequence
<220> FEATURE:
<223> OTHER INFORMATION: forward primer

<400> SEQUENCE: 14
ccttccctga gtgggctggt a                                             21

<210> SEQ ID NO 15
<211> LENGTH: 21
<212> TYPE: DNA
<213> ORGANISM: Artificial sequence
<220> FEATURE:
<223> OTHER INFORMATION: reverse primer

<400> SEQUENCE: 15

```
agtgcaccct gtcttcacag c                                              21

<210> SEQ ID NO 16
<211> LENGTH: 51
<212> TYPE: DNA
<213> ORGANISM: Artificial sequence
<220> FEATURE:
<223> OTHER INFORMATION: Taqman tag sequence
<220> FEATURE:
<221> NAME/KEY: variant
<222> LOCATION: (26)..(26)
<223> OTHER INFORMATION: n is an A or G

<400> SEQUENCE: 16
aggtacaaat ctgggggaga tggggntatg tggagggaag tgggggcaga g             51

<210> SEQ ID NO 17
<211> LENGTH: 20
<212> TYPE: DNA
<213> ORGANISM: Artificial sequence
<220> FEATURE:
<223> OTHER INFORMATION: forward primer

<400> SEQUENCE: 17
ctgtcctctc ccatggctac                                                20

<210> SEQ ID NO 18
<211> LENGTH: 20
<212> TYPE: DNA
<213> ORGANISM: Artificial sequence
<220> FEATURE:
<223> OTHER INFORMATION: reverse primer

<400> SEQUENCE: 18
gcggacctgt aagcatgaat                                                20

<210> SEQ ID NO 19
<211> LENGTH: 16
<212> TYPE: DNA
<213> ORGANISM: Artificial sequence
<220> FEATURE:
<223> OTHER INFORMATION: Taqman tag sequence
<220> FEATURE:
<221> NAME/KEY: variant
<222> LOCATION: (9)..(9)
<223> OTHER INFORMATION: n is a G or C

<400> SEQUENCE: 19
aggaagacnt gatttt                                                    16

<210> SEQ ID NO 20
<211> LENGTH: 20
<212> TYPE: DNA
<213> ORGANISM: Artificial sequence
<220> FEATURE:
<223> OTHER INFORMATION: forward primer

<400> SEQUENCE: 20
ccaggggtac caagtgtttg                                                20

<210> SEQ ID NO 21
<211> LENGTH: 19
<212> TYPE: DNA
<213> ORGANISM: Artificial sequence
<220> FEATURE:
<223> OTHER INFORMATION: reverse primer
```

```
<400> SEQUENCE: 21
cacagggtcc actgaaacg                                                        19

<210> SEQ ID NO 22
<211> LENGTH: 51
<212> TYPE: DNA
<213> ORGANISM: Artificial sequence
<220> FEATURE:
<223> OTHER INFORMATION: Taqman tag sequence
<220> FEATURE:
<221> NAME/KEY: variant
<222> LOCATION: (26)..(26)
<223> OTHER INFORMATION: n is a C or T

<400> SEQUENCE: 22
tctgctcagg cctccctagc acctcnccct aaccaaattc tccctggacc c                    51

<210> SEQ ID NO 23
<211> LENGTH: 20
<212> TYPE: DNA
<213> ORGANISM: Artificial sequence
<220> FEATURE:
<223> OTHER INFORMATION: forward primer

<400> SEQUENCE: 23
ggtggtgtaa gcggtaccct                                                       20

<210> SEQ ID NO 24
<211> LENGTH: 20
<212> TYPE: DNA
<213> ORGANISM: Artificial sequence
<220> FEATURE:
<223> OTHER INFORMATION: reverse primer

<400> SEQUENCE: 24
acctgcccag gccaagatgc                                                       20
```